US012569669B2

(12) United States Patent (10) Patent No.: US 12,569,669 B2
Tuval et al. (45) Date of Patent: Mar. 10, 2026

(54) BLOOD PUMP HOUSING

(71) Applicant: MAGENTA MEDICAL LTD, Kadima (IL)

(72) Inventors: Yosi Tuval, Even Yehuda (IL); Gad Lubinsky, Ein Vered (IL); Hagit Zemer Harel, Kfar Saba (IL); Ori Friedland, Tel Aviv (IL); Daniel Rosenblum, Ramat Hasharon (IL); Avi Rozenfeld, Haifa (IL)

(73) Assignee: MAGENTA MEDICAL LTD, Kadima (IL)

( * ) Notice: Subject to any disclaimer, the term of this patent is extended or adjusted under 35 U.S.C. 154(b) by 159 days.

(21) Appl. No.: 18/122,456

(22) Filed: Mar. 16, 2023

(65) Prior Publication Data

US 2023/0233836 A1      Jul. 27, 2023

Related U.S. Application Data

(63) Continuation of application No. 18/001,680, filed as application No. PCT/IB2022/051990 on Mar. 7, 2022.

(Continued)

(51) Int. Cl.
*B23P 11/00* (2006.01)
*A61M 60/148* (2021.01)
(Continued)

(52) U.S. Cl.
CPC ........ *A61M 60/414* (2021.01); *A61M 60/148* (2021.01); *A61M 60/178* (2021.01);
(Continued)

(58) Field of Classification Search
CPC .............. A61M 60/414; A61M 60/808; A61M 2207/10; A61M 60/81; B23P 11/005;
(Continued)

(56) References Cited

U.S. PATENT DOCUMENTS 3,592,183 A      7/1971  Watkins et al.
3,932,068 A      1/1976  Zimmermann
(Continued)

FOREIGN PATENT DOCUMENTS

AU      2013205145 A1      5/2013
CA      2701809 A1      4/2009
(Continued)

OTHER PUBLICATIONS

Corrected Notice of Allowance for U.S. Appl. No. 16/275,559 mailed Nov. 8, 2023.

(Continued)

*Primary Examiner* — Jermie E Cozart
(74) *Attorney, Agent, or Firm* — Ballard Spahr LLP

(57) ABSTRACT

Apparatus and methods are described for manufacturing a housing for an impeller of a blood pump. A frame is treated in order to enhance bonding between an inner surface of the frame and an inner lining. Subsequently, the inner lining is coupled to the inner surface of the frame along at least a portion of a central cylindrical portion of the frame. Subsequent to coupling the inner lining to the inner surface of the frame along at least a portion of the central cylindrical portion of the frame, a portion of an elongate tube is placed around at least a portion of the frame. While heating the inner lining, the frame, and the portion of the elongate tube, pressure is applied such as to cause the portion of the elongate tube to become coupled to the frame. Other applications are also described.

17 Claims, 21 Drawing Sheets

FIG. 16

Treat frame

Couple inner lining to inner surface of frame

Place mandrel inside inner lining

Place portion of elongate tube around frame

Heat inner lining, frame, and portion of elongate tube via mandrel

Apply pressure

Related U.S. Application Data

(60) Provisional application No. 63/254,321, filed on Oct. 11, 2021, provisional application No. 63/158,708, filed on Mar. 9, 2021.

(51) Int. Cl.

| | |
|---|---|
| *A61M 60/178* | (2021.01) |
| *A61M 60/237* | (2021.01) |
| *A61M 60/247* | (2021.01) |
| *A61M 60/411* | (2021.01) |
| *A61M 60/414* | (2021.01) |
| *A61M 60/508* | (2021.01) |
| *A61M 60/808* | (2021.01) |
| *A61M 60/81* | (2021.01) |
| *A61M 60/818* | (2021.01) |
| *A61M 60/865* | (2021.01) |
| *B23P 11/02* | (2006.01) |
| *A61M 60/13* | (2021.01) |
| *A61M 60/205* | (2021.01) |

(52) U.S. Cl.
CPC ........ *A61M 60/237* (2021.01); *A61M 60/247* (2021.01); *A61M 60/411* (2021.01); *A61M 60/508* (2021.01); *A61M 60/808* (2021.01); *A61M 60/81* (2021.01); *A61M 60/818* (2021.01); *A61M 60/865* (2021.01); *B23P 11/005* (2013.01); *B23P 11/025* (2013.01); *A61M 60/13* (2021.01); *A61M 60/205* (2021.01); *A61M 2207/00* (2013.01); *A61M 2207/10* (2013.01); *Y10T 29/49865* (2015.01); *Y10T 29/49885* (2015.01); *Y10T 29/49913* (2015.01); *Y10T 29/49927* (2015.01)

(58) Field of Classification Search
CPC .............. B23P 11/025; Y10T 29/49865; Y10T 29/49913; Y10T 29/49885; Y10T 29/49927
See application file for complete search history.

(56) References Cited

U.S. PATENT DOCUMENTS

| | | | |
|---|---|---|---|
| 4,625,712 | A | 12/1986 | Wampler |
| 4,753,221 | A | 6/1988 | Kensey et al. |
| 4,771,765 | A | 9/1988 | Peters |
| 4,919,647 | A | 4/1990 | Nash |
| 4,944,722 | A | 7/1990 | Carriker et al. |
| 4,954,055 | A | 9/1990 | Raible et al. |
| 4,957,504 | A | 9/1990 | Chardack |
| 4,964,864 | A | 10/1990 | Summers et al. |
| 4,969,865 | A | 11/1990 | Hwang et al. |
| 4,985,014 | A | 1/1991 | Orejola |
| 5,011,469 | A | 4/1991 | Buckberg et al. |
| 5,037,403 | A | 8/1991 | Garcia |
| 5,061,256 | A | 10/1991 | Wampler |
| 5,169,378 | A | 12/1992 | Figuera |
| 5,275,580 | A | 1/1994 | Yamazaki |
| 5,330,484 | A | 7/1994 | Guenther et al. |
| 5,348,545 | A | 9/1994 | Shani et al. |
| 5,507,629 | A | 4/1996 | Jarvik |
| 5,531,789 | A | 7/1996 | Yamazaki et al. |
| 5,569,275 | A | 10/1996 | Kotula et al. |
| 5,613,935 | A | 3/1997 | Jarvik |
| 5,692,882 | A | 12/1997 | Bozeman et al. |
| 5,713,730 | A | 2/1998 | Nose et al. |
| 5,749,855 | A | 5/1998 | Reitan |
| 5,772,693 | A | 6/1998 | Brownlee |
| 5,843,158 | A | 12/1998 | Lenker et al. |
| 5,863,179 | A | 1/1999 | Westphal et al. |
| 5,876,385 | A | 3/1999 | Ikari et al. |
| 5,879,499 | A | 3/1999 | Corvi |
| 5,911,685 | A | 6/1999 | Siess et al. |
| 5,928,132 | A | 7/1999 | Leschinsky |
| 5,947,892 | A | 9/1999 | Benkowski et al. |
| 5,957,672 | A | 9/1999 | Aber |
| 5,964,694 | A | 10/1999 | Siess et al. |
| 6,007,478 | A | 12/1999 | Siess et al. |
| 6,086,527 | A | 7/2000 | Talpade |
| 6,116,862 | A | 9/2000 | Rau et al. |
| 6,135,729 | A | 10/2000 | Aber |
| 6,136,025 | A | 10/2000 | Barbut et al. |
| 6,162,017 | A | 12/2000 | Raible |
| 6,176,848 | B1 | 1/2001 | Rau et al. |
| 6,183,220 | B1 | 2/2001 | Ohara et al. |
| 6,217,541 | B1 | 4/2001 | Yu |
| 6,247,892 | B1 | 6/2001 | Kazatchkov et al. |
| 6,355,001 | B1 | 3/2002 | Quinn et al. |
| 6,413,222 | B1 | 7/2002 | Pantages et al. |
| 6,482,228 | B1 | 11/2002 | Norred |
| 6,506,146 | B1 | 1/2003 | Mohl |
| 6,533,716 | B1 | 3/2003 | Schmutz-Rode et al. |
| 6,533,770 | B1 | 3/2003 | Lepulu et al. |
| 6,537,315 | B2 | 3/2003 | Yamazaki et al. |
| 6,544,216 | B1 | 4/2003 | Sammler et al. |
| 6,592,567 | B1 | 7/2003 | Levin et al. |
| 6,616,624 | B1 | 9/2003 | Kieval |
| 6,884,210 | B2 | 4/2005 | Nose et al. |
| 6,949,066 | B2 | 9/2005 | Bearnson et al. |
| 6,974,436 | B1 | 12/2005 | Aboul-Hosn et al. |
| 7,004,925 | B2 | 2/2006 | Navia et al. |
| 7,010,954 | B2 | 3/2006 | Siess et al. |
| 7,011,620 | B1 | 3/2006 | Siess |
| 7,022,100 | B1 | 4/2006 | Aboul-Hosn et al. |
| 7,027,875 | B2 | 4/2006 | Siess et al. |
| 7,070,555 | B2 | 7/2006 | Siess |
| 7,144,364 | B2 | 12/2006 | Barbut et al. |
| 7,159,593 | B2 | 1/2007 | McCarthy et al. |
| 7,201,772 | B2 | 4/2007 | Schwammenthal et al. |
| 7,258,679 | B2 | 8/2007 | Moore et al. |
| 7,335,192 | B2 | 2/2008 | Keren et al. |
| 7,338,521 | B2 | 3/2008 | Antaki et al. |
| 7,341,570 | B2 | 3/2008 | Keren et al. |
| 7,393,181 | B2 | 7/2008 | McBride et al. |
| 7,485,104 | B2 | 2/2009 | Kieval |
| 7,717,952 | B2 | 5/2010 | Case et al. |
| 7,744,642 | B2 | 6/2010 | Rittgers et al. |
| 7,762,941 | B2 | 7/2010 | Jarvik |
| 7,766,853 | B2 | 8/2010 | Lane |
| 7,766,892 | B2 | 8/2010 | Keren et al. |
| 7,766,961 | B2 | 8/2010 | Patel et al. |
| 7,780,628 | B1 | 8/2010 | Keren et al. |
| 7,811,221 | B2 | 10/2010 | Gross |
| 7,841,976 | B2 | 11/2010 | McBride et al. |
| 7,878,967 | B1 | 2/2011 | Khanal |
| 7,914,436 | B1 | 3/2011 | Kung |
| 7,914,503 | B2 | 3/2011 | Goodson et al. |
| 7,927,068 | B2 | 4/2011 | Mcbride et al. |
| 8,012,121 | B2 | 9/2011 | Goodson et al. |
| 8,079,948 | B2 | 12/2011 | Shifflette |
| 8,118,723 | B2 | 2/2012 | Richardson et al. |
| 8,123,669 | B2 | 2/2012 | Siess et al. |
| 8,157,758 | B2 | 4/2012 | Pecor et al. |
| 8,192,451 | B2 | 6/2012 | Cambronne et al. |
| 8,216,122 | B2 | 7/2012 | Kung |
| 8,221,492 | B2 | 7/2012 | Case et al. |
| 8,235,933 | B2 | 8/2012 | Keren et al. |
| 8,277,470 | B2 | 10/2012 | Demarais et al. |
| 8,376,707 | B2 | 2/2013 | Mcbride et al. |
| 8,439,859 | B2 | 5/2013 | Pfeffer et al. |
| 8,449,443 | B2 | 5/2013 | Rodefeld et al. |
| 8,485,961 | B2 | 7/2013 | Campbell et al. |
| 8,489,190 | B2 | 7/2013 | Pfeffer et al. |
| 8,512,262 | B2 | 8/2013 | Gertner |
| 8,535,211 | B2 | 9/2013 | Walters et al. |
| 8,538,535 | B2 | 9/2013 | Ariav et al. |
| 8,579,858 | B2 | 11/2013 | Reitan et al. |
| 8,591,393 | B2 | 11/2013 | Walters et al. |
| 8,591,539 | B2 | 11/2013 | Gellman |
| 8,597,170 | B2 | 12/2013 | Walters et al. |
| 8,617,239 | B2 | 12/2013 | Reitan |

(56) References Cited

U.S. PATENT DOCUMENTS

| | | |
|---|---|---|
| 8,672,868 B2 | 3/2014 | Simons |
| 8,684,904 B2 | 4/2014 | Campbell et al. |
| 8,690,749 B1 | 4/2014 | Nunez |
| 8,721,516 B2 | 5/2014 | Scheckel |
| 8,721,517 B2 | 5/2014 | Zeng et al. |
| 8,727,959 B2 | 5/2014 | Reitan et al. |
| 8,734,331 B2 | 5/2014 | Evans et al. |
| 8,734,508 B2 | 5/2014 | Hastings et al. |
| 8,777,832 B1 | 7/2014 | Wang et al. |
| 8,814,543 B2 | 8/2014 | Liebing |
| 8,814,776 B2 | 8/2014 | Hastie et al. |
| 8,814,933 B2 | 8/2014 | Siess |
| 8,827,887 B2 | 9/2014 | Curtis et al. |
| 8,849,398 B2 | 9/2014 | Evans |
| 8,864,642 B2 | 10/2014 | Scheckel |
| 8,888,728 B2 | 11/2014 | Aboul-Hosn et al. |
| 8,900,060 B2 | 12/2014 | Liebing |
| 8,926,492 B2 | 1/2015 | Scheckel |
| 8,932,141 B2 | 1/2015 | Liebing |
| 8,944,748 B2 | 2/2015 | Liebing |
| 8,979,493 B2 | 3/2015 | Roehn |
| 8,992,163 B2 | 3/2015 | Mcbride et al. |
| 8,998,792 B2 | 4/2015 | Scheckel |
| 9,028,216 B2 | 5/2015 | Schumacher et al. |
| 9,067,006 B2 | 6/2015 | Toellner |
| 9,072,825 B2 | 7/2015 | Pfeffer et al. |
| 9,089,634 B2 | 7/2015 | Schumacher et al. |
| 9,138,518 B2 | 9/2015 | Campbell et al. |
| 9,162,017 B2 | 10/2015 | Evans et al. |
| 9,162,019 B2 | 10/2015 | Horvath et al. |
| 9,217,442 B2 | 12/2015 | Wiessler et al. |
| 9,259,521 B2 | 2/2016 | Simons |
| 9,278,189 B2 | 3/2016 | Corbett |
| 9,314,558 B2 | 4/2016 | Er |
| 9,327,067 B2 | 5/2016 | Zeng et al. |
| 9,328,741 B2 | 5/2016 | Liebing |
| 9,339,596 B2 | 5/2016 | Roehn |
| 9,345,824 B2 | 5/2016 | Mohl et al. |
| 9,358,329 B2 | 6/2016 | Fitzgerald et al. |
| 9,358,330 B2 | 6/2016 | Schumacher |
| 9,364,592 B2 | 6/2016 | Mcbride et al. |
| 9,364,593 B2 | 6/2016 | Mcbride et al. |
| 9,370,613 B2 | 6/2016 | Hsu et al. |
| 9,381,288 B2 | 7/2016 | Schenck et al. |
| 9,393,384 B1 | 7/2016 | Kapur et al. |
| 9,402,942 B2 | 8/2016 | Hastie et al. |
| 9,404,505 B2 | 8/2016 | Scheckel |
| 9,416,783 B2 | 8/2016 | Schumacher et al. |
| 9,416,791 B2 | 8/2016 | Toellner |
| 9,421,311 B2 | 8/2016 | Tanner et al. |
| 9,446,179 B2 | 9/2016 | Keenan et al. |
| 9,474,840 B2 | 10/2016 | Siess |
| 9,512,839 B2 | 12/2016 | Liebing |
| 9,533,082 B2 | 1/2017 | Reichenbach et al. |
| 9,533,084 B2 | 1/2017 | Siess et al. |
| 9,545,468 B2 | 1/2017 | Aboul-Hosn et al. |
| 9,550,017 B2 | 1/2017 | Spanier et al. |
| 9,561,314 B2 | 2/2017 | Aboul-Hosn et al. |
| 9,572,915 B2 | 2/2017 | Heuring et al. |
| 9,597,205 B2 | 3/2017 | Tuval |
| 9,597,437 B2 | 3/2017 | Aboul-Hosn et al. |
| 9,603,983 B2 | 3/2017 | Roehn et al. |
| 9,611,743 B2 | 4/2017 | Toellner et al. |
| 9,616,159 B2 | 4/2017 | Anderson et al. |
| 9,623,161 B2 | 4/2017 | Medvedev et al. |
| 9,669,142 B2 | 6/2017 | Spanier et al. |
| 9,669,144 B2 | 6/2017 | Spanier et al. |
| 9,675,738 B2 | 6/2017 | Tanner et al. |
| 9,675,740 B2 | 6/2017 | Zeng et al. |
| 9,713,663 B2 | 7/2017 | Medvedev et al. |
| 9,717,833 B2 | 8/2017 | Mcbride et al. |
| 9,750,860 B2 | 9/2017 | Schumacher |
| 9,750,861 B2 | 9/2017 | Hastie et al. |
| 9,759,237 B2 | 9/2017 | Liebing |
| 9,764,113 B2 | 9/2017 | Tuval et al. |
| 9,771,801 B2 | 9/2017 | Schumacher et al. |
| 9,789,238 B2 | 10/2017 | Aboul-Hosn et al. |
| 9,795,727 B2 | 10/2017 | Schumacher |
| 9,814,814 B2 | 11/2017 | Corbett et al. |
| 9,821,146 B2 | 11/2017 | Tao et al. |
| 9,827,356 B2 | 11/2017 | Muller et al. |
| 9,833,550 B2 | 12/2017 | Siess |
| 9,835,550 B2 | 12/2017 | Kakuno et al. |
| 9,850,906 B2 | 12/2017 | Ozaki et al. |
| 9,872,947 B2 | 1/2018 | Keenan et al. |
| 9,872,948 B2 | 1/2018 | Siess |
| 9,878,079 B2 | 1/2018 | Pfeffer et al. |
| 9,889,242 B2 | 2/2018 | Pfeffer et al. |
| 9,895,475 B2 | 2/2018 | Toellner et al. |
| 9,903,384 B2 | 2/2018 | Roehn |
| 9,907,890 B2 | 3/2018 | Muller |
| 9,907,891 B2 | 3/2018 | Wiessler et al. |
| 9,919,087 B2 | 3/2018 | Pfeffer et al. |
| 9,962,475 B2 | 5/2018 | Campbell et al. |
| 9,964,115 B2 | 5/2018 | Scheckel |
| 9,974,893 B2 | 5/2018 | Toellner |
| 9,999,714 B2 | 6/2018 | Spanier et al. |
| 10,029,037 B2 | 7/2018 | Muller et al. |
| 10,029,040 B2 | 7/2018 | Taskin |
| 10,039,872 B2 | 8/2018 | Zeng et al. |
| 10,039,874 B2 | 8/2018 | Schwammenthal et al. |
| 10,052,419 B2 | 8/2018 | Er |
| 10,052,420 B2 | 8/2018 | Medvedev et al. |
| 10,071,192 B2 | 9/2018 | Zeng |
| 10,086,121 B2 | 10/2018 | Fitzgerald et al. |
| 10,105,475 B2 | 10/2018 | Muller |
| 10,107,299 B2 | 10/2018 | Scheckel |
| 10,117,980 B2 | 11/2018 | Keenan et al. |
| 10,119,550 B2 | 11/2018 | Bredenbreuker et al. |
| 10,149,932 B2 | 12/2018 | Mcbride et al. |
| 10,172,985 B2 | 1/2019 | Simon et al. |
| 10,179,197 B2 | 1/2019 | Kaiser et al. |
| 10,183,104 B2 | 1/2019 | Anderson et al. |
| 10,196,899 B2 | 2/2019 | Toellner et al. |
| 10,207,037 B2 | 2/2019 | Corbett et al. |
| 10,208,763 B2 | 2/2019 | Schumacher et al. |
| 10,215,187 B2 | 2/2019 | Mcbride et al. |
| 10,221,866 B2 | 3/2019 | Liebing |
| 10,231,838 B2 | 3/2019 | Chin et al. |
| 10,232,099 B2 | 3/2019 | Tuval |
| 10,238,783 B2 | 3/2019 | Aboul-Hosn et al. |
| 10,245,363 B1 | 4/2019 | Rowe |
| 10,265,447 B2 | 4/2019 | Campbell et al. |
| 10,265,448 B2 | 4/2019 | Liebing |
| 10,279,095 B2 | 5/2019 | Aboul-Hosn et al. |
| 10,300,185 B2 | 5/2019 | Aboul-Hosn et al. |
| 10,300,186 B2 | 5/2019 | Aboul-Hosn et al. |
| 10,316,853 B2 | 6/2019 | Toellner |
| 10,322,175 B2 | 6/2019 | Cully et al. |
| 10,330,101 B2 | 6/2019 | Toellner |
| 10,342,904 B2 | 7/2019 | Schumacher |
| 10,342,906 B2 | 7/2019 | D'Ambrosio et al. |
| 10,363,349 B2 | 7/2019 | Muller et al. |
| 10,369,260 B2 | 8/2019 | Smith et al. |
| 10,376,162 B2 | 8/2019 | Edelman et al. |
| 10,413,646 B2 | 9/2019 | Wiessler et al. |
| 10,449,276 B2 | 10/2019 | Pfeffer et al. |
| 10,449,279 B2 | 10/2019 | Muller |
| 10,478,538 B2 | 11/2019 | Scheckel et al. |
| 10,478,539 B2 | 11/2019 | Pfeffer et al. |
| 10,478,540 B2 | 11/2019 | Scheckel et al. |
| 10,495,101 B2 | 12/2019 | Scheckel |
| 10,557,475 B2 | 2/2020 | Roehn |
| 10,583,231 B2 | 3/2020 | Schwammenthal et al. |
| 10,584,589 B2 | 3/2020 | Schumacher et al. |
| 10,589,012 B2 | 3/2020 | Toellner et al. |
| 10,617,808 B2 | 4/2020 | Hastie et al. |
| 10,662,967 B2 | 5/2020 | Scheckel |
| 10,669,855 B2 | 6/2020 | Toellner et al. |
| 10,765,789 B2 | 9/2020 | Zeng et al. |
| 10,792,406 B2 | 10/2020 | Roehn et al. |
| 10,799,624 B2 | 10/2020 | Pfeffer et al. |
| 10,799,626 B2 | 10/2020 | Siess et al. |
| 10,801,511 B2 | 10/2020 | Siess et al. |

(56) References Cited

U.S. PATENT DOCUMENTS

| | | | |
|---|---|---|---|
| 10,806,838 | B2 | 10/2020 | Er |
| 10,835,653 | B2 | 11/2020 | Liebing |
| 10,842,922 | B2 | 11/2020 | Roehn et al. |
| 10,857,272 | B2 | 12/2020 | Liebing |
| 10,864,309 | B2 | 12/2020 | Mcbride et al. |
| 10,864,310 | B2 | 12/2020 | Schwammenthal et al. |
| 10,865,801 | B2 | 12/2020 | Mcbride et al. |
| 10,874,783 | B2 | 12/2020 | Pfeffer et al. |
| 10,881,770 | B2 | 1/2021 | Tuval et al. |
| 10,881,845 | B2 | 1/2021 | Siess et al. |
| 10,894,115 | B2 | 1/2021 | Pfeffer et al. |
| 10,898,629 | B2 | 1/2021 | Siess et al. |
| 10,907,646 | B2 | 2/2021 | Bredenbreuker et al. |
| 10,920,596 | B2 | 2/2021 | Toellner et al. |
| 10,926,013 | B2 | 2/2021 | Schumacher et al. |
| 10,935,038 | B2 | 3/2021 | Siess |
| 10,980,927 | B2 | 4/2021 | Pfeffer et al. |
| 10,994,120 | B2 | 5/2021 | Tuval et al. |
| 11,007,350 | B2 | 5/2021 | Tao et al. |
| 11,020,584 | B2 | 6/2021 | Siess et al. |
| 11,027,114 | B2 | 6/2021 | D'Ambrosio et al. |
| 11,033,729 | B2 | 6/2021 | Scheckel et al. |
| 11,040,187 | B2 | 6/2021 | Wiessler et al. |
| RE48,649 | E | 7/2021 | Siess |
| 11,077,294 | B2 | 8/2021 | Keenan et al. |
| 11,107,626 | B2 | 8/2021 | Siess et al. |
| 11,116,960 | B2 | 9/2021 | Simon et al. |
| 11,123,539 | B2 | 9/2021 | Pfeffer et al. |
| 11,129,978 | B2 | 9/2021 | Pfeffer et al. |
| 11,167,124 | B2 | 11/2021 | Pfeffer et al. |
| 11,168,705 | B2 | 11/2021 | Liebing |
| 11,185,679 | B2 | 11/2021 | Tuval |
| 11,185,680 | B2 | 11/2021 | Tuval et al. |
| 11,191,944 | B2 | 12/2021 | Tuval et al. |
| 11,197,690 | B2 | 12/2021 | Fantuzzi et al. |
| 11,219,755 | B2 | 1/2022 | Siess et al. |
| 11,229,786 | B2 | 1/2022 | Zeng et al. |
| 11,253,692 | B2 | 2/2022 | Schumacher |
| 11,253,693 | B2 | 2/2022 | Pfeffer et al. |
| 11,260,212 | B2 | 3/2022 | Tuval et al. |
| 11,260,213 | B2 | 3/2022 | Zeng et al. |
| 11,260,215 | B2 | 3/2022 | Scheckel et al. |
| 11,266,824 | B2 | 3/2022 | Er |
| 11,268,521 | B2 | 3/2022 | Toellner |
| 11,273,301 | B2 | 3/2022 | Pfeffer et al. |
| 11,278,711 | B2 | 3/2022 | Liebing |
| 11,280,345 | B2 | 3/2022 | Bredenbreuker et al. |
| 11,285,309 | B2 | 3/2022 | Tuval |
| 11,291,825 | B2 | 4/2022 | Tuval et al. |
| 11,298,523 | B2 | 4/2022 | Tuval |
| 11,298,525 | B2 | 4/2022 | Jahangir |
| 11,305,105 | B2 | 4/2022 | Corbett et al. |
| 11,313,228 | B2 | 4/2022 | Schumacher et al. |
| 11,338,124 | B2 | 5/2022 | Pfeffer et al. |
| 11,351,358 | B2 | 6/2022 | Nix et al. |
| 11,364,373 | B2 | 6/2022 | Corbett et al. |
| 11,421,701 | B2 | 8/2022 | Schumacher et al. |
| 11,434,922 | B2 | 9/2022 | Roehn |
| 11,471,663 | B2 | 10/2022 | Tuval |
| 11,708,833 | B2 | 7/2023 | Mcbride et al. |
| 11,833,278 | B2 | 12/2023 | Siess et al. |
| 11,883,274 | B2 | 1/2024 | Schwammenthal et al. |
| 12,329,957 | B2 | 6/2025 | Tuval et al. |
| 2001/0031210 | A1 | 10/2001 | Antaki et al. |
| 2001/0031981 | A1 | 10/2001 | Evans et al. |
| 2001/0041934 | A1 | 11/2001 | Yamazaki et al. |
| 2002/0107536 | A1 | 8/2002 | Hussein |
| 2002/0151799 | A1 | 10/2002 | Pantages et al. |
| 2003/0055486 | A1 | 3/2003 | Adams et al. |
| 2003/0088310 | A1 | 5/2003 | Hansen et al. |
| 2003/0100816 | A1 | 5/2003 | Siess |
| 2003/0135086 | A1 | 7/2003 | Khaw et al. |
| 2003/0149473 | A1 | 8/2003 | Chouinard et al. |
| 2003/0187322 | A1 | 10/2003 | Siess |
| 2003/0208097 | A1 | 11/2003 | Aboul-Hosn et al. |
| 2004/0064090 | A1 | 4/2004 | Keren et al. |
| 2004/0064091 | A1 | 4/2004 | Keren et al. |
| 2004/0111006 | A1 | 6/2004 | Alferness et al. |
| 2004/0116769 | A1 | 6/2004 | Jassawalla et al. |
| 2004/0167415 | A1 | 8/2004 | Gelfand et al. |
| 2004/0210236 | A1 | 10/2004 | Allers et al. |
| 2004/0260389 | A1 | 12/2004 | Case et al. |
| 2005/0033406 | A1 | 2/2005 | Barnhart et al. |
| 2005/0049692 | A1 | 3/2005 | Numamoto et al. |
| 2005/0079274 | A1 | 4/2005 | Palasis et al. |
| 2005/0085848 | A1 | 4/2005 | Johnson et al. |
| 2005/0119682 | A1 | 6/2005 | Nguyen et al. |
| 2005/0137680 | A1 | 6/2005 | Ortiz et al. |
| 2005/0180854 | A1 | 8/2005 | Grabau et al. |
| 2006/0062672 | A1 | 3/2006 | McBride et al. |
| 2006/0064059 | A1 | 3/2006 | Gelfand et al. |
| 2006/0106449 | A1 | 5/2006 | Ben |
| 2006/0135961 | A1 | 6/2006 | Rosenman et al. |
| 2006/0155322 | A1 | 7/2006 | Sater et al. |
| 2006/0265051 | A1 | 11/2006 | Caro et al. |
| 2007/0100415 | A1 | 5/2007 | Licata et al. |
| 2007/0100435 | A1 | 5/2007 | Case et al. |
| 2007/0142729 | A1 | 6/2007 | Pfeiffer et al. |
| 2007/0162103 | A1 | 7/2007 | Case et al. |
| 2007/0208291 | A1 | 9/2007 | Patel |
| 2007/0260327 | A1 | 11/2007 | Case et al. |
| 2007/0282243 | A1 | 12/2007 | Pini et al. |
| 2007/0282413 | A1 | 12/2007 | Tockman et al. |
| 2007/0293808 | A1 | 12/2007 | Williams et al. |
| 2008/0009668 | A1 | 1/2008 | Cohn |
| 2008/0086027 | A1 | 4/2008 | Siess et al. |
| 2008/0103591 | A1 | 5/2008 | Siess |
| 2008/0114339 | A1 | 5/2008 | McBride et al. |
| 2008/0114374 | A1 | 5/2008 | Soma et al. |
| 2008/0132747 | A1 | 6/2008 | Shifflette |
| 2008/0132748 | A1 | 6/2008 | Shifflette |
| 2008/0140189 | A1 | 6/2008 | Nguyen et al. |
| 2008/0154236 | A1 | 6/2008 | Elkins et al. |
| 2008/0183280 | A1 | 7/2008 | Agnew et al. |
| 2008/0306327 | A1 | 12/2008 | Shifflette |
| 2008/0306328 | A1 | 12/2008 | Ercolani et al. |
| 2009/0024157 | A1 | 1/2009 | Anukhin |
| 2009/0024195 | A1 | 1/2009 | Rezai et al. |
| 2009/0062597 | A1 | 3/2009 | Shifflette |
| 2009/0093764 | A1 | 4/2009 | Pfeffer et al. |
| 2009/0093796 | A1 | 4/2009 | Pfeffer et al. |
| 2009/0264991 | A1 | 10/2009 | Paul et al. |
| 2009/0287299 | A1 | 11/2009 | Tabor et al. |
| 2009/0318857 | A1 | 12/2009 | Goodson et al. |
| 2010/0030098 | A1 | 2/2010 | Fojtik |
| 2010/0048793 | A1 | 2/2010 | Baekelandt et al. |
| 2010/0049313 | A1 | 2/2010 | Alon et al. |
| 2010/0076247 | A1 | 3/2010 | Zilbershlag et al. |
| 2010/0130810 | A1 | 5/2010 | Mohl |
| 2010/0152523 | A1 | 6/2010 | Macdonald et al. |
| 2010/0185043 | A1 | 7/2010 | Woodard et al. |
| 2010/0222632 | A1 | 9/2010 | Poirier |
| 2010/0268017 | A1 | 10/2010 | Siess |
| 2010/0285084 | A1 | 11/2010 | Yang et al. |
| 2011/0004046 | A1 | 1/2011 | Campbell et al. |
| 2011/0034874 | A1 | 2/2011 | Reitan et al. |
| 2011/0106244 | A1 | 5/2011 | Ferrari et al. |
| 2011/0112567 | A1 | 5/2011 | Lenker et al. |
| 2011/0144633 | A1 | 6/2011 | Govari |
| 2011/0152999 | A1 | 6/2011 | Hastings et al. |
| 2011/0160858 | A1 | 6/2011 | Link |
| 2011/0190874 | A1 | 8/2011 | Celermajer et al. |
| 2011/0213408 | A1 | 9/2011 | Gross et al. |
| 2011/0230949 | A1 | 9/2011 | Haverkost et al. |
| 2011/0257462 | A1 | 10/2011 | Rodefeld et al. |
| 2011/0264075 | A1 | 10/2011 | Leung et al. |
| 2011/0282128 | A1 | 11/2011 | Reitan et al. |
| 2011/0282274 | A1 | 11/2011 | Fulton |
| 2011/0301662 | A1 | 12/2011 | Bar-Yoseph et al. |
| 2012/0022579 | A1 | 1/2012 | Fulton |
| 2012/0059460 | A1 | 3/2012 | Reitan |
| 2012/0089047 | A1 | 4/2012 | Ryba et al. |
| 2012/0089225 | A1 | 4/2012 | Akkerman et al. |
| 2012/0093628 | A1 | 4/2012 | Liebing |

(56) References Cited

U.S. PATENT DOCUMENTS

| | | |
|---|---|---|
| 2012/0116382 A1 | 5/2012 | Ku et al. |
| 2012/0130469 A1 | 5/2012 | Cragg et al. |
| 2012/0143141 A1 | 6/2012 | Verkaik et al. |
| 2012/0172654 A1 | 7/2012 | Bates |
| 2012/0172655 A1 | 7/2012 | Campbell et al. |
| 2012/0172656 A1 | 7/2012 | Walters et al. |
| 2012/0178985 A1 | 7/2012 | Walters et al. |
| 2012/0178986 A1 | 7/2012 | Campbell et al. |
| 2012/0224970 A1 | 9/2012 | Schumacher et al. |
| 2012/0234411 A1 | 9/2012 | Scheckel |
| 2012/0237353 A1 | 9/2012 | Schumacher et al. |
| 2012/0237357 A1 | 9/2012 | Schumacher et al. |
| 2012/0245680 A1 | 9/2012 | Masuzawa et al. |
| 2012/0303112 A1 | 11/2012 | Armstrong et al. |
| 2012/0316586 A1 | 12/2012 | Demarais et al. |
| 2012/0328460 A1 | 12/2012 | Horvath et al. |
| 2013/0041202 A1 | 2/2013 | Toellner |
| 2013/0046376 A1 | 2/2013 | Hassan et al. |
| 2013/0053623 A1 | 2/2013 | Evans et al. |
| 2013/0053732 A1 | 2/2013 | Heuser |
| 2013/0060077 A1 | 3/2013 | Liebing |
| 2013/0066140 A1 | 3/2013 | McBride et al. |
| 2013/0079874 A1 | 3/2013 | Doss et al. |
| 2013/0085318 A1 | 4/2013 | Toellner |
| 2013/0085319 A1 | 4/2013 | Evans et al. |
| 2013/0177407 A1 | 7/2013 | Farineau et al. |
| 2013/0177409 A1 | 7/2013 | Schumacher et al. |
| 2013/0177432 A1 | 7/2013 | Toellner et al. |
| 2013/0237744 A1 | 9/2013 | Pfeffer et al. |
| 2013/0245360 A1 | 9/2013 | Schumacher |
| 2013/0253328 A1 | 9/2013 | Zelenka et al. |
| 2013/0303831 A1 | 11/2013 | Evans |
| 2013/0303969 A1 | 11/2013 | Keenan et al. |
| 2013/0331639 A1 | 12/2013 | Campbell et al. |
| 2014/0018840 A1 | 1/2014 | Morgan et al. |
| 2014/0025041 A1 | 1/2014 | Fukuoka et al. |
| 2014/0128659 A1 | 5/2014 | Heuring et al. |
| 2014/0255176 A1 | 9/2014 | Bredenbreuker et al. |
| 2014/0275720 A1 | 9/2014 | Ferrari |
| 2014/0275722 A1 | 9/2014 | Zimmermann et al. |
| 2014/0350523 A1 | 11/2014 | Dehdashtian et al. |
| 2015/0005570 A1 | 1/2015 | Fritz et al. |
| 2015/0018597 A1 | 1/2015 | Fierens et al. |
| 2015/0051435 A1 | 2/2015 | Siess et al. |
| 2015/0119633 A1 | 4/2015 | Haselby et al. |
| 2015/0157777 A1 | 6/2015 | Tuval et al. |
| 2015/0164372 A1 | 6/2015 | Navab et al. |
| 2015/0164662 A1 | 6/2015 | Tuval |
| 2015/0176582 A1 | 6/2015 | Liebing |
| 2015/0258262 A1 | 9/2015 | Pfeffer et al. |
| 2015/0290372 A1 | 10/2015 | Muller et al. |
| 2015/0306291 A1 | 10/2015 | Bonde et al. |
| 2015/0328382 A1 | 11/2015 | Corbett et al. |
| 2015/0343136 A1 | 12/2015 | Nitzan et al. |
| 2015/0343179 A1 | 12/2015 | Schumacher et al. |
| 2015/0343186 A1 | 12/2015 | Nitzan et al. |
| 2016/0022890 A1 | 1/2016 | Schwammenthal et al. |
| 2016/0051741 A1 | 2/2016 | Schwammenthal et al. |
| 2016/0053768 A1 | 2/2016 | Schumacher et al. |
| 2016/0106896 A1 | 4/2016 | Pfeffer et al. |
| 2016/0129170 A1 | 5/2016 | Siess |
| 2016/0136341 A1 | 5/2016 | Pfeffer et al. |
| 2016/0136342 A1 | 5/2016 | Pfeffer et al. |
| 2016/0136343 A1 | 5/2016 | Anagnostopoulos |
| 2016/0144089 A1 | 5/2016 | Woo et al. |
| 2016/0184500 A1 | 6/2016 | Zeng |
| 2016/0213827 A1 | 7/2016 | Tanner |
| 2016/0256620 A1 | 9/2016 | Scheckel et al. |
| 2016/0279310 A1 | 9/2016 | Scheckel et al. |
| 2016/0331378 A1 | 11/2016 | Nitzan et al. |
| 2016/0354525 A1 | 12/2016 | Mcbride et al. |
| 2017/0007403 A1 | 1/2017 | Wildhirt et al. |
| 2017/0014562 A1 | 1/2017 | Liebing |
| 2017/0028115 A1 | 2/2017 | Muller |
| 2017/0035954 A1 | 2/2017 | Muller et al. |
| 2017/0049946 A1 | 2/2017 | Kapur et al. |
| 2017/0071769 A1 | 3/2017 | Mangiardi |
| 2017/0087286 A1 | 3/2017 | Spanier et al. |
| 2017/0087288 A1 | 3/2017 | Gross-Hardt et al. |
| 2017/0100527 A1 | 4/2017 | Schwammenthal et al. |
| 2017/0173237 A1 | 6/2017 | Pfeifer et al. |
| 2017/0197021 A1 | 7/2017 | Nitzan et al. |
| 2017/0215918 A1 | 8/2017 | Tao et al. |
| 2017/0232168 A1 | 8/2017 | Reichenbach et al. |
| 2017/0232171 A1 | 8/2017 | Roehn et al. |
| 2017/0290964 A1 | 10/2017 | Barry |
| 2017/0333067 A1 | 11/2017 | Wilson |
| 2017/0333607 A1 | 11/2017 | Zarins |
| 2017/0340787 A1 | 11/2017 | Corbett et al. |
| 2017/0340791 A1 | 11/2017 | Aboul-Hosn et al. |
| 2017/0348470 A1 | 12/2017 | D'Ambrosio et al. |
| 2018/0050142 A1 | 2/2018 | Siess et al. |
| 2018/0055979 A1 | 3/2018 | Corbett et al. |
| 2018/0064861 A1 | 3/2018 | Dur et al. |
| 2018/0080326 A1 | 3/2018 | Schumacher et al. |
| 2018/0100507 A1 | 4/2018 | Wu et al. |
| 2018/0104453 A1 | 4/2018 | Tao et al. |
| 2018/0149164 A1 | 5/2018 | Siess |
| 2018/0149165 A1 | 5/2018 | Siess et al. |
| 2018/0169312 A1 | 6/2018 | Barry |
| 2018/0169313 A1 | 6/2018 | Schwammenthal et al. |
| 2018/0207334 A1 | 7/2018 | Siess |
| 2018/0228952 A1 | 8/2018 | Pfeffer et al. |
| 2018/0228953 A1 | 8/2018 | Siess et al. |
| 2018/0264182 A1 | 9/2018 | Spanier et al. |
| 2018/0264183 A1 | 9/2018 | Jahangir |
| 2018/0280598 A1 | 10/2018 | Curran et al. |
| 2018/0289877 A1 | 10/2018 | Schumacher et al. |
| 2018/0303990 A1 | 10/2018 | Siess et al. |
| 2018/0303992 A1 | 10/2018 | Taskin |
| 2018/0303993 A1 | 10/2018 | Schwammenthal et al. |
| 2018/0353667 A1 | 12/2018 | Moyer et al. |
| 2019/0015570 A1 | 1/2019 | Muller |
| 2019/0030228 A1 | 1/2019 | Keenan et al. |
| 2019/0046702 A1 | 2/2019 | Siess et al. |
| 2019/0060539 A1 | 2/2019 | Siess et al. |
| 2019/0070345 A1 | 3/2019 | Mcbride et al. |
| 2019/0076167 A1 | 3/2019 | Fantuzzi et al. |
| 2019/0083690 A1 | 3/2019 | Siess et al. |
| 2019/0093769 A1 | 3/2019 | Lima Sarabanda et al. |
| 2019/0101130 A1 | 4/2019 | Bredenbreuker et al. |
| 2019/0105437 A1 | 4/2019 | Siess et al. |
| 2019/0117865 A1 | 4/2019 | Walters et al. |
| 2019/0134287 A1 | 5/2019 | Demou |
| 2019/0143018 A1 | 5/2019 | Salahieh et al. |
| 2019/0143019 A1 | 5/2019 | Mehaffey et al. |
| 2019/0170153 A1 | 6/2019 | Scheckel |
| 2019/0175802 A1 | 6/2019 | Tuval et al. |
| 2019/0175803 A1 | 6/2019 | Pfeffer et al. |
| 2019/0175805 A1 | 6/2019 | Tuval et al. |
| 2019/0175806 A1 | 6/2019 | Tuval et al. |
| 2019/0209753 A1 | 7/2019 | Tuval et al. |
| 2019/0209755 A1 | 7/2019 | Nix et al. |
| 2019/0209757 A1 | 7/2019 | Tuval et al. |
| 2019/0209758 A1 | 7/2019 | Tuval et al. |
| 2019/0211836 A1 | 7/2019 | Schumacher et al. |
| 2019/0216994 A1 | 7/2019 | Pfeffer et al. |
| 2019/0224391 A1 | 7/2019 | Liebing |
| 2019/0224392 A1 | 7/2019 | Pfeffer et al. |
| 2019/0224393 A1 | 7/2019 | Pfeffer et al. |
| 2019/0239998 A1 | 8/2019 | Tuval et al. |
| 2019/0262518 A1 | 8/2019 | Molteni et al. |
| 2019/0269840 A1 | 9/2019 | Tuval et al. |
| 2019/0275224 A1 | 9/2019 | Hanson et al. |
| 2019/0282741 A1 | 9/2019 | Franano et al. |
| 2019/0290817 A1 | 9/2019 | Guo et al. |
| 2019/0307561 A1 | 10/2019 | Gosal et al. |
| 2019/0316591 A1 | 10/2019 | Toellner |
| 2019/0321527 A1 | 10/2019 | King et al. |
| 2019/0321530 A1 | 10/2019 | Cambronne et al. |
| 2019/0321531 A1 | 10/2019 | Cambronne et al. |
| 2019/0328948 A1 | 10/2019 | Salahieh et al. |
| 2019/0336664 A1 | 11/2019 | Liebing |
| 2019/0344001 A1 | 11/2019 | Salahieh et al. |

(56) References Cited

U.S. PATENT DOCUMENTS

| | | |
|---|---|---|
| 2019/0351118 A1 | 11/2019 | Graichen et al. |
| 2019/0365975 A1 | 12/2019 | Muller et al. |
| 2020/0000542 A1 | 1/2020 | McFall et al. |
| 2020/0038567 A1 | 2/2020 | Siess et al. |
| 2020/0078506 A1 | 3/2020 | Schwammenthal et al. |
| 2020/0086022 A1 | 3/2020 | El Katerji et al. |
| 2020/0087199 A1 | 3/2020 | Gimblet |
| 2020/0093973 A1 | 3/2020 | Gandhi et al. |
| 2020/0114053 A1 | 4/2020 | Salahieh et al. |
| 2020/0155739 A1 | 5/2020 | Siess et al. |
| 2020/0197585 A1 | 6/2020 | Scheckel et al. |
| 2020/0237981 A1 | 7/2020 | Tuval et al. |
| 2020/0237982 A1 | 7/2020 | Tuval et al. |
| 2020/0237984 A1 | 7/2020 | Tuval et al. |
| 2020/0237985 A1 | 7/2020 | Tuval et al. |
| 2020/0237986 A1 | 7/2020 | Tuval et al. |
| 2020/0246527 A1 | 8/2020 | Hildebrand et al. |
| 2020/0268952 A1 | 8/2020 | Nitzan et al. |
| 2020/0276369 A1 | 9/2020 | Nitzan et al. |
| 2020/0288988 A1 | 9/2020 | Goldvasser |
| 2020/0376183 A1 | 12/2020 | El Katerji et al. |
| 2020/0405926 A1 | 12/2020 | Alexander et al. |
| 2021/0008261 A1 | 1/2021 | Calomeni et al. |
| 2021/0023285 A1 | 1/2021 | Brandt |
| 2021/0023286 A1 | 1/2021 | Tuval et al. |
| 2021/0038794 A1 | 2/2021 | Tuval |
| 2021/0069394 A1 | 3/2021 | Tuval et al. |
| 2021/0069395 A1 | 3/2021 | Tuval et al. |
| 2021/0077676 A1 | 3/2021 | Tuval et al. |
| 2021/0077692 A1 | 3/2021 | Tanner et al. |
| 2021/0121617 A1 | 4/2021 | Harjes et al. |
| 2021/0145475 A1 | 5/2021 | Tao et al. |
| 2021/0162199 A1 | 6/2021 | Tuval |
| 2021/0170081 A1 | 6/2021 | Kanz |
| 2021/0178145 A1 | 6/2021 | Tuval et al. |
| 2021/0213273 A1 | 7/2021 | Spanier et al. |
| 2021/0236797 A1 | 8/2021 | D'Ambrosio et al. |
| 2021/0260361 A1 | 8/2021 | Charafeddine et al. |
| 2021/0299433 A1 | 9/2021 | Siess et al. |
| 2022/0072297 A1 | 3/2022 | Tuval et al. |
| 2022/0079457 A1 | 3/2022 | Tuval et al. |
| 2022/0088368 A1 | 3/2022 | Tuval et al. |
| 2022/0134085 A1 | 5/2022 | Siess et al. |
| 2022/0161019 A1 | 5/2022 | Mitze et al. |
| 2022/0184376 A1 | 6/2022 | Tuval et al. |
| 2022/0226632 A1 | 7/2022 | Tuval et al. |
| 2022/0249830 A1 | 8/2022 | Kanz |
| 2022/0313980 A1 | 10/2022 | Hildebrand et al. |
| 2022/0355096 A1 | 11/2022 | Tuval et al. |
| 2023/0052997 A1 | 2/2023 | Skrzypczak et al. |
| 2023/0071248 A1 | 3/2023 | Keenan et al. |
| 2023/0137473 A1 | 5/2023 | Zipory et al. |
| 2023/0226342 A1 | 7/2023 | Tuval et al. |
| 2023/0390545 A1 | 12/2023 | D'Ambrosio et al. |
| 2024/0277997 A1 | 8/2024 | Tuval et al. |

FOREIGN PATENT DOCUMENTS

| | | | |
|---|---|---|---|
| CA | 2927346 A1 | 4/2009 | |
| CN | 101448535 A | 6/2009 | |
| CN | 101820933 | 9/2010 | |
| CN | 101854964 A | 10/2010 | |
| CN | 102365105 A | 2/2012 | |
| CN | 102805885 A | 12/2012 | |
| CN | 104185481 | 12/2014 | |
| CN | 104703532 A | 6/2015 | |
| CN | 105214153 | 1/2016 | |
| CN | 105682602 A | 6/2016 | |
| CN | 107050544 A | 8/2017 | |
| CN | 107137796 | 9/2017 | |
| CN | 109069716 A | 12/2018 | |
| CN | 109821085 | 5/2019 | |
| CN | 113457006 A | 10/2021 | |
| CN | 114259646 A | 4/2022 | |
| CN | 116036463 A | 5/2023 | |
| CN | 116328174 A | 6/2023 | |
| CN | 116474257 A | 7/2023 | |
| CN | 116867541 | 10/2023 | |
| DE | 1033690 B | 7/1958 | |
| DE | 10336902 B3 | 8/2004 | |
| EP | 0228787 A1 | 7/1987 | |
| EP | 0256683 A2 | 2/1988 | |
| EP | 0807447 A1 | 11/1997 | |
| EP | 916359 A1 | 5/1999 | |
| EP | 1339443 A1 | 9/2003 | |
| EP | 1651290 A1 | 5/2006 | |
| EP | 1827531 A1 | 9/2007 | |
| EP | 1871441 A2 | 1/2008 | |
| EP | 2047872 A1 | 4/2009 | |
| EP | 2047873 A1 | 4/2009 | |
| EP | 2217300 A1 | 8/2010 | |
| EP | 2218469 A1 | 8/2010 | |
| EP | 2234658 A2 | 10/2010 | |
| EP | 2282070 A1 | 2/2011 | |
| EP | 2298374 A1 | 3/2011 | |
| EP | 2299119 A1 | 3/2011 | |
| EP | 2301598 A1 | 3/2011 | |
| EP | 2308524 A1 | 4/2011 | |
| EP | 2314331 A1 | 4/2011 | |
| EP | 2345440 A1 | 7/2011 | |
| EP | 2366412 A2 | 9/2011 | |
| EP | 2376788 A1 | 10/2011 | |
| EP | 2408489 A1 | 1/2012 | |
| EP | 2424587 A1 | 3/2012 | |
| EP | 2475415 A1 | 7/2012 | |
| EP | 2607712 A1 | 6/2013 | |
| EP | 2040639 B1 | 2/2014 | |
| EP | 1207934 B1 | 8/2014 | |
| EP | 2662099 B1 | 9/2014 | |
| EP | 2427230 B1 | 12/2014 | |
| EP | 2396050 B1 | 1/2015 | |
| EP | 2835141 A1 | 2/2015 | |
| EP | 2840954 A1 | 3/2015 | |
| EP | 2841122 A1 | 3/2015 | |
| EP | 2841124 A1 | 3/2015 | |
| EP | 2860849 A1 | 4/2015 | |
| EP | 2868331 A2 | 5/2015 | |
| EP | 2868332 A1 | 5/2015 | |
| EP | 2999496 A2 | 3/2016 | |
| EP | 3000492 A1 | 3/2016 | |
| EP | 3000493 A1 | 3/2016 | |
| EP | 3055922 A1 | 8/2016 | |
| EP | 3062730 A1 | 9/2016 | |
| EP | 3115070 A1 | 1/2017 | |
| EP | 3127562 A1 | 2/2017 | |
| EP | 2922486 B1 | 5/2017 | |
| EP | 3216467 A1 | 9/2017 | |
| EP | 3222302 A1 | 9/2017 | |
| EP | 3236079 A1 | 10/2017 | |
| EP | 3287154 A1 | 2/2018 | |
| EP | 3287155 A1 | 2/2018 | |
| EP | 3326567 A1 | 5/2018 | |
| EP | 3329951 A1 | 6/2018 | |
| EP | 3338825 A1 | 6/2018 | |
| EP | 3205360 B1 | 8/2018 | |
| EP | 3359214 A1 | 8/2018 | |
| EP | 3359215 A1 | 8/2018 | |
| EP | 3398624 A1 | 11/2018 | |
| EP | 3398625 A1 | 11/2018 | |
| EP | 3407930 A1 | 12/2018 | |
| EP | 3446729 A1 | 2/2019 | |
| EP | 3446730 A1 | 2/2019 | |
| EP | 3545983 A1 | 10/2019 | |
| EP | 3606575 A1 | 2/2020 | |
| EP | 3737436 A1 | 11/2020 | |
| EP | 3848089 A1 | 7/2021 | |
| EP | 3858421 A1 | 8/2021 | |
| EP | 3897814 A1 | 10/2021 | |
| EP | 4218899 A1 | 8/2023 | |
| EP | 4252825 A2 | 10/2023 | |
| GB | 2239675 A | 7/1991 | |
| GB | 2451161 A | 1/2009 | |
| GB | 2504175 A | 1/2014 | |
| GB | 2504177 A | 1/2014 | |

(56) References Cited

FOREIGN PATENT DOCUMENTS

| | | | |
|---|---|---|---|
| JP | 2003504091 | A | 2/2003 |
| JP | 2004202006 | A | 7/2004 |
| JP | 2009530041 | A | 8/2009 |
| JP | 2012505038 | A | 3/2012 |
| JP | 2012527269 | A | 11/2012 |
| JP | 2015500666 | A | 1/2015 |
| JP | 2015516267 | A | 6/2015 |
| JP | 2016509950 | A | 4/2016 |
| JP | 2018535727 | A | 12/2018 |
| JP | 2020503083 | A | 1/2020 |
| WO | 9001972 | A1 | 3/1990 |
| WO | 90/13321 | | 11/1990 |
| WO | 1994/01148 | A1 | 1/1994 |
| WO | 99/34847 | | 7/1999 |
| WO | 2001/083016 | A2 | 5/2000 |
| WO | 2000043053 | A1 | 7/2000 |
| WO | 0062838 | A2 | 10/2000 |
| WO | 2002/070039 | A2 | 3/2001 |
| WO | 2002/038085 | | 5/2002 |
| WO | 03/006096 | | 1/2003 |
| WO | 03103745 | A2 | 12/2003 |
| WO | 2004073796 | A2 | 9/2004 |
| WO | 2005020848 | A2 | 3/2005 |
| WO | 2007081818 | A2 | 7/2007 |
| WO | 2007112033 | A2 | 10/2007 |
| WO | 2007127477 | A2 | 11/2007 |
| WO | 2008005747 | A2 | 1/2008 |
| WO | 2008005990 | A2 | 1/2008 |
| WO | 2008055301 | A1 | 5/2008 |
| WO | 2008104858 | A2 | 9/2008 |
| WO | 2009010963 | A2 | 1/2009 |
| WO | 2009046096 | A1 | 4/2009 |
| WO | 2009046790 | | 4/2009 |
| WO | 2009064879 | A2 | 5/2009 |
| WO | 2009129481 | A1 | 10/2009 |
| WO | 2010042546 | | 4/2010 |
| WO | 2010063494 | A1 | 6/2010 |
| WO | 2010105854 | A1 | 9/2010 |
| WO | 2010127871 | A1 | 11/2010 |
| WO | 2010133567 | A1 | 11/2010 |
| WO | 2010150208 | A2 | 12/2010 |
| WO | 2011035926 | A1 | 3/2011 |
| WO | 2011047884 | A1 | 4/2011 |
| WO | 2011076441 | A1 | 6/2011 |
| WO | 2011089022 | A1 | 7/2011 |
| WO | 2011160858 | A1 | 12/2011 |
| WO | 2012007141 | A1 | 1/2012 |
| WO | 2012094535 | A2 | 7/2012 |
| WO | 2013032849 | A1 | 3/2013 |
| WO | 2013070186 | A1 | 5/2013 |
| WO | 2013093001 | A2 | 6/2013 |
| WO | 20013119752 | | 8/2013 |
| WO | 2013148697 | A1 | 10/2013 |
| WO | 2013173239 | A1 | 11/2013 |
| WO | 2013183060 | A2 | 12/2013 |
| WO | 2014063119 | A1 | 4/2014 |
| WO | 2014141284 | A2 | 9/2014 |
| WO | 2014164292 | A1 | 10/2014 |
| WO | 2015063277 | A2 | 5/2015 |
| WO | 2015160943 | A1 | 10/2015 |
| WO | 2015177793 | A2 | 11/2015 |
| WO | 2016001218 | A1 | 1/2016 |
| WO | 2016005803 | A2 | 1/2016 |
| WO | 2016185473 | A1 | 11/2016 |
| WO | 2016207293 | A1 | 12/2016 |
| WO | 2017032751 | | 3/2017 |
| WO | 2017053361 | A1 | 3/2017 |
| WO | 2017060254 | A1 | 4/2017 |
| WO | 2017081561 | A1 | 5/2017 |
| WO | 2017137604 | A1 | 8/2017 |
| WO | 2017147291 | A1 | 8/2017 |
| WO | 2017159849 | A1 | 9/2017 |
| WO | 2017162618 | A1 | 9/2017 |
| WO | 2018033920 | A1 | 2/2018 |
| WO | 2018045299 | A1 | 3/2018 |
| WO | 2018061001 | A2 | 4/2018 |
| WO | 2018061002 | A1 | 4/2018 |
| WO | 2018067410 | A1 | 4/2018 |
| WO | 2018078615 | A1 | 5/2018 |
| WO | 2018096531 | A1 | 5/2018 |
| WO | 2018158636 | A1 | 9/2018 |
| WO | 2018172848 | A2 | 9/2018 |
| WO | 2018220589 | A1 | 12/2018 |
| WO | 2018226991 | A1 | 12/2018 |
| WO | 2018234454 | A1 | 12/2018 |
| WO | 2019094963 | A1 | 5/2019 |
| WO | 2019125899 | A1 | 6/2019 |
| WO | 2019138350 | A2 | 7/2019 |
| WO | 2019152875 | A1 | 8/2019 |
| WO | 2019158996 | A1 | 8/2019 |
| WO | 2019229223 | A1 | 12/2019 |
| WO | 2020152611 | A2 | 7/2020 |
| WO | 2021062265 | A1 | 4/2021 |
| WO | 2021152012 | A1 | 8/2021 |
| WO | 2021159147 | A1 | 8/2021 |
| WO | 2021198881 | A1 | 10/2021 |
| WO | 2021205346 | A2 | 10/2021 |
| WO | 2022189932 | A1 | 9/2022 |
| WO | 2023014742 | A1 | 2/2023 |
| WO | 2023062453 | A1 | 4/2023 |
| WO | 2024057252 | A1 | 3/2024 |
| WO | 2024057253 | A2 | 3/2024 |
| WO | 2024057254 | A1 | 3/2024 |
| WO | 2024057255 | A2 | 3/2024 |
| WO | 2024057256 | A2 | 3/2024 |
| WO | 2024057257 | A2 | 3/2024 |

OTHER PUBLICATIONS

Corrected Notice of Allowance for U.S. Appl. No. 17/077,769 mailed Nov. 15, 2023.
Corrected Notice of Allowance for U.S. Appl. No. 17/077,769 mailed Nov. 6, 2023.
Examination Report for Australian Patent Application No. 2019206421 mailed Sep. 29, 2023.
Extended Search Report for European Application No. 23189145.8 mailed Nov. 27, 2023.
Extended Search Report for European Application No. 23189147.4 mailed Dec. 13, 2023.
Extended Search Report for European Application No. 23189148.2 mailed Dec. 13, 2023.
Extended Search Report for European Application No. 23189149.0 mailed Dec. 13, 2023.
Final Office Action for U.S. Appl. No. 17/078,472 mailed Oct. 23, 2023.
Final Office Action for U.S. Appl. No. 17/574,701 mailed Feb. 8, 2024.
Hearing Notice for Indian Patent Application No. 201917018651 mailed Dec. 11, 2023.
Issue Notification for U.S. Appl. No. 16/275,559 mailed Nov. 22, 2023.
Issue Notification for U.S. Appl. No. 17/070,323 mailed Oct. 18, 2023.
Issue Notification for U.S. Appl. No. 17/077,769 mailed Nov. 29, 2023.
Issue Notification for U.S. Appl. No. 17/180,041 mailed Oct. 18, 2023.
Non-Final Office Action for U.S. Appl. No. 16/952,327 mailed Oct. 13, 2023.
Non-Final Office Action for U.S. Appl. No. 17/070,670 mailed Oct. 30, 2023.
Non-Final Office Action for U.S. Appl. No. 17/176,344 mailed Oct. 31, 2023.
Non-Final Office Action for U.S. Appl. No. 17/528,807 mailed Jan. 12, 2024.
Notice of Allowance for U.S. Appl. No. 16/952,389 mailed Feb. 7, 2024.
Notice of Allowance for U.S. Appl. No. 17/078,439 mailed Dec. 5, 2023.

(56) References Cited

OTHER PUBLICATIONS

Notice of Allowance for U.S. Appl. No. 17/173,944 mailed Nov. 8, 2023.
Notice of Allowance for U.S. Appl. No. 17/177,296 mailed Nov. 17, 2023.
Office Action for Canadian Application No. 3,176,272 mailed Jan. 2, 2024.
Office Action for Chinese Application No. 202080017728.9 mailed Nov. 6, 2023.
Office Action for Japanese Application No. 2021-533242 mailed Nov. 8, 2023.
U.S. Appl. No. 18/511,532, filed Nov. 16, 2023.
Corrected Notice of Allowability for U.S. Appl. No. 16/279,352 mailed Nov. 3, 2021.
Corrected Notice of Allowability for U.S. Appl. No. 16/281,237 mailed Mar. 31, 2021.
Corrected Notice of Allowability for U.S. Appl. No. 16/810,121 mailed Jun. 28, 2022.
Corrected Notice of Allowability for U.S. Appl. No. 16/810,121 mailed Sep. 20, 2022.
Corrected Notice of Allowability for U.S. Appl. No. 16/810,172 mailed Feb. 2, 2022.
Corrected Notice of Allowability for U.S. Appl. No. 17/182,482 mailed Feb. 7, 2023.
Examination Report for Australian Patent Application No. 2017349920 mailed Jun. 2, 2022.
Examination Report for Australian Patent Application No. 2017349920 mailed Nov. 4, 2022.
Examination Report for Indian Patent Application No. 201917018651 mailed Jun. 30, 2021.
Examination Report for Indian Patent Application No. 202047017397 mailed May 4, 2022.
Extended Search Report for European Application No. 19172327.9 mailed Aug. 23, 2019.
Extended Search Report for European Application No. 20159714.3 mailed Jul. 3, 2020.
Extended Search Report for European Application No. 20159716.8 mailed Jul. 3, 2020.
Extended Search Report for European Application No. 20159718.4 mailed Jul. 9, 2020.
Extended Search Report for European Application No. 20195082.1 mailed Nov. 5, 2020.
Extended Search Report for European Application No. 20195084.7 mailed Nov. 5, 2020.
Extended Search Report for European Application No. 20195085.4 mailed Nov. 4, 2020.
Extended Search Report for European Application No. 20195987.1 mailed Nov. 5, 2020.
Extended Search Report for European Application No. 21156647.6 mailed May 21, 2021.
Extended Search Report for European Application No. 21158196.2 mailed Apr. 8, 2021.
Extended Search Report for European Application No. 21158902.3 mailed Apr. 29, 2021.
Extended Search Report for European Application No. 21158903.1 mailed Apr. 9, 2021.
Extended Search Report for European Application No. 21208803.3 mailed Apr. 13, 2022.
Extended Search Report for European Application No. 21209256.3 mailed Mar. 2, 2022.
Extended Search Report for European Application No. 22155936.2 mailed Jul. 8, 2022.
Extended Search Report for European Application No. 22163640.0 mailed Jun. 29, 2022.
Extended Search Report for European Application No. 22163648.3 mailed Aug. 10, 2022.
Extended Search Report for European Application No. 22163653.3 mailed Jul. 1, 2022.
Final Office Action for U.S. Appl. No. 16/275,559 mailed Jan. 4, 2021.

Final Office Action for U.S. Appl. No. 16/275,559 mailed May 17, 2022.
Final Office Action for U.S. Appl. No. 16/275,559 mailed Oct. 20, 2021.
Final Office Action for U.S. Appl. No. 16/276,965 mailed Apr. 13, 2021.
Final Office Action for U.S. Appl. No. 16/277,411 mailed Jun. 21, 2021.
Final Office Action for U.S. Appl. No. 16/279,352 mailed May 3, 2021.
Final Office Action for U.S. Appl. No. 17/069,064 mailed May 25, 2022.
Final Office Action for U.S. Appl. No. 17/176,344 mailed Oct. 12, 2022.
International Search Report and Written Opinion from International Application No. PCT/IB2020/050515 mailed Sep. 9, 2020.
International Search Report and Written Opinion from International Application No. PCT/IB2021/052590 mailed Sep. 14, 2021.
International Search Report and Written Opinion from International Application No. PCT/IB2021/052857 mailed Oct. 5, 2021.
International Search Report and Written Opinion from International Application No. PCT/IB2022/051990 mailed Aug. 10, 2022.
International Search Report and Written Opinion from International Application No. PCT/IL2017/051158 mailed Jan. 17, 2018.
International Search Report and Written Opinion from International Application No. PT/IB2019/050186 mailed Jul. 18, 2019.
Invitation to Pay Additional Fees for International Application No. PCT/IB2020/050515 mailed Mar. 31, 2020.
Invitation to Pay Additional Fees for International Application No. PCT/IB2021/052590 mailed Jul. 23, 2021.
Invitation to Pay Additional Fees for International Application No. PCT/IB2021/052857 mailed Jul. 7, 2021.
Invitation to Pay Additional Fees for International Application No. PCT/IB2022/051990 mailed May 13, 2022.
Issue Notification for U.S. Appl. No. 16/276,965 mailed Mar. 16, 2022.
Issue Notification for U.S. Appl. No. 16/277,411 mailed Feb. 9, 2022.
Issue Notification for U.S. Appl. No. 16/278,482 mailed Jan. 13, 2021.
Issue Notification for U.S. Appl. No. 16/279,352 mailed Nov. 10, 2021.
Issue Notification for U.S. Appl. No. 16/280,566 mailed Nov. 10, 2021.
Issue Notification for U.S. Appl. No. 16/281,237 mailed Apr. 14, 2021.
Issue Notification for U.S. Appl. No. 16/281,264 mailed Dec. 16, 2020.
Issue Notification for U.S. Appl. No. 16/750,354 mailed Nov. 17, 2021.
Issue Notification for U.S. Appl. No. 16/810,086 mailed Mar. 9, 2022.
Issue Notification for U.S. Appl. No. 16/810,172 mailed Mar. 23, 2022.
Issue Notification for U.S. Appl. No. 16/810,270 mailed Oct. 12, 2022.
Issue Notification for U.S. Appl. No. 17/069,321 mailed Mar. 16, 2022.
Non-Final Office Action for U.S. Appl. No. 16/275,559 mailed Jan. 19, 2023.
Non-Final Office Action for U.S. Appl. No. 16/275,559 mailed Jan. 26, 2022.
Non-Final Office Action for U.S. Appl. No. 16/275,559 mailed May 26, 2021.
Non-Final Office Action for U.S. Appl. No. 16/275,559 mailed Sep. 4, 2020.
Non-Final Office Action for U.S. Appl. No. 16/276,965 mailed Jul. 26, 2021.
Non-Final Office Action for U.S. Appl. No. 16/276,965 mailed Jun. 19, 2020.
Non-Final Office Action for U.S. Appl. No. 16/276,965 mailed Nov. 30, 2020.

(56) References Cited

OTHER PUBLICATIONS

Non-Final Office Action for U.S. Appl. No. 16/277,411 mailed Feb. 9, 2021.
Non-Final Office Action for U.S. Appl. No. 16/278,482 mailed Jun. 23, 2020.
Non-Final Office Action for U.S. Appl. No. 16/279,352 mailed Nov. 10, 2020.
Non-Final Office Action for U.S. Appl. No. 16/280,566 mailed Dec. 21, 2020.
Non-Final Office Action for U.S. Appl. No. 16/281,237 mailed Aug. 21, 2020.
Non-Final Office Action for U.S. Appl. No. 16/281,264 mailed Jun. 29, 2020.
Non-Final Office Action for U.S. Appl. No. 16/810,121 mailed Mar. 9, 2022.
Non-Final Office Action for U.S. Appl. No. 16/952,327 mailed Nov. 8, 2022.
Non-Final Office Action for U.S. Appl. No. 16/952,389 mailed Dec. 21, 2022.
Non-Final Office Action for U.S. Appl. No. 16/952,444 mailed Jan. 6, 2023.
Non-Final Office Action for U.S. Appl. No. 17/069,064 mailed Dec. 9, 2021.
Non-Final Office Action for U.S. Appl. No. 17/069,064 mailed Nov. 7, 2022.
Non-Final Office Action for U.S. Appl. No. 17/069,321 mailed Nov. 18, 2021.
Non-Final Office Action for U.S. Appl. No. 17/069,570 mailed Oct. 6, 2022.
Non-Final Office Action for U.S. Appl. No. 17/070,323 mailed Oct. 6, 2022.
Non-Final Office Action for U.S. Appl. No. 17/070,670 mailed Oct. 5, 2022.
Non-Final Office Action for U.S. Appl. No. 17/077,769 mailed Oct. 5, 2022.
Non-Final Office Action for U.S. Appl. No. 17/176,344 mailed Apr. 20, 2022.
Non-Final Office Action for U.S. Appl. No. 17/180,041 mailed Jan. 31, 2023.
Notice of Allowance for U.S. Appl. No. 16/276,965 mailed Jan. 26, 2022.
Notice of Allowance for U.S. Appl. No. 16/277,411 mailed Dec. 8, 2021.
Notice of Allowance for U.S. Appl. No. 16/278,482 mailed Dec. 2, 2020.
Notice of Allowance for U.S. Appl. No. 16/279,352 mailed Oct. 1, 2021.
Notice of Allowance for U.S. Appl. No. 16/280,566 mailed Aug. 31, 2021.
Notice of Allowance for U.S. Appl. No. 16/281,237 mailed Feb. 1, 2021.
Notice of Allowance for U.S. Appl. No. 16/281,264 mailed Nov. 12, 2020.
Notice of Allowance for U.S. Appl. No. 16/750,354 mailed Oct. 18, 2021.
Notice of Allowance for U.S. Appl. No. 16/810,086 mailed Jan. 7, 2022.
Notice of Allowance for U.S. Appl. No. 16/810,121 mailed Aug. 19, 2022.
Notice of Allowance for U.S. Appl. No. 16/810,121 mailed Jun. 1, 2022.
Notice of Allowance for U.S. Appl. No. 16/810,172 mailed Jan. 10, 2022.
Notice of Allowance for U.S. Appl. No. 16/810,270 mailed Apr. 14, 2022.
Notice of Allowance for U.S. Appl. No. 16/810,270 mailed Jul. 22, 2022.
Notice of Allowance for U.S. Appl. No. 17/069,321 mailed Feb. 2, 2022.

Notice of Allowance for U.S. Appl. No. 17/069,604 mailed Mar. 8, 2023.
Notice of Allowance for U.S. Appl. No. 17/182,482 mailed Jan. 5, 2023.
Notice of Allowance on U.S. Appl. No. 16/810,116 mailed Mar. 13, 2023.
Office Action for Chinese Application No. 201780066201.3 mailed Jun. 29, 2021.
Office Action for Japanese Application No. 2019-521643 mailed May 10, 2022.
Office Action for Japanese Application No. 2019-521643 mailed Oct. 27, 2022.
Office Action for Japanese Application No. 2019-521643 mailed Sep. 28, 2021.
Restriction Requirement for U.S. Appl. No. 16/275,559 mailed Jun. 2, 2020.
Restriction Requirement for U.S. Appl. No. 16/279,352 mailed Aug. 11, 2020.
Restriction Requirement for U.S. Appl. No. 16/280,566 mailed Aug. 11, 2020.
Restriction Requirement for U.S. Appl. No. 16/810,116 mailed Jun. 29, 2022.
Supplemental Notice of Allowability for U.S. Appl. No. 16/276,965 mailed Mar. 10, 2022.
Supplemental Notice of Allowability for U.S. Appl. No. 16/276,965 mailed Mar. 2, 2022.
Supplemental Notice of Allowability for U.S. Appl. No. 16/278,482 mailed Dec. 24, 2020.
Supplemental Notice of Allowability for U.S. Appl. No. 16/279,352 mailed Oct. 21, 2021.
Third Party Submission received during the prosecution of U.S. Appl. No. 17/078,439 on Sep. 28, 2022.
U.S. Appl. No. 14/567,439, filed Dec. 11, 2014.
U.S. Appl. No. 16/275,559, filed Feb. 14, 2019.
U.S. Appl. No. 16/276,965, filed Feb. 15, 2019.
U.S. Appl. No. 16/277,411, filed Feb. 15, 2019.
U.S. Appl. No. 16/278,482, filed Feb. 18, 2019.
U.S. Appl. No. 16/279,352, filed Feb. 19, 2019.
U.S. Appl. No. 16/280,566, filed Feb. 20, 2019.
U.S. Appl. No. 16/281,237, filed Feb. 21, 2019.
U.S. Appl. No. 16/281,264, filed Feb. 21, 2019.
U.S. Appl. No. 16/750,354, filed Jan. 23, 2020.
U.S. Appl. No. 16/810,086, filed Mar. 5, 2020.
U.S. Appl. No. 16/810,121, filed Mar. 5, 2020.
U.S. Appl. No. 16/952,327, filed Nov. 19, 2020.
U.S. Appl. No. 16/952,389, filed Nov. 19, 2020.
U.S. Appl. No. 16/952,444, filed Nov. 19, 2020.
U.S. Appl. No. 17/069,064, filed Oct. 13, 2020.
U.S. Appl. No. 17/069,321, filed Oct. 13, 2020.
U.S. Appl. No. 17/069,570, filed Oct. 13, 2020.
U.S. Appl. No. 17/070,323, filed Oct. 14, 2020.
U.S. Appl. No. 17/070,670, filed Oct. 14, 2020.
U.S. Appl. No. 17/077,769, filed Oct. 22, 2020.
U.S. Appl. No. 17/078,439, filed Oct. 23, 2020.
U.S. Appl. No. 17/078,472, filed Oct. 23, 2020.
U.S. Appl. No. 17/176,344, filed Feb. 16, 2021.
U.S. Appl. No. 17/177,296, filed Feb. 17, 2021.
U.S. Appl. No. 17/180,041, filed Feb. 19, 2021.
U.S. Appl. No. 17/182,482, filed Feb. 23, 2021.
U.S. Appl. No. 17/528,015, filed Nov. 16, 2021.
U.S. Appl. No. 17/528,807, filed Nov. 17, 2021.
U.S. Appl. No. 17/532,318, filed Nov. 22, 2021.
U.S. Appl. No. 17/574,701, filed Jan. 13, 2022.
U.S. Appl. No. 17/609,589, filed Nov. 8, 2021.
U.S. Appl. No. 17/677,571, filed Feb. 22, 2022.
U.S. Appl. No. 17/678,122, filed Feb. 23, 2022.
U.S. Appl. No. 17/857,402, filed Jul. 5, 2022.
U.S. Appl. No. 18/121,995, filed Mar. 15, 2023.
U.S. Appl. No. 61/656,244, filed Jun. 6, 2012.
U.S. Appl. No. 61/779,803, filed Mar. 13, 2013.
U.S. Appl. No. 61/914,470, filed Dec. 11, 2013.
U.S. Appl. No. 61/914,475, filed Dec. 11, 2013.
U.S. Appl. No. 62/000,192, filed May 19, 2014.

(56)                    References Cited

OTHER PUBLICATIONS

U.S. Appl. No. 62/162,881, filed May 18, 2015.
U.S. Appl. No. 62/401,403, filed Sep. 29, 2016.
U.S. Appl. No. 62/412,631, filed Oct. 25, 2016.
U.S. Appl. No. 62/425,814, filed Nov. 23, 2016.
U.S. Appl. No. 62/543,540, filed Aug. 10, 2017.
U.S. Appl. No. 62/615,538, filed Jan. 10, 2018.
U.S. Appl. No. 62/665,718, filed May 2, 2018.
U.S. Appl. No. 62/681,868, filed Jun. 7, 2018.
U.S. Appl. No. 62/727,605, filed Sep. 6, 2018.
U.S. Appl. No. 62/796,138, filed Jan. 24, 2019.
U.S. Appl. No. 62/851,716, filed May 23, 2019.
U.S. Appl. No. 62/870,821, filed Jul. 5, 2019.
U.S. Appl. No. 62/896,026, filed Sep. 5, 2019.
U.S. Appl. No. 63/003,955, filed Apr. 2, 2020.
U.S. Appl. No. 63/006,122, filed Apr. 7, 2020.
U.S. Appl. No. 63/114,136, filed Nov. 16, 2020.
U.S. Appl. No. 63/129,983, filed Dec. 23, 2020.
U.S. Appl. No. 63/158,708, filed Mar. 9, 2021.
U.S. Appl. No. 63/254,321, filed Oct. 11, 2021.
"Compendium of Technical and Scientific Information for the Hemopump Temporary Cardiac Assist System", Johnson & Johnson Interventional Systems, 1988, pp. 1-15.
"Tanslation of decision of Board 4 (Nullity Board) of the German Federal Patent Court re German patent 10336902", pronounced Nov. 15, 2016, and appendices to decision, 62 pages.
Achour , et al., "Mechanical Left Ventricular Unloading Prior to Reperfusion Reduces Infarct Size in a Canine Infarction Model", Catheterization and Cardiovascular Interventions 64, 2005, pp. 182-192.
Agarwal , et al., "Newer-generation ventricular assist devices.", Best Practice & Research Clinical Anaesthesiology, 2012, pp. 117-130.
Alba , et al., "The future is here: ventricular assist devices for the failing heart", Expert review of cardiovascular therapy, 2009, pp. 1067-1077.
Bai , et al., "A Split-Array, C-2C Switched-Capacitor Power Amplifier in 65 nm CMOS", IEEE Radio Frequency Integrated Circuits Symposium, 2017, pp. 336-339.
Burnett , et al., "Renal Interstitial Pressure And Sodium Excretion During Renal Vein Constriction", American Physiological Society, 1980, pp. F279-F282.
Butler , et al., "The Hemopump—A New Cardiac Prothesis Device", Reprinted from IEEE Transactions on Biomedical Engineering, vol. 37, No. 2, Feb. 1990, pp. 192-195.
Cassidy , et al., "The Conductance Volume Catheter Technique for Measurement of Left Ventricular Volume in Young Piglets", Pediatric Research, 1992, pp. 85-90.
Chan , et al., "Rapid manufacturing techniques in the development of an axial blood pump impeller", Proc. Instn Mech. Engrs vol. 217 Part H: J. Engineering in Medicine, 2003, pp. 469-475.
Coxworth , "Artificial Vein Valve Could Replace Drugs For Treating Common Circulatory Problem", Published on Gizmag website (http://www.gizmag.com/artificial-venous-valve-cvi/21785/), Mar. 9, 2012.
Damman , et al., "Decreased Cardiac Output, Venous Congestion And The Association With Renal Impairment In Patients With Cardiac Dysfunction", European Journal of Heart Failure, 2007, pp. 872-878.
Damman , et al., "Increased Central Venous Pressure Is Associated With Impaired Renal Function And Mortality In A Broad Spectrum Of Patients With Cardiovascular Disease", Journal of American College of Cardiology, 2009, pp. 582-588.
Dekker , et al., "Efficacy of a New Intraaortic Propeller Pump vs the Intraaortic Balloon Pump", Chest, vol. 123, Issue 6, Jun. 2003, pp. 2089-2095.
Doty , et al., "The Effect Of Increased Renal Venous Pressure On Renal Function", The Journal of Trauma,, Dec. 1999, pp. 1000-1003.

Felker , et al., "Anemia As A Risk Factor And Therapeutic Target In Heart Failure", Journal of the American College of Cardiology, 2004, pp. 959-966.
Firth , et al., "Raised Venous Pressure: A Direct Cause Of Sodium Retention In Oedema?", The Lancet, May 7, 1988, pp. 1033-1036.
Flameng , "Temporary Cardiac Assist with an Axial Pump System", Steinkopff Verlag Darmstadt, 1991, 79 pages.
Forman , et al., "Incidence, Predictors At Admission, And Impact Of Worsening Renal Function Among Patients Hospitalized With Heart Failure", Journal of American College of Cardiology, 2004, pp. 61-67.
Fraser , et al., "The use of computational fluid dynamics in the development of ventricular assist devices", Medical engineering & physics, 2011, pp. 263-280.
Frazier , et al., "First Human Use of the Hemopump, a Catheter Mounted Ventricular Assist Device", Ann Thorac Surg, 1990, pp. 299-304.
Frazier , et al., "Treatment of Cardiac Allograft Failure by use of an IntraAortic Axial Flow Pump", Journal of Heart Transplantation, St. Louis, vol. 9, No. 4, pp. 408-414, Jul. 1990.
Gomes , et al., "Heterologous Valve Implantation In The Infra-Renal Vena Cava For Treatment Of The Iliac Venous Valve Regurgitation Disease: Experimental Study", Rev Bras Cir Cardiovasc, 2002, pp. 367-369.
Gunther , et al., "Experimentelle Radiologie", Life Sciences, Berichte Aus Der Rheinischwestfälischen Technischen Hochschule Aachen Ausgabe Feb. 2002, 9 pages.
Haddy , et al., "Effect Of Elevation Of Intraluminal Pressure On Renal Vascular Resistance", Circulation Research Journal Of The American Heart Association, 1956, pp. 659-663.
Heywood , et al., "High Prevalence Of Renal Dysfunction And Its Impact On Outcome In 118,465 Patients Hospitalized With Acute Decompensated Heart Failure: A Report From The ADHERE Database", Journal of Cardiac Failure, 2007, pp. 422-430.
Hillege , et al., "Renal Function As A Predictor Of Outcome In A Broad Spectrum Of Patients With Heart Failure", Circulation Journal of the American Heart Association, 2006, pp. 671-678.
Hillege , et al., "Renal Function, Neurohormonal Activation, And Survival In Patients With Chronic Heart Failure", Circulation Journal of the American Heart Association, 2000, pp. 203-210.
Hsu , et al., "Review of recent patents on foldable ventricular assist devices", Recent Patents on Biomedical Engineering, 2012, pp. 208-222.
Ikari , "The Physics Of Guiding Catheter; The Ikari Guiding Catheter In TRI", available at httu:i /www.docstoc.com/docs/148136553/The-[KARI-catheter—anovel-guide-for-TRI—.
Kafagy , et al., "Design of axial blood pumps for patients with dysfunctional fontan physiology: computational studies and performance testing", Artificial organs, 2015, pp. 34-42.
Kang , et al., "Fluid dynamics aspects of miniaturized axial-flow blood pump", Bio-medical materials and engineering, 2014, pp. 723-729.
Koochaki , et al., "A new design and computational fluid dynamics study of an implantable axial blood pump", Australasian Physical & Engineering Sciences in Medicine, 2013, pp. 417-422.
Lauten , et al., "Heterotopic Transcatheter Tricuspid Valve Implantation: First-In-Man Application Of A Novel Approach To Tricuspid Regurgitation", European Heart Journal, Feb. 15, 2011, pp. 1207-1213.
Ledoux, et al., "Left Ventricular Unloading With Intra-aortic Counter Pulsation Prior to Reperfusion Reduces Myocardial Release of Endothelin-1 and Decreases Infarction Size in a Porcine Ischemia-Reperfusion Model", Catheterization and Cardiovascular Interventions 72, 2008, pp. 513-521.
McAlister , et al., "Renal Insufficiency And Heart Failure: Prognostic And Therapeutic Implications From A Prospective Cohort Study", Circulation Journal of the American Heart Association, 2004, pp. 1004-1009.
Merhige , et al., "Effect of the Hemopump Left Ventricular Assist Device on Regional Myocardial Perfusion and Function", Reduction of Ischemia during Coronary Occlusion, Johnson & Johnson Interventional Systems Supplement 3, Circulation vol. 80, No. 5, Nov. 1989, pp. III-159-III-166.

(56) References Cited

OTHER PUBLICATIONS

Meyns , et al., "The Heart-Hemopump Interaction: A Study of Hemopump Flow as a Function of Cardiac Activity", Artificial Organs, 1996, pp. 641-649.

Mullens , et al., "Elevated Intra-Abdominal Pressure In Acute Decompensated Heart Failure. A Potential Contributor To Worsening Renal Function", Journal of the American College of Cardiology, 2008, pp. 300-306.

Mullens , et al., "Importance Of Venous Congestion For Worsening Of Renal Function In Advanced Decompensated Heart Failure", Journal of American College of Cardiology, 2009, pp. 589-596.

Mullens , et al., "Prompt Reduction In Intra-Abdominal Pressure Following Large-Volume Mechanical Fluid Removal Improves Renal Insufficiency In Refractory Decompensated Heart Failure", Journal of Cardiac Failure, 2008, pp. 508-514.

Notarius , et al., "Central Venous Pressure During Exercise: Role Of Muscle Pump", Canadian Journal of Physiology and Pharmacology, 1996, pp. 647-651.

Park , et al., "Nutcracker Syndrome: Intravascular Stenting Approach", Nephrol Dial Transplant, 2000, pp. 99-101.

Reul , et al., "Blood pumps for circulatory support", Perfusion-Sevenoaks, 2000, pp. 295-312.

Reul , et al., "Rotary blood pumps in circulatory assist", Perfusion, May 1995, pp. 153-158.

Rodefeld , "Cavopulmonary assist for the univentricular Fontan circulation: von Karman viscous impeller pump", The Journal of Thoracic and Cardiovascular Surgery, 2010, pp. 529-536.

Roundtree , et al., "The Hemopump Cardiac Assist System: Nursing Care of the Patient", Reprinted from Critical Care Nurse, Apr. 1991.

Schmitz-Rode , et al., "An Expandable Percutaneous Catheter Pump For Left Ventricular Support", Journal of the American College of Cardiology, vol. 45, No. 11, 2005, pp. 1856-1861.

Schmitz-Rode , et al., "Axial flow catheter pump for circulatory support", Biomed Tech (Berl), 2002, pp. 142-143.

Scholz , et al., "MechanicaL left Ventricular Unloading During High Risk Coronary Angioplasty: First Use of a New Percutaneous Transvalvular Left Ventricular Assist Device", Catheterization and Cardiovascular Diagnosis 31, 1994, pp. 61-69.

Semple , et al., "Effect Of Increased Renal Venous Pressure On Circulatory "Autoregulation" Of Isolated Dog Kidneys", Circulation Research Journal of The American Heart Association, 1959, pp. 643-648.

Sianos , et al., "The Recover® LP 2.5 catheter-mounted left ventricular assist device", EuroIntervention, 2006, pp. 116-119.

Siess , et al., "Concept, realization, and first in vitro testing of an intraarterial microaxial blood pump", Artificial Organs, 1995, pp. 644-652.

Siess , et al., "Hemodynamic system analysis of intraarterial microaxial pumps in vitro and in vivo", Artificial Organs, Jun. 1996, pp. 650-661.

Siess , "PhD Chapter 3—English translation", https://www.shaker.eu/en/content/catalogue/index.asp?lang=en&ID=8&ISBN=978-3-8265-6150-4&search=yes.

Siess , "System Analysis and Development of Intravascular Rotation Pumps for Cardiac Assist", Helmholtz-Institute—Chapter 3, Jun. 1998, 17 pages.

Smalling , et al., "Improved Regional Myocardial Blood Flow, Left Ventricular Unloading, and Infarct Salvage Using an Axial-Flow, Transvalvular Left Ventricular Assist Device", A Comparison With Intra-Aortic Balloon Counterpulsation and Reperfusion Alone in a Canine Infarction Model, Presented in part at the American College of Cardiology 38th Annual Scientific Session, Mar. 1990, pp. 1152-1160.

Smalling , et al., "The Hemopump: A transvalvular, axial flow, left ventricular assist device", Coronary Artery Disease, Circulatory support devices in clinical cardiology, vol. 2 No. 6, pp. 666-671, Aug. 1991.

Smalling , et al., "Transvalvular Left Ventricular Assistance in Cardiogenic Shock Secondary to Acute Myocardial Infarction", Evidence for Recovery From Near Fatal Myocardial Stunning, JACC vol. 23, No. 3, pp. 637-644, Mar. 1, 1994.

Song , et al., "Axial flow blood pumps", ASAIO journal, 2003, pp. 355-364.

Tamareille , et al., "Left ventricular unloading before reperfusion reduces endothelin-1 release and calcium overload in porcine myocardial infarction", Cardiopulmonary Support and Physiology, The Journal of Thoracic and Cardiovascular Surgery, vol. 136, No. 2, 2008, pp. 343-351.

Tang , et al., "Anemia In Chronic Heart Failure: Prevalence, Etiology, Clinical Correlates, And Treatment Options", Circulation Journal of the American Heart Association, 2006, pp. 2454-2461.

Throckmorton , et al., "Design of a protective cage for an intra vascular axial flow blood pump to mechanically assist the failing Fontan", Artificial organs, 2009, pp. 611-621.

Throckmorton , et al., "Mechanical Cavopulmonary Assist for the Univentricular Fontan Circulation Using a Novel Folding Propeller Blood Pump", ASAIO Journal, 2007, pp. 734-741.

Thunberg , et al., "Ventricular assist devices today and tomorrow", Journal of cardiothoracic and vascular anesthesia, 2010, pp. 656-680.

Timms , "A review of clinical ventricular assist devices", Medical engineering & physics, 2011, pp. 1041-1047.

Triep , et al., "Computational Fluid Dynamics and Digital Particle Image Velocimetry Study of the Flow Through an Optimized Micro-axial Blood Pump", Artificial Organs, May 2006, pp. 384-391.

Uthoff , et al., "Central venous pressure at emergency room presentation predicts cardiac rehospitalization in patients with decompensated heart failure", European Journal of Heart Failure, 2010, pp. 469-476.

Van Mieghem , et al., "Design and Principle of Operation of the HeartMate PHPTM (Percutaneous Heart Pump)", EuroIntervention, 2016.

Vercaemst , et al., "Impella: A Miniaturized Cardiac Support System in an Era of Minimal Invasive Cardiac Surgery", Presented at the 39th International Conference of the American Society of Extra-Corporeal Technology, Mar. 22-25, 2001.

Wampler , "Newspaper Articles", Captain Hemo, 1988, 6 pages.

Wampler , "Newsweek", Captain Hemo, May 16, 1988, 3 pages.

Wampler , "The first co-axial flow pump for human use: the Hemopump", Flameng W. (eds) Temporary Cardiac Assist with an Axial Pump System, 1991.

Wampler , "THI Today", Captain Hemo, Summer 1988, 2 pages.

Wampler , "Time Magazine", Captain Hemo, May 1988, 2 pages.

Wampler , et al., "Treatment of Cardiogenic Shock With the Hemopump Left Ventricular Assist Device", Annual of Thoracic Surgery, vol. 52, pp. 560-513, 1991.

Wampler , "U.S. News & World Report", Captain Hemo, pp. 1-2, May 16, 1988.

Wencker , "Acute Cardio-Renal Syndrome: Progression From Congestive Heart Failure To Congestive Kidney Failure", Current Heart Failure Reports, 2007, pp. 134-138.

Winton , "The Control Of Glomerular Pressure By Vascular Changes Within The Mammalian Kidney, Demonstrated By The Actions Of Adrenaline", Journal of Physiology, Nov. 1931, pp. 151-162.

Winton , "The Influence Of Venous Pressure On The Isolated Mammalian Kidney", Journal of Physiology, Jun. 6, 1931, pp. 49-61.

Wood , "The Mechanism Of The Increased Venous Pressure With Exercise In Congestive Heart Failure", Journal of Clinical Investigation, 1962, pp. 2020-2024.

Wu , et al., "Design and simulation of axial flow maglev blood pump", International Journal of Information Engineering and Electronic Business, 2011, p. 42.

Yancy , et al., "Clinical Presentation, Management, And In-Hospital Outcomes Of Patients Admitted With Acute Decompensated Heart Failure With Preserved Systolic Function. A Report From The Acute Decompensated Heart Failure National Registry (ADHERE) Database", Journal of the American College of Cardiology, 2006, pp. 76-84.

Corrected Notice of Allowability for U.S. Appl. No. 16/810,116 mailed Apr. 7, 2023.

(56) References Cited

OTHER PUBLICATIONS

Corrected Notice of Allowability for U.S. Appl. No. 17/070,323 mailed Jun. 1, 2023.
Corrected Notice of Allowability for U.S. Appl. No. 17/180,041 mailed Jun. 30, 2023.
Corrected Notice of Allowance for U.S. Appl. No. 17/070,323 mailed Oct. 4, 2023.
Corrected Notice of Allowance for U.S. Appl. No. 17/077,769 mailed Oct. 4, 2023.
Corrected Notice of Allowance for U.S. Appl. No. 17/180,041 mailed Oct. 4, 2023.
Examination Report for Indian Patent Application No. 202147033522 mailed May 24, 2023.
Extended Search Report and Preliminary Opinion for European Application No. 23159720.4 mailed Jun. 27, 2023.
Extended Search Report for European Application No. 22197511.3 mailed Dec. 5, 2022.
Extended Search Report for European Application No. 23159721.2 mailed Jun. 26, 2023.
Extended Search Report for European Application No. 23159724.6 mailed Jun. 26, 2023.
Extended Search Report for European Application No. 23159725.3 mailed Jun. 28, 2023.
Final Office Action for U.S. Appl. No. 16/952,327 mailed Jun. 8, 2023.
Final Office Action for U.S. Appl. No. 16/952,389 mailed Jul. 18, 2023.
Final Office Action for U.S. Appl. No. 16/952,444 mailed Jul. 5, 2023.
Final Office Action for U.S. Appl. No. 17/069,570 mailed Apr. 28, 2023.
Final Office Action for U.S. Appl. No. 17/070,670 mailed Jun. 2, 2023.
Final Office Action for U.S. Appl. No. 17/077,769 mailed Jun. 7, 2023.
International Search Report and Written Opinion from International Application No. PCT/IB2022/058101 mailed Feb. 20, 2023.
Issue Notification for U.S. Appl. No. 16/810,116 mailed May 17, 2023.
Non-Final Office Action for U.S. Appl. No. 17/069,570 mailed Oct. 2, 2023.
Non-Final Office Action for U.S. Appl. No. 17/078,439 mailed Jun. 1, 2023.
Non-Final Office Action for U.S. Appl. No. 17/078,472 mailed May 4, 2023.
Non-Final Office Action for U.S. Appl. No. 17/574,701 mailed Sep. 27, 2023.
Notice of Allowance for U.S. Appl. No. 16/275,559 mailed Jul. 27, 2023.
Notice of Allowance for U.S. Appl. No. 16/275,559 mailed Oct. 4, 2023.
Notice of Allowance for U.S. Appl. No. 17/070,323 mailed Aug. 30, 2023.
Notice of Allowance for U.S. Appl. No. 17/070,323 mailed May 15, 2023.
Notice of Allowance for U.S. Appl. No. 17/077,769 mailed Sep. 27, 2023.
Notice of Allowance for U.S. Appl. No. 17/173,944 mailed Jul. 10, 2023.
Notice of Allowance for U.S. Appl. No. 17/180,041 mailed Jun. 13, 2023.
Notice of Allowance for U.S. Appl. No. 17/180,041 mailed Sep. 18, 2023.
Notice of Allowance for U.S. Appl. No. 17/182,482 mailed Apr. 21, 2023.
Office Action for Canadian Application No. 3,039,285 mailed Mar. 24, 2023.
Office Action for Canadian Application No. 3,080,800 mailed Sep. 12, 2023.
Office Action for Canadian Application No. 3,122,415 mailed Mar. 31, 2023.
Office Action for Chinese Application No. 201980007116.9 mailed Nov. 28, 2022.
Office Action for Japanese Application No. 2019-521643 mailed Apr. 11, 2023.
Office Action for Japanese Application No. 2020-537746 mailed Feb. 21, 2023.
U.S. Appl. No. 18/122,486, filed Mar. 16, 2023.
U.S. Appl. No. 18/122,504, filed Mar. 16, 2023.
U.S. Appl. No. 18/447,025, filed Aug. 9, 2023.
U.S. Appl. No. 18/447,050, filed Aug. 9, 2023.
U.S. Appl. No. 18/447,064, filed Aug. 9, 2023.
U.S. Appl. No. 18/447,074, filed Aug. 9, 2023.
U.S. Appl. No. 18/447,086, filed Aug. 9, 2023.
U.S. Appl. No. 63/317,199, filed Mar. 7, 2022.
Corrected Notice of Allowance for U.S. Appl. No. 16/952,389 mailed Feb. 20, 2024.
Corrected Notice of Allowance for U.S. Appl. No. 16/952,389 mailed Mar. 4, 2024.
Corrected Notice of Allowance for U.S. Appl. No. 16/952,444 mailed Mar. 13, 2024.
Corrected Notice of Allowance for U.S. Appl. No. 17/069,570 mailed Apr. 10, 2024.
Corrected Notice of Allowance for U.S. Appl. No. 17/069,570 mailed Jul. 16, 2024.
Examination Report for European Application No. 21158196.2 mailed May 28, 2024.
Examination Report for European Application No. 21158903.1 mailed Jul. 9, 2024.
Examination Report for European Application No. 21718229.4 mailed Mar. 17, 2022.
Extended Search Report for European Application No. 24170573.0 mailed Jul. 29, 2024.
Final Office Action for U.S. Appl. No. 17/078,472 mailed Aug. 9, 2024.
Final Office Action for U.S. Appl. No. 17/176,344 mailed Apr. 12, 2024.
Final Office Action for U.S. Appl. No. 17/528,807 mailed Apr. 24, 2024.
Hearing Notice for Indian Application No. 202147033522 mailed Jul. 24, 2024.
International Search Report and Written Opinion from International Application No. PCT/IB2023/059136 mailed Jan. 2, 2024.
International Search Report and Written Opinion from International Application No. PCT/IB2023/059137 mailed Mar. 21, 2024.
International Search Report and Written Opinion from International Application No. PCT/IB2023/059138 mailed Feb. 7, 2024.
International Search Report and Written Opinion from International Application No. PCT/IB2023/059141 mailed Mar. 22, 2024.
International Search Report and Written Opinion from International Application No. PCT/IB2023/059142 mailed Apr. 16, 2024.
International Search Report and Written Opinion from International Application No. PCT/IB2023/059143 mailed Mar. 14, 2024.
Invitation to Pay Additional Fees for International Application No. PCT/IB2023/059134 mailed Dec. 21, 2023.
Invitation to Pay Additional Fees for International Application No. PCT/IB2023/059137 mailed Jan. 2, 2024.
Invitation to Pay Additional Fees for International Application No. PCT/IB2023/059138 mailed Dec. 8, 2023.
Invitation to Pay Additional Fees for International Application No. PCT/IB2023/059141 mailed Dec. 22, 2023.
Invitation to Pay Additional Fees for International Application No. PCT/IB2023/059142 mailed Jan. 2, 2024.
Issue Notification for U.S. Appl. No. 16/952,389 mailed Mar. 13, 2024.
Issue Notification for U.S. Appl. No. 16/952,444 mailed Mar. 20, 2024.
Issue Notification for U.S. Appl. No. 17,574,701 mailed Aug. 28, 2024.
Issue Notification for U.S. Appl. No. 17/078,439 mailed Apr. 3, 2024.

(56)     References Cited

OTHER PUBLICATIONS

Issue Notification for U.S. Appl. No. 17/173,944 mailed Jun. 12, 2024.
Issue Notification for U.S. Appl. No. 17/177,296 mailed Mar. 13, 2024.
Non-Final Office Action for U.S. Appl. No. 17/078,472 mailed Feb. 14, 2024.
Non-Final Office Action for U.S. Appl. No. 17/532,318 mailed Jul. 18, 2024.
Non-Final Office Action for U.S. Appl. No. 17/609,589 mailed Jul. 1, 2024.
Non-Final Office Action for U.S. Appl. No. 17/677,571 mailed Aug. 15, 2024.
Non-Final Office Action for U.S. Appl. No. 17/682,073 mailed Aug. 29, 2024.
Non-Final Office Action for U.S. Appl. No. 18/511,532 mailed Aug. 27, 2024.
Notice of Allowance for U.S. Appl. No. 16/952,327 mailed Apr. 29, 2024.
Notice of Allowance for U.S. Appl. No. 16/952,327 mailed Aug. 6, 2024.
Notice of Allowance for U.S. Appl. No. 16/952,444 mailed Feb. 15, 2024.
Notice of Allowance for U.S. Appl. No. 17/069,570 mailed Jun. 24, 2024.
Notice of Allowance for U.S. Appl. No. 17/069,570 mailed Mar. 13, 2024.
Notice of Allowance for U.S. Appl. No. 17/070,670 mailed Jun. 13, 2024.
Notice of Allowance for U.S. Appl. No. 17/078,439 mailed Feb. 27, 2024.
Notice of Allowance for U.S. Appl. No. 17/173,944 mailed Mar. 6, 2024.
Notice of Allowance for U.S. Appl. No. 17/177,296 mailed Feb. 14, 2024.
Notice of Allowance for U.S. Appl. No. 17/528,807 mailed Sep. 9, 2024.
Notice of Allowance for U.S. Appl. No. 17/574,701 mailed Jun. 26, 2024.
Notice of Missing Requirements for U.S. Appl. No. 18/447,025 mailed Feb. 1, 2024.
Office Action for Japanese Application No. 2023-156391 mailed Jun. 3, 2024.
Restriction Requirement for U.S. Appl. No. 17/722,752 mailed Sep. 12, 2024.
Restriction Requirement for U.S. Appl. No. 17/723,150 mailed Sep. 11, 2024.
Restriction Requirement for U.S. Appl. No. 17/723,656 mailed Sep. 12, 2024.
U.S. Appl. No. 18/444,972, filed Feb. 19, 2024.
U.S. Appl. No. 18/632,533, filed Apr. 11, 2024.
U.S. Appl. No. 18/632,545, filed Apr. 11, 2024.
U.S. Appl. No. 18/632,557, filed Apr. 11, 2024.
U.S. Appl. No. 18/632,569, filed Apr. 11, 2024.
U.S. Appl. No. 18/635,275, filed Apr. 15, 2024.
U.S. Appl. No. 18/635,286, filed Apr. 15, 2024.
U.S. Appl. No. 18/635,292, filed Apr. 15, 2024.
U.S. Appl. No. 18/637,653, filed Apr. 17, 2024.
U.S. Appl. No. 18/637,655, filed Apr. 17, 2024.
U.S. Appl. No. 18/637,667, filed Apr. 17, 2024.
U.S. Appl. No. 18/639,079, filed Apr. 18, 2024.
U.S. Appl. No. 18/639,087, filed Apr. 18, 2024.
U.S. Appl. No. 18/639,094, filed Apr. 18, 2024.
U.S. Appl. No. 18/639,098, filed Apr. 18, 2024.
U.S. Appl. No. 18/640,222, filed Apr. 19, 2024.
U.S. Appl. No. 18/640,260, filed Apr. 19, 2024.
U.S. Appl. No. 18/640,285, filed Apr. 19, 2024.
U.S. Appl. No. 18/640,303, filed Apr. 19, 2024.
U.S. Appl. No. 18/652,930, filed May 2, 2024.
U.S. Appl. No. 18/652,956, filed May 2, 2024.

U.S. Appl. No. 18/652,959, filed May 2, 2024.
U.S. Appl. No. 18/652,962, filed May 2, 2024.
U.S. Appl. No. 18/654,336, filed May 3, 2024.
U.S. Appl. No. 18/882,984, filed Sep. 12, 2024.
U.S. Appl. No. 63/406,427, filed Sep. 14, 2022.
U.S. Appl. No. 63/432,496, filed Dec. 14, 2022.
U.S. Appl. No. 63/443,519, filed Feb. 6, 2023.
U.S. Appl. No. 63/470,259, filed Jun. 1, 2023.
"Peripheral Interventions 2015 Product Catalog", Boston Scientific, 2015, 7 pages.
Alsafarr, et al., "Hydrodynamic Effects on Flow Through Screens at Intakes", Water Research vol. 8, Issue 9, Sep. 1974, pp. 617-622.
Brückler, et al., "Flow Design and Optimization of a Percutaneously Implantable Miniature Blood Pump", Medical technology in cardiology, 2002, 11 pages.
Chang, et al., "Leveraging Device-Arterial Coupling to Determine Cardiac and Vascular State", IEEE Transactions on Biomedical Engineering, vol. 66, No. 10, Oct. 2019, pp. 2800-2808.
Fox, et al., "Introduction to Fluid Mechanics", Sixth Edition.
Kapur, et al., "Mechanical Left Ventricular Unloading to Reduce Infarct Size During Acute Myocardial Infarction: Insight from Preclinical and Clinical Studies", Journal of Cardiovascular Translational Research, Apr. 23, 2019, pp. 1-8.
Kaufman, "Invasive Vascular Diagnosis", Radiology Key Fastest Radiology Insight Engine, Chapter 3, Dec. 23, 2015, 12 pages.
Keller, et al., "Dynamic Modulation of Device-Arterial Coupling to Determine Cardiac Output and Vascular Resistance", Annals of Biomedical Engineering, vol. 48, No. 9, Sep. 2020, pp. 2333-2342.
Schmitz-Rode, "Percutaneously implantable, self-expanding left heart support pump", Clinic for Radiological Diagnostics, 2001, 19 Pages.
Siess, et al., "Basic Design Criteria for Rotary Blood Pumps", Rotary Blood Pumps, 2000, pp. 69-83.
Corrected Notice of Allowance for U.S. Appl. No. 16/952,327 mailed Sep. 20, 2024.
Corrected Notice of Allowance for U.S. Appl. No. 17/528,015 mailed Apr. 11, 2025.
Corrected Notice of Allowance for U.S. Appl. No. 17/528,015 mailed May 13, 2025.
Corrected Notice of Allowance for U.S. Appl. No. 17/528,807 mailed Sep. 19, 2024.
Corrected Notice of Allowance for U.S. Appl. No. 17/678,122 mailed May 27, 2025.
Corrected Notice of Allowance for U.S. Appl. No. 17/723,150 mailed Apr. 24, 2025.
Corrected Notice of Allowance for U.S. Appl. No. 17/857,402 mailed Nov. 7, 2024.
Examination Report for Australian Application No. 2024203274 mailed May 1, 2025.
Extended Search Report for European Application No. 24200871.2 mailed Jan. 30, 2025.
Extended Search Report for European Application No. 24200875.3 mailed Jan. 13, 2025.
Extended Search Report for European Application No. 24206716.3 mailed Nov. 21, 2024.
Extended Search Report for European Application No. 24209593.3 mailed Dec. 4, 2024.
Extended Search Report for European Application No. 24209594.1 mailed Dec. 4, 2024.
Extended Search Report for European Application No. 24211523.6 mailed Feb. 7, 2025.
Extended Search Report for European Application No. 24211525.1 mailed Feb. 20, 2025.
Extended Search Report for European Application No. 25151821.3 mailed Apr. 14, 2025.
Final Office Action for U.S. Appl. No. 17/078,472 mailed Mar. 12, 2025.
Final Office Action for U.S. Appl. No. 17/678,812 mailed May 28, 2025.
Final Office Action for U.S. Appl. No. 17/723,656 mailed Apr. 8, 2025.
Final Office Action for U.S. Appl. No. 18/511,532 mailed Apr. 11, 2025.

(56)          References Cited

OTHER PUBLICATIONS

International Search Report and Written Opinion for International Application No. PCT/IB2024/063113 mailed Jun. 11, 2025.

International Search Report and Written Opinion for International Application No. PCT/IB2024/063115 mailed Jul. 4, 2025.

International Search Report and Written Opinion for International Application No. PCT/IB2024/063109 mailed Jun. 2, 2025.

International Search Report and Written Opinion for International Application No. PCT/IB2024/063110 mailed Jun. 2, 2025.

Invitation to pay Additional Fees for International Application No. PCT/IB2024/063113 mailed Apr. 17, 2025.

Invitation to pay Additional Fees for International Application No. PCT/IB2024/063115 mailed Apr. 15, 2025.

Issue Notification for U.S. Appl. No. 16/952,327 mailed Oct. 9, 2024.

Issue Notification for U.S. Appl. No. 17/070,670 mailed Jan. 8, 2025.

Issue Notification for U.S. Appl. No. 17/528,015 mailed Jun. 18, 2025.

Issue Notification for U.S. Appl. No. 17/528,807 mailed Oct. 9, 2024.

Issue Notification for U.S. Appl. No. 17/678,122 mailed Jun. 4, 2025.

Issue Notification for U.S. Appl. No. 17/857,402 mailed Dec. 18, 2024.

Non-Final Office Action for U.S. Appl. No. 17/078,472 mailed Nov. 19, 2024.

Non-Final Office Action for U.S. Appl. No. 17/176,344 mailed Feb. 20, 2025.

Non-Final Office Action for U.S. Appl. No. 17/528,015 mailed Oct. 21, 2024.

Non-Final Office Action for U.S. Appl. No. 17/609,589 mailed Jan. 30, 2025.

Non-Final Office Action for U.S. Appl. No. 17/677,571 mailed Feb. 20, 2025.

Non-Final Office Action for U.S. Appl. No. 17/678,122 issued Dec. 5, 2024.

Non-Final Office Action for U.S. Appl. No. 17/678,812 mailed Sep. 26, 2024.

Non-Final Office Action for U.S. Appl. No. 17/682,073 mailed May 28, 2024.

Non-Final Office Action for U.S. Appl. No. 17/682,104 mailed May 28, 2025.

Non-Final Office Action for U.S. Appl. No. 17/682,104 mailed Sep. 30, 2024.

Non-Final Office Action for U.S. Appl. No. 17/722,752 mailed Mar. 17, 2025.

Non-Final Office Action for U.S. Appl. No. 17/723,150 mailed Dec. 19, 2024.

Non-Final Office Action for U.S. Appl. No. 17/723,656 mailed Dec. 5, 2024.

Non-Final Office Action for U.S. Appl. No. 17/907,618 mailed May 2, 2025.

Non-Final Office Action for U.S. Appl. No. 18/001,680 dated Jun. 20, 2025.

Non-Final Office Action for U.S. Appl. No. 18/121,995 mailed Mar. 27, 2025.

Non-Final Office Action for U.S. Appl. No. 18/122,504 mailed Mar. 5, 2025.

Notice of Allowance for U.S. Appl. No. 17/070,670 mailed Sep. 11, 2024.

Notice of Allowance for U.S. Appl. No. 17/528,015 mailed Mar. 25, 2025.

Notice of Allowance for U.S. Appl. No. 17/532,318 mailed Feb. 25, 2025.

Notice of Allowance for U.S. Appl. No. 17/678,122 mailed Apr. 30, 2025.

Notice of Allowance for U.S. Appl. No. 17/723,150 mailed Apr. 7, 2025.

Notice of Allowance for U.S. Appl. No. 17/857,402 mailed Oct. 8, 2024.

Office Action for Chinese Application No. 202210520564.2 mailed May 23, 2025.

Office Action for Chinese Application No. 202210540435.X mailed May 22, 2025.

Office Action for Chinese Application No. 202210580274.7 mailed May 22, 2025.

Office Action for Chinese Application No. 202210791551.9 mailed May 16, 2025.

Office Action for Chinese Application No. 202210802982.0 mailed May 16, 2025.

Office Action for Chinese Application No. 202210847103.6 mailed May 16, 2025.

Office Action for Chinese Application No. 202310542349.7 mailed Jun. 4, 2025.

Office Action for Japanese Application No. 2022-559757 mailed Dec. 23, 2024.

Office Action for Japanese Application No. 2023-191120 mailed Oct. 1, 2024.

Office Action for Japanese Patent Application No. 2023-191120 mailed on Mar. 17, 2025.

Office Action for Japanese Patent Application No. 2024-066507 mailed Jun. 11, 2025.

Restriction Requirement for U.S. Appl. No. 17/907,618 mailed Feb. 13, 2025.

Restriction Requirement for U.S. Appl. No. 18/001,680 mailed Mar. 28, 2025.

Restriction Requirement for U.S. Appl. No. 18/122,486 mailed Apr. 14, 2025.

U.S. Appl. No. 18/889,744, filed Sep. 19, 2024.

U.S. Appl. No. 18/933,729, filed Oct. 31, 2024.

U.S. Appl. No. 18/933,745, filed Oct. 31, 2024.

U.S. Appl. No. 18/933,749, filed Oct. 31, 2024.

U.S. Appl. No. 18/933,759, filed Oct. 31, 2024.

U.S. Appl. No. 18/947,762, filed Nov. 14, 2024.

U.S. Appl. No. 18/949,258, filed Nov. 15, 2024.

U.S. Appl. No. 18/955,121, filed Nov. 21, 2024.

U.S. Appl. No. 18/958,181, filed Nov. 25, 2024.

U.S. Appl. No. 18/958,189 filed Nov. 25, 2024.

U.S. Appl. No. 18/958,196, filed Nov. 25, 2024.

U.S. Appl. No. 18/958,200, filed Nov. 25, 2024.

U.S. Appl. No. 19/011,892, filed Jan. 7, 2025.

U.S. Appl. No. 19/013,727, filed Jan. 8, 2025.

U.S. Appl. No. 19/013,744, filed Jan. 8, 2025.

U.S. Appl. No. 19/014,336, filed Jan. 9, 2025.

U.S. Appl. No. 19/014,344, filed Jan. 9, 2025.

Corrected Notice of Allowance for U.S. Appl. No. 17/722,752, mailed Jul. 25, 2025.

Corrected Notice of Allowance for U.S. Appl. No. 18/933,729, mailed Jul. 2, 2025.

Corrected Notice of Allowance for U.S. Appl. No. 18/933,729, mailed Jul. 23, 2025.

Examination Report for Australian Application No. 2025200291 mailed Sep. 16, 2025.

Extended Search Report for European Application No. 25163036.4 mailed Jul. 25, 2025.

Extended Search Report for European Application No. 25163043.0 mailed Jul. 28, 2025.

Final Office Action for U.S. Appl. No. 17/176,344 mailed Oct. 7, 2025.

Final Office Action for U.S. Appl. No. 18/122,504 mailed Oct. 23, 2025.

Issue Notification for U.S. Appl. No. 17/722,752 mailed Oct. 15, 2025.

Issue Notification for U.S. App. No. 17/723,150 mailed Oct. 14, 2025.

Non-Final Office Action for U.S. Appl. No. 17/078,472 mailed Aug. 12, 2025.

Non-Final Office Action for U.S. Appl. No. 17/609,589 mailed Sep. 5, 2025.

Non-Final Office Action for U.S. Appl. No. 17/677,571 mailed Aug. 20, 2025.

(56) References Cited

OTHER PUBLICATIONS

Non-Final Office Action for U.S. Appl. No. 17/723,656 mailed Nov. 3, 2025.
Non-Final Office Action for U.S. Appl. No. 18/447,025 mailed Nov. 5, 2025.
Non-Final Office Action for U.S. Appl. No. 18/511,532 mailed Aug. 18, 2025.
Non-Final Office Action for U.S. Appl. No. 18/652,959 mailed Oct. 1, 2025.
Notice of Allowance for U.S. Appl. No. 17/722,752 mailed Jul. 7, 2025.
Notice of Allowance for U.S. Appl. No. 18/933,729 mailed Jul. 1, 2025.
Office Action for Chinese Application No. 202180006817.8 mailed Jun. 13, 2025.
Office Action for Chinese Application No. 202210583463.X mailed Jun. 13, 2025.
Office Action for Chinese Application No. 202210587585.6 mailed Jun. 13, 2025.
Office Action for Chinese Application No. 202210802982.0 mailed Oct. 24, 2025.
Office Action for Chinese Application No. 202280015894.4 mailed Aug. 1, 2025.
Office Action for Chinese Application No. 202310541980.5 mailed Jun. 16, 2025.
Office Action for Chinese Application No. 202310542349.7 mailed Nov. 28, 2025.

BLOOD PUMP HOUSING

CROSS-REFERENCES TO RELATED APPLICATIONS

The present application is a continuation of U.S. Ser. No. 18/001,680 to Tuval, which is a US national phase application of PCT Application No. PCT/IB2022/051990 to Tuval (published as WO 22/189932), filed Mar. 7, 2022, which claims priority from:

U.S. Provisional Patent Application 63/158,708 to Tuval, entitled "Ventricular assist device," filed Mar. 9, 2021, and U.S. Provisional Patent Application 63/254,321 to Tuval, entitled "Ventricular assist device," filed Oct. 11, 2021, both of which US Provisional applications are incorporated herein by reference.

FIELD OF EMBODIMENTS OF THE INVENTION

Some applications of the present invention generally relate to medical apparatus. Specifically, some applications of the present invention relate to a ventricular assist device and methods of use thereof.

BACKGROUND

Ventricular assist devices are mechanical circulatory support devices designed to assist and unload cardiac chambers in order to maintain or augment cardiac output. They are used in patients suffering from a failing heart and in patients at risk for deterioration of cardiac function during percutaneous coronary interventions. Most commonly, a left-ventricular assist device is applied to a defective heart in order to assist left-ventricular functioning. In some cases, a right-ventricular assist device is used in order to assist right-ventricular functioning. Such ventricular assist devices are either designed to be permanently implanted or mounted on a catheter for temporary placement.

SUMMARY OF EMBODIMENTS

In accordance with some applications of the present invention, a left-ventricular assist device includes an impeller and a frame disposed around the impeller. The frame includes strut junctions at a proximal end of the frame. The strut junctions are configured to be maintained in open states, during assembly of the left ventricular assist device, to facilitate insertion of the impeller into the frame. A securing element holds the struts junctions in closed states, subsequent to the insertion of the impeller into the frame. A pump-outlet tube extends to a distal end of the frame and defines one or more lateral blood inlet openings that are configured to allow blood to flow from the subject's left ventricle into the pump-outlet tube.

For some applications (not shown), the pump-outlet tube defines two to four lateral blood-inlet openings. Typically, for such applications, each of the blood-inlet openings defines an area of more than 20 square mm (e.g., more than 30 square mm), and/or less than 60 square mm (e.g., less than 50 square mm), e.g., 20-60 square mm, or 30-50 square mm. Alternatively or additionally, the outlet tube defines a greater number of smaller blood-inlet openings 108, e.g., more than 10 blood-inlet openings, more than 50 blood-inlet openings, more than 100 blood-inlet openings, or more than 150 blood-inlet openings, e.g., 50-100 blood-inlet openings, 100-150 blood-inlet openings, or 150-200 blood-inlet openings. For some applications, the blood-inlet openings are sized such as (a) to allow blood to flow from the subject's left ventricle into the tube and (b) to block structures from the subject's left ventricle from entering into the frame. Typically, for such applications, a distal conical portion of the pump-outlet tube (which defines the blood-inlet openings) is configured to reduce a risk of structures from the left ventricle (such as chordae tendineae, trabeculae carneae, and/or papillary muscles) entering into the frame and potentially being damaged by the impeller and/or the axial shaft, and/or causing damage to the left ventricular assist device.

Typically, the portion of the pump-outlet tube that defines the blood-inlet openings (e.g., the distal conical portion of the pump-outlet tube) has a porosity of more than 40 percent, e.g., more than 50 percent, or more than 60 percent (where porosity is defined as the percentage of the area of this portion that is porous to blood flow). Thus, on the one hand, the blood-inlet openings are relatively small (in order to prevent structures of the left ventricular from entering the frame), but on the other hand, the porosity of the portion of the pump-outlet tube that defines the blood-inlet openings is relatively high, such as to allow sufficient blood flow into the pump-outlet tube.

For some applications, each the blood-inlet openings has a circular or a polygonal shape. For some applications, each of the blood-inlet openings has a hexagonal shape. Typically, using openings having a hexagonal shape allows the portion of the pump-outlet tube that defines the blood-inlet openings to have a relatively high porosity (e.g., as described hereinabove), while providing the portion of the pump-outlet tube that defines the blood-inlet openings with sufficient material between the blood-inlet openings to prevent tearing and/or stretching of the material.

For some applications, within a proximal region of the distal conical portion of the pump-outlet tube (which typically defines the blood-inlet openings), the widths of the gaps between the hexagonal (or other type of polygonal) holes are larger than widths of the gaps between the hexagonal (or other type of polygonal) holes within a distal region of the distal conical portion of the pump-outlet tube. Typically, for such applications, within the proximal region of the distal conical portion of the pump-outlet tube, a distance between opposing sides of each of the hexagons (or other type of polygons) is smaller than the distance between opposing sides of each of the hexagons (or other type of polygons) within the distal region of the distal conical portion of the pump-outlet tube. (Typically, such distances also represent the diameter of a circle that is enclosed by the respectively sized polygons.) Further typically, within the distal region of the distal conical portion of the pump-outlet tube, the distal conical portion of pump-outlet tube, has a higher porosity than within the proximal region of the distal conical portion of the pump-outlet tube.

Typically, the pump-outlet tube is coupled to the frame via heating. For some applications, within the proximal region of the distal conical portion of the pump-outlet tube, the gaps between the blood-inlet holes are wider and/or the blood-inlet holes are smaller than within the distal region, and/or the porosity is lower than within the distal region, in order to prevent and/or reduce damage (e.g., tearing, thinning, and/or stretching) that may be caused to the material that defines the blood-inlet holes from being damaged during the above-described heating process.

For some applications, the ventricular assist device includes an inner lining that lines the inside of the frame that houses the impeller. For some applications, the inner lining is disposed inside the frame, in order to provide a smooth inner surface (e.g., a smooth inner surface having a substantially circular cross-sectional shape) through which blood is pumped by impeller. Typically, by providing a smooth surface, the covering material reduces hemolysis that is caused by the pumping of blood by the impeller, relative to if the blood were pumped between the impeller and struts of the frame. For some applications, inner lining includes polyurethane, polyester, and/or silicone. Alternatively or additionally, the inner lining includes polyethylene terephthalate (PET) and/or polyether block amide (PEBAX®).

Typically, over an area of overlap between the inner lining and the pump-outlet tube, the inner lining is shaped to form a smooth surface (e.g., in order to reduce hemolysis, as described hereinabove), and the pump-outlet tube is shaped to conform with the struts of the frame. Further typically, the inner lining has a substantially circular cross-section. For some applications, over the area of overlap between the inner lining and the pump-outlet tube, the pump-outlet tube and the inner lining are coupled to each other, e.g., via vacuum, via an adhesive, and/or using a thermoforming procedure, for example, as described hereinbelow.

For some applications, the pump-outlet tube and the inner lining are bonded to each other and/or the frame in the following manner. For some applications, the inner lining is directly bonded to the inner surface of the frame before the pump-outlet tube is bonded to the outside of the frame. It is noted that, by bonding the inner lining directly to the inner surface of the frame, (rather than simply bonding the inner lining to the pump-outlet tube and thereby sandwiching the frame between the inner lining to the pump-outlet tube), any air bubbles, folds, and other discontinuities in the smoothness of the surface provided by the inner lining are typically avoided. For some applications, initially, the frame is treated so as to enhance bonding between the inner lining and the inner surface of the frame. For some applications, the treatment of the frame includes applying a plasma treatment to the frame (e.g., to the inner surface of the frame), dipping the frame in a coupling agent that has at least two functional groups that are configured to bond respectively with the frame and with the material form which the inner lining is made (e.g., silane solution), and/or dipping the frame in a solution that contains the material from which the inner lining is made (e.g., polyurethane solution). For some applications, subsequently, a solution that contains the material from which the inner lining is made (e.g., polyurethane solution) is sprayed over the central cylindrical portion of the cage. Once the inner surface of the frame has been treated, the inner lining is bonded to the inner surface of the central cylindrical portion of the frame (e.g., to the inner surface of a central cylindrical portion of the frame). Typically, the inner lining (which is shaped as a tube), is placed over a mandrel, the frame is placed over the inner lining, and pressure is applied by a heat shrinking process. Further typically, the assembly of the inner lining and the frame is heated in an oven.

Subsequent to the inner lining having been bonded to the frame, a portion of the pump-outlet tube is placed around the outside of the frame. Typically, the frame is heated from inside the frame, using the mandrel. Typically, while the frame is heated, an outer tube (which is typically made from silicone) applies pressure to the pump-outlet tube that causes pump-outlet tube to be pushed radially inwardly, in order to cause the pump-outlet tube to conform with the shapes of the struts of the frame. For some applications, during this stage, the mandrel that is placed inside the inner lining and which heats the inner lining is shorter than the length of the inner lining. The mandrel is typically placed within the inner lining such that margins are left outside of the mandrel at each of the ends of the inner lining. Typically, the inner lining acts as a shield to protect the pump-outlet tube from being overheated and becoming damaged by the heating of the mandrel. Placing the inner lining on the mandrel in the aforementioned manner prevents the mandrel from coming into direct contact with the frame and/or the pump-outlet tube. For some applications, the combination of the frame, the inner lining, and the portion of the pump-outlet tube disposed around the frame is subsequently shape set to a desired shape and dimensions using shape setting techniques as are known in the art.

Typically, the pump-outlet tube (or a different type of pump inlet guard) includes a coupling portion (e.g., a tubular coupling portion, as shown), which extends distally from the pump-outlet tube. For some applications, the coupling portion is coupled a surface that is distal to the frame in order to anchor the distal end of the pump-outlet tube. For some applications, the coupling portion defines a hole (e.g., toward the distal end of the coupling portion). For some applications, adhesive is applied between the coupling portion and the surface, via the hole. For some applications, the surface of is threaded. Typically, the threaded surface allows the adhesive to gradually and uniformly spread between the coupling portion and the surface. Further typically, the coupling portion is transparent, such that the spread of the adhesive is visible through the coupling portion. Therefore, for some applications, once the adhesive has sufficiently spread between the coupling portion and the surface (e.g., once the surface has been covered with the adhesive), application of the adhesive is terminated.

For some applications, the ventricular assist device including a protective braid at a distal end thereof. For some applications, in order to reduce a risk of structures from the left ventricle (such as chordae tendineae, trabeculae carneae, and/or papillary muscles) entering into the frame and potentially being damaged by the impeller and/or the axial shaft, and/or causing damage to the left ventricular assist device, the distal conical portion of the frame is covered (internally or externally) with the protective braid. Typically, within at least a portion of the cylindrical portion of the frame, the braid is embedded between the pump-outlet tube and the inner lining, such that, during crimping of the frame, the braid becomes crimped with the pump-outlet tube and the inner lining, thereby preventing the braid from moving with respect to pump-outlet tube and/or the inner lining.

In general, in the specification and in the claims of the present application, the term "proximal" and related terms, when used with reference to a device or a portion thereof, should be interpreted to mean an end of the device or the portion thereof that, when inserted into a subject's body, is typically closer to a location through which the device is inserted into the subject's body. The term "distal" and related terms, when used with reference to a device or a portion thereof, should be interpreted to mean an end of the device or the portion thereof that, when inserted into a subject's body, is typically further from the location through which the device is inserted into the subject's body.

The scope of the present invention includes using the apparatus and methods described herein in anatomical locations other than the left ventricle and the aorta. Therefore, the ventricular assist device and/or portions thereof are sometimes referred to herein (in the specification and the claims) as a blood pump.

There is therefore provided, in accordance with some applications of the present invention, an apparatus including:

a left-ventricular assist device including:

an impeller configured to be placed inside a left ventricle of a subject and to pump blood from the left ventricle to an aorta of the subject, by rotating;

a frame disposed around the impeller, the frame including a plurality of strut junctions at a proximal end of the frame, the strut junctions being configured to be maintained in open states, during assembly of the left ventricular assist device, to facilitate insertion of the impeller into the frame;

a securing element configured to hold the struts junctions in closed states, subsequent to the insertion of the impeller into the frame; and a pump-outlet tube configured to traverse an aortic valve of the subject, such that a proximal portion of the pump-outlet tube is disposed within the subject's aorta and a distal portion of the pump-outlet tube is disposed within the subject's left ventricle, the distal portion of the pump-outlet tube extending to a distal end of the frame and defining one or more lateral blood inlet openings that are configured to allow blood to flow from the subject's left ventricle into the pump-outlet tube.

In some applications, the securing element includes a ring.

In some applications, the left-ventricular assist device includes a portion that is distal to the frame, and the pump-outlet tube further includes a coupling portion that extends distally from the frame and that is coupled to the portion of the left-ventricular assist device that is distal the frame.

In some applications, the distal portion of the pump-outlet tube defines more than 10 blood-inlet openings that are sized such as (a) to allow blood to flow from the subject's left ventricle into the tube and (b) to block structures from the subject's left ventricle from entering into the frame. In some applications, the distal portion of the pump-outlet tube defines more than 50 blood-inlet openings that are sized such as (a) to allow blood to flow from the subject's left ventricle into the tube and (b) to block structures from the subject's left ventricle from entering into the frame.

In some applications, the left-ventricular assist device further includes:

a proximal radial bearing disposed within a proximal bearing housing at a proximal end of the frame;

a distal radial bearing disposed within a distal bearing housing at a distal end of the frame;

an axial shaft upon which the impeller is disposed, the axial shaft passing through the proximal radial bearing and the distal radial bearing, the securing element is configured to hold the struts junctions closed around an outer surface of the proximal bearing housing.

In some applications, the pump-outlet tube further includes a coupling portion that extends distally from the frame and that is coupled to the distal bearing housing. In some applications, a distal end of the frame is coupled to an outer surface of the distal bearing housing. In some applications, the left-ventricular assist device further includes a distal tip element, and the distal tip element is coupled to the distal bearing housing.

In some applications, the outer surface of the proximal bearing housing defines grooves that are shaped to receive the strut junctions. In some applications, the strut junctions define widened heads and the grooves are shaped to conform with the widened heads of the strut junctions.

In some applications, the proximal and distal radial bearings are made of a ceramic material and the proximal and distal bearing housings are made of a second material that is moldable into a desired shape. In some applications, the proximal and distal bearing housings are made of a metal and/or an alloy. In some applications, the axial shaft includes a metal and/or an alloy and the axial shaft is covered with ceramic sleeves along regions of the axial shaft that come into contact with either of the proximal and distal bearings during operation of the left-ventricular assist device.

There is further provided, in accordance with some applications of the present invention, a method of manufacturing a left ventricular assist device, the method including:

forming a frame such that the frame is closed at its distal end and such that a plurality of strut junctions at a proximal end of the frame are maintained in open states;

coupling a pump-outlet tube to the frame, such that a distal portion of the pump-outlet tube extends to a distal end of the frame and defines one or more lateral blood-inlet openings that are configured to allow blood to flow from the subject's left ventricle into the pump-outlet tube, the pump-outlet tube being configured traverse an aortic valve of a subject, such that a proximal portion of the pump-outlet tube is disposed within the subject's aorta and the distal portion of the pump-outlet tube is disposed within the subject's left ventricle;

inserting an impeller into the frame via the proximal end of the frame, the impeller being configured to pump blood through the pump-outlet tube, by rotating; and subsequently, closing the strut junctions at the proximal and of the frame, and maintaining the strut junctions in their closed states using a securing element.

In some applications, the pump-outlet tube further includes a coupling portion configured to extend distally from the frame, and the method further includes coupling the coupling portion to a portion of the left-ventricular assist device that is distal to the frame.

In some applications, the securing element includes a ring, and maintaining the strut junctions in their closed states using the securing element includes maintaining the strut junctions in their closed states using the ring.

In some applications, the left-ventricular assist device further includes:

a proximal radial bearing disposed within a proximal bearing housing at a proximal end of the frame;

a distal radial bearing disposed within a distal bearing housing at a distal end of the frame;

an axial shaft upon which the impeller is disposed, the axial shaft passing through the proximal radial bearing and the distal radial bearing, and maintaining the strut junctions in their closed states using the securing element includes maintaining the strut junctions in their closed states by holding the struts junctions closed around an outer surface of the proximal bearing housing.

In some applications, the pump-outlet tube further includes a coupling portion configured to extend distally from the frame, and the method further includes coupling the coupling portion to the distal bearing housing. In some applications, the method further includes coupling a distal end of the frame to an outer surface of the distal bearing housing. In some applications, the method further includes coupling a distal tip element to the distal bearing housing.

In some applications, the outer surface of the proximal bearing housing defines grooves that are shaped to receive the strut junctions, and holding the struts junctions closed around the outer surface of the proximal bearing housing includes holding the struts junctions within the grooves defined by the outer surface of the proximal bearing housing. In some applications, the strut junctions define widened heads, and holding the struts junctions within the grooves defined by the outer surface of the proximal bearing housing includes holding the struts junctions within grooves that are shaped to conform with the widened heads of the strut junctions.

In some applications, the proximal and distal radial bearings are made of a ceramic material and the proximal and distal bearing housings are made of a second material that is moldable into a desired shape. In some applications, the proximal and distal bearing housings are made of a metal and/or an alloy. In some applications, the axial shaft includes a metal and/or an alloy and the method further includes covering the axial shaft with ceramic sleeves along regions of the axial shaft that come into contact with either of the proximal and distal bearings during operation of the left-ventricular assist device.

There is further provided, in accordance with some applications of the present invention, an apparatus, including:

a left-ventricular assist device including:

an impeller configured to be placed inside a left ventricle of a subject and to pump blood from the left ventricle to an aorta of the subject, by rotating;

a frame disposed around the impeller; and a pump-outlet tube configured to traverse an aortic valve of the subject, such that a proximal portion of the tube is disposed within the subject's aorta and a distal portion of the pump-outlet tube is disposed within the subject's left ventricle, the distal portion of the pump-outlet tube extending to a distal end of the frame and defining more than 10 blood-inlet openings that are sized such as (a) to allow blood to flow from the subject's left ventricle into the tube and (b) to block structures from the subject's left ventricle from entering into the frame, a porosity of the distal portion of the pump-outlet tube, which defines the blood-inlet openings, is lower within a proximal region of the distal portion of the pump-outlet tube than within a distal region of the distal portion of the pump-outlet tube that is distal to the proximal region.

In some applications, each of the blood-inlet openings is shaped such that, in at least one direction, a width of the opening is less than 1 mm.

In some applications, a ratio of the porosity of the distal portion of the pump-outlet tube within the distal region to the porosity of the distal portion of the pump-outlet tube within the proximal region is more than 4:3.

In some applications, the porosity of the distal portion of the pump-outlet tube is varied between the proximal region and the distal region such as to account for varying blood flow dynamics at different regions of the distal portion of the pump-outlet tube. In some applications, the distal portion of the pump-outlet tube is conical, and the porosity of the distal portion of the pump-outlet tube is varied between the proximal region and the distal region such as to account for changes in the shape of the distal conical portion along its length.

In some applications, along the distal region of the distal portion of the pump-outlet tube, the pump-outlet tube defines large blood-inlet openings that are configured to reduce a risk of thrombosis relative to if the blood-inlet openings along the distal region of the distal conical portion of the pump-outlet tube were smaller.

In some applications, the distal portion of the pump-outlet tube defines more than 50 blood-inlet openings that are sized such as (a) to allow blood to flow from the subject's left ventricle into the tube and (b) to block structures from the subject's left ventricle from entering into the frame.

In some applications, the blood-inlet openings are rectangular and are shaped such that a ratio of lengths to widths of each of the blood-inlet openings is between 1.1:1 and 4:1. In some applications, the blood inlet openings are rectangular and are shaped such that a ratio of lengths to widths of each of the blood-inlet openings is between 3:2 and 5:2.

In some applications, the distal portion of the pump-outlet tube has a porosity of more than 40 percent. In some applications, the distal portion of the pump-outlet tube has a porosity of more than 50 percent. In some applications, the distal portion of the pump-outlet tube has a porosity of more than 60 percent.

In some applications, the frame defines a central cylindrical portion and a distal conical portion, the distal portion of the pump-outlet tube, which defines the blood-inlet openings, is conical and is disposed over the distal conical portion of the frame, and a portion of the pump-outlet tube that is proximal to the distal portion of the pump-outlet tube is coupled to the central cylindrical portion of the frame.

In some applications, the portion of the pump-outlet tube that is proximal to the distal portion of the pump-outlet tube is coupled to the central cylindrical portion of the frame via heating, and the porosity is lower is within the proximal region of the distal portion of the pump-outlet tube, such that damage that may be caused to a material that defines the blood-inlet holes within the proximal region of the distal portion of the pump-outlet tube is reduced during the heating relative to if the porosity within the proximal region of the distal portion of the pump-outlet tube was higher.

In some applications, the apparatus further includes an inner lining coupled to an inner surface of the central cylindrical portion of the frame, such that the inner lining provides the central cylindrical portion of the frame with a smooth inner surface.

In some applications, the proximal region of the distal portion of the pump-outlet tube extends along a length of 0.5-2 mm.

In some applications, the blood-inlet openings have polygonal shapes. In some applications, the blood-inlet openings have hexagonal shapes.

In some applications, within the proximal region of the distal portion of the pump-outlet tube, a diameter of a circle enclosed by each of the blood-inlet openings is between 0.1 and 0.6 mm. In some applications, within the proximal region of the distal portion of the pump-outlet tube, widths of gaps between adjacent blood-inlet openings are between 0.05 and 0.2 mm.

In some applications, within the distal region of the distal portion of the pump-outlet tube, a diameter of a circle enclosed by each of the blood-inlet openings is between 0.2 and 0.8 mm. In some applications, within the distal region of the distal portion of the pump-outlet tube, widths of gaps between adjacent blood-inlet openings are between 0.01 mm and 0.1 mm.

In some applications, a ratio of a diameter of a circle enclosed by each the blood-inlet openings with the distal region of the distal portion of the pump-outlet tube to a diameter of a circle enclosed by each of the blood-inlet openings with the proximal region of the distal portion of the pump-outlet tube is greater than 7:6. In some applications, a ratio of widths of gaps between adjacent blood-inlet openings with the proximal region of the proximal portion of the pump-outlet tube to widths of gaps between adjacent blood-inlet openings within the distal region of the distal portion of the pump-outlet tube is greater than 3:2.

There is further provided, in accordance with some applications of the present invention, a method, including:

manufacturing a housing for an impeller of a blood pump by:

treating a frame in order to enhance bonding between an inner surface of the frame and an inner lining;

subsequently, coupling the inner lining to the inner surface of the frame along at least a portion of a central cylindrical portion of the frame, the central cylindrical portion of the frame including struts that define a generally cylindrical shape;

subsequent to coupling the inner lining to the inner surface of the frame along at least a portion of the central cylindrical portion of the frame:

placing a mandrel inside the inner lining;

placing a portion of an elongate tube around at least a portion of the frame, the elongate tube including a proximal portion that defines at least one blood outlet opening;

while the portion of the elongate tube is disposed around at least the portion of the frame, heating the inner lining, the frame and the portion of the elongate tube, via the mandrel; and while heating the inner lining, the frame, and the portion of the elongate tube, applying pressure from outside the portion of the elongate tube, such as to cause the portion of the elongate tube to become coupled to the frame.

In some applications, struts of the central cylindrical portion of the frame define cells which are configured such that, in a non-radially-constrained configuration of the frame, a width of each of each of the cells within the central cylindrical portion of the frame as measured around a circumference of the central cylindrical portion of the frame is less than 2 mm.

In some applications, applying pressure from outside the portion of the elongate tube, while heating the inner lining, the frame and the portion of the elongate tube, includes causing the portion of the elongate tube to conform with a structure of the struts of the frame.

In some applications, coupling the inner lining to the inner surface of the frame along at least a portion of a central cylindrical portion of the frame includes coupling the inner lining to the inner surface of the frame along at least a portion of a central cylindrical portion of the frame, such that the inner lining has a substantially circular cross section. In some applications, coupling the inner lining to the inner surface of the frame along at least a portion of a central cylindrical portion of the frame includes coupling the inner lining to the inner surface of the frame along at least a portion of a central cylindrical portion of the frame, such that the inner lining provides a smooth inner surface to the portion of the central cylindrical portion of the frame to which the inner lining is coupled.

In some applications, coupling the inner lining to the inner surface of the frame along at least a portion of a central cylindrical portion of the frame includes avoiding air bubbles, folds, and other discontinuities in smoothness of a surface provided by the inner lining.

In some applications, treating the frame in order to enhance bonding between the inner surface of the frame and the inner lining includes applying a plasma treatment to the frame.

In some applications, coupling the inner lining to the inner surface of the frame along at least a portion of a central cylindrical portion of the frame includes:

placing the inner lining over a mandrel;

placing the frame over the inner lining; and applying pressure via a heat shrinking process.

In some applications, treating the frame in order to enhance bonding between the inner surface of the frame and the inner lining includes dipping the frame in a solution that contains the material from which the inner lining is made. In some applications, the inner lining includes polyurethane and dipping the frame in the solution includes dipping the frame in a polyurethane solution.

In some applications, treating the frame in order to enhance bonding between the inner surface of the frame and the inner lining includes spraying the inner surface of the portion of the central cylindrical portion of the frame with a solution that contains the material from which the inner lining is made. In some applications, the inner lining includes polyurethane and spraying the inner surface of the portion of the central cylindrical portion of the frame includes spraying the inner surface of the portion of the central cylindrical portion of the frame with a polyurethane solution.

In some applications, placing the mandrel inside the inner lining subsequent to coupling the inner lining to the inner surface of the frame along at least the portion of the central cylindrical portion of the frame includes placing a mandrel that is shorter than a length of the inner lining inside the inner lining. In some applications, placing the mandrel inside the inner lining subsequent to coupling the inner lining to the inner surface of the frame along at least the portion of the central cylindrical portion of the frame includes placing the mandrel within the inner lining such that margins are left outside of the mandrel at each end of the inner lining. In some applications, placing the mandrel within the inner lining such that margins are left outside of the mandrel at each end of the inner lining includes preventing the mandrel from coming into direct contact with the frame or the pump-outlet tube, thereby protecting the pump-outlet tube from being overheated and becoming damaged by the heating of the mandrel.

In some applications, treating the frame in order to enhance bonding between the inner surface of the frame and the inner lining includes dipping the frame in a coupling agent that has at least two functional groups that are configured to bond respectively with the frame and with a material form which the inner lining is made. In some applications, the inner lining includes polyurethane and dipping the frame in the coupling agent includes dipping the frame in the coupling agent includes dipping the frame in a silane solution.

There is further provided, in accordance with some applications of the present invention, a method, including:

manufacturing a housing for an impeller of a blood pump by:

placing a mandrel inside an inner lining, with a central cylindrical portion of a frame disposed around the inner lining, the central cylindrical portion of the frame including struts that define a generally cylindrical shape, the mandrel being shorter than a length of the inner lining;

placing a portion of an elongate tube around at least a portion of the frame, the elongate tube including a proximal portion that defines at least one blood outlet opening;

while the portion of the elongate tube is disposed around at least the portion of the frame, heating the inner lining, the frame and the portion of the elongate tube, via the mandrel; and while heating the inner lining, the frame, and the portion of the elongate tube, applying pressure from outside the portion of the elongate tube, such as to cause the portion of the elongate tube to become coupled to the frame.

In some applications, struts of the central cylindrical portion of the frame define cells which are configured such that, in a non-radially-constrained configuration of the frame, a width of each of each of the cells within the central cylindrical portion of the frame as measured around a circumference of the central cylindrical portion of the frame is less than 2 mm.

In some applications, applying pressure from outside the portion of the elongate tube, while heating the inner lining, the frame and the portion of the elongate tube, includes causing the portion of the elongate tube to conform with a structure of the struts of the frame.

In some applications, placing the mandrel inside the inner lining includes placing the mandrel within the inner lining such that margins are left outside of the mandrel at each end of the inner lining. In some applications, placing the mandrel within the inner lining such that margins are left outside of the mandrel at each end of the inner lining includes preventing the mandrel from coming into direct contact with the frame or the pump-outlet tube, thereby protecting the pump-outlet tube from being overheated and becoming damaged by the heating of the mandrel.

In some applications, the method further includes, prior to placing the mandrel inside the inner lining:

treating the frame in order to enhance bonding between an inner surface of the frame and the inner lining; and coupling the inner lining to the inner surface of the frame along at least a portion of the central cylindrical portion of the frame.

In some applications, coupling the inner lining to the inner surface of the frame along at least a portion of the central cylindrical portion of the frame includes coupling the inner lining to the inner surface of the frame along at least a portion of the central cylindrical portion of the frame, such that the inner lining has a substantially circular cross section. In some applications, coupling the inner lining to the inner surface of the frame along at least a portion of the central cylindrical portion of the frame includes coupling the inner lining to the inner surface of the frame along at least a portion of the central cylindrical portion of the frame, such that the inner lining provides a smooth inner surface to the portion of the central cylindrical portion of the frame to which the inner lining is coupled.

In some applications, coupling the inner lining to the inner surface of the frame along at least a portion of the central cylindrical portion of the frame includes avoiding air bubbles, folds, and other discontinuities in a smoothness of a surface provided by the inner lining.

In some applications, treating the frame in order to enhance bonding between the inner surface of the frame and the inner lining includes applying a plasma treatment to the frame.

In some applications, coupling the inner lining to the inner surface of the frame along at least a portion of a central cylindrical portion of the frame includes:

placing the inner lining over a mandrel;

placing the frame over the inner lining; and applying pressure via a heat shrinking process.

In some applications, treating the frame in order to enhance bonding between the inner surface of the frame and the inner lining includes dipping the frame in a solution that contains the material from which the inner lining is made. In some applications, the inner lining includes polyurethane and dipping the frame in the solution includes dipping the frame in a polyurethane solution.

In some applications, treating the frame in order to enhance bonding between the inner surface of the frame and the inner lining includes spraying the inner surface of the portion of the central cylindrical portion of the frame with a solution that contains the material from which the inner lining is made. In some applications, the inner lining includes polyurethane and spraying the inner surface of the portion of the central cylindrical portion of the frame includes spraying the inner surface of the portion of the central cylindrical portion of the frame with a polyurethane solution.

In some applications, treating the frame in order to enhance bonding between the inner surface of the frame and the inner lining includes dipping the frame in a coupling agent that has at least two functional groups that are configured to bond respectively with the frame and with a material form which the inner lining is made. In some applications, wherein the inner lining includes polyurethane and dipping the frame in the coupling agent includes dipping the frame in the coupling agent includes dipping the frame in a silane solution.

There is further provided, in accordance with some applications of the present invention, an apparatus including:

a left-ventricular assist device including:

an impeller configured to be placed inside a left ventricle of a subject and to pump blood from the left ventricle to an aorta of the subject, by rotating;

a frame disposed around the impeller, the frame defining a distal conical portion;

a surface disposed distally to the frame; and an inlet guard disposed over the distal conical portion of the frame, the inlet guard:

defining blood-inlet openings that are sized such as (a) to allow blood to flow from the subject's left ventricle into the tube and (b) to block structures from the subject's left ventricle from entering into the frame, and a distal coupling portion, the distal coupling portion being configured to be coupled to the surface that is disposed distally to the frame, and the distal coupling portion defining a hole which is configured to facilitate application of an adhesive between the distal coupling portion and the surface disposed distally to the frame.

In some applications, the inlet guard includes a distal portion of a pump-outlet tube, the pump-outlet tube being configured to traverse an aortic valve of the subject, such that a proximal portion of the pump-outlet tube is disposed within the subject's aorta and the distal portion of the pump-outlet tube is disposed within the subject's left ventricle.

In some applications, the surface disposed distally to the frame is ridged such as to enhance bonding between the surface and the coupling portion. In some applications, the surface disposed distally to the frame is threaded, such as to allow the adhesive to gradually and uniformly spread between the coupling portion and the surface.

In some applications, the coupling portion is tubular. In some applications, the coupling portion is transparent such that spread of adhesive between the coupling portion and the surface is visible.

In some applications, the left-ventricular assist device further includes:

a proximal radial bearing disposed within a proximal bearing housing at a proximal end of the frame;

a distal radial bearing disposed within a distal bearing housing at a distal end of the frame;

an axial shaft upon which the impeller is disposed, the axial shaft passing through the proximal radial bearing and the distal radial bearing, the surface to which the distal coupling portion is coupled includes at least a portion of an outer surface of the distal bearing housing.

In some applications, a distal end of the frame is coupled to a further portion of the outer surface of the distal bearing housing. In some applications, the left-ventricular assist device further includes a distal tip element, and the distal tip element is coupled to a further portion of the outer surface of the distal bearing housing.

In some applications, a proximal end of the frame is coupled to an outer surface of the proximal bearing housing. In some applications, the frame includes a plurality of strut junctions at a proximal end of the frame, the strut junctions being configured to be maintained in open states to facilitate insertion of the impeller into the frame, during assembly of the left ventricular assist device, and the proximal end of the frame is coupled to the outer surface of the proximal bearing housing by a securing element holding the struts junctions in closed states around the outer surface of the proximal bearing housing.

In some applications, the proximal and distal radial bearings are made of a ceramic material and the proximal and distal bearing housings are made of a second material that is moldable into a desired shape. In some applications, the proximal and distal bearing housings are made of a metal and/or an alloy. In some applications, the axial shaft includes a metal and/or an alloy and the axial shaft is covered with ceramic sleeves along regions of the axial shaft that come into contact with either of the proximal and distal bearings during operation of the left-ventricular assist device.

There is further provided, in accordance with some applications of the present invention, an apparatus, including:

a ventricular assist device including:

a frame including struts that define a plurality of cells, the frame being configured such that, in a non-radially-constrained configuration of the frame, the frame includes a generally cylindrical central portion;

a pump-outlet tube that defines one or more blood outlet openings, a portion of the pump-outlet tube being disposed outside the frame and coupled to the generally cylindrical central portion of the frame, such that the portion of the pump-outlet tube conforms with a structure of struts of the frame;

an inner lining coupled to an inside of the generally cylindrical central portion of the frame, such as to provide the generally cylindrical portion of the frame with a smooth inner surface;

an impeller disposed at least partially inside the generally cylindrical central portion of the frame and configured to pump blood through the tube and out of the one of more blood outlet openings; and a protective braid disposed over a distal portion of the frame and configured to block structures from the subject's left ventricle from entering into the frame, a proximal end of the protective braid being embedded between the pump-outlet tube and the inner lining, such that, during crimping of the frame, the braid becomes crimped with the pump-outlet tube and the inner lining, thereby preventing the braid from moving with respect to pump-outlet tube or the inner lining.

In some applications, the braid is woven into struts of the distal portion of frame.

In some applications, the distal portion of the frame is conical, and the protective braid extends until the end of the distal conical portion of the frame.

In some applications, the braid is covered along a distal part of the distal conical portion of the frame, in order to prevent thrombi from forming on the braid within the distal part of the distal conical portion of the frame.

In some applications, within a distal part of the distal conical portion of the frame, the braid is opened such as to define large apertures, in order to prevent thrombi from forming on the braid within the distal part of the distal conical portion of the frame. In some applications, within a distal part of the distal conical portion of the frame, the braid is cut such as to define large apertures, in order to prevent thrombi from forming on the braid within the distal part of the distal conical portion of the frame.

In some applications, the braid is covered along a distal part of the distal conical portion of the frame, and the covered braid is cut such as to define one or more large apertures, in order to prevent thrombi from forming on the braid within the distal part of the distal conical portion of the frame. In some applications, an aperture is cut from the covered braid around the full circumference of the frame, such that that the covered braid defines an aperture that extends around the full circumference of the distal part of the distal conical portion of the frame. In some applications, the aperture is cut such that it extends until a distal end of the distal conical portion of the frame, such that there is a single aperture that extends around the full circumference of the frame and until the distal end of the distal conical portion of the frame.

The present invention will be more fully understood from the following detailed description of embodiments thereof, taken together with the drawings, in which:

DETAILED DESCRIPTION OF EMBODIMENTS

Figure 1A:
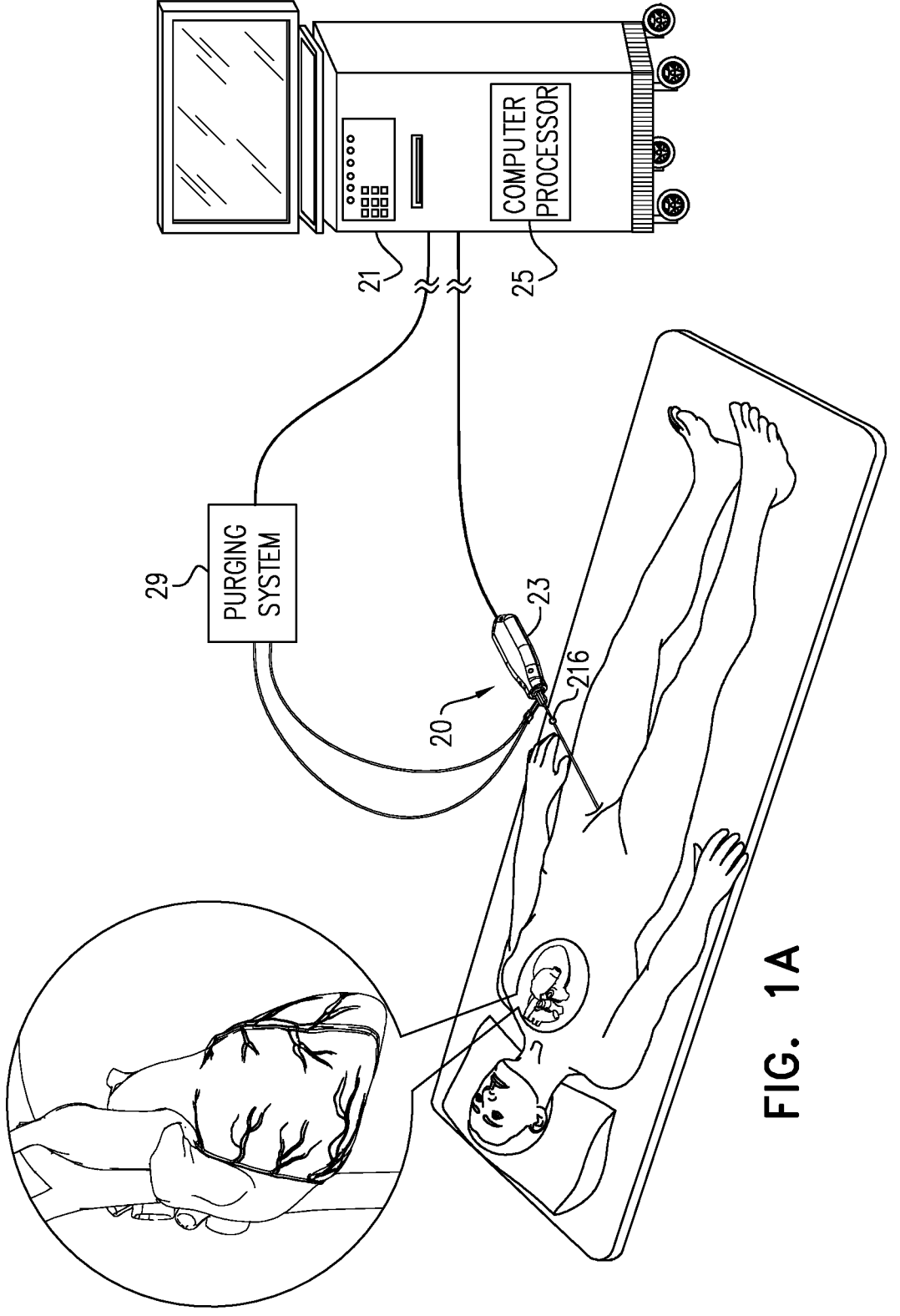
FIGS. 1A, 1B, and 1C are schematic illustrations of a ventricular assist device, a distal end of which is configured to be placed in a subject's left ventricle, in accordance with some applications of the present invention.
Figure 1B:
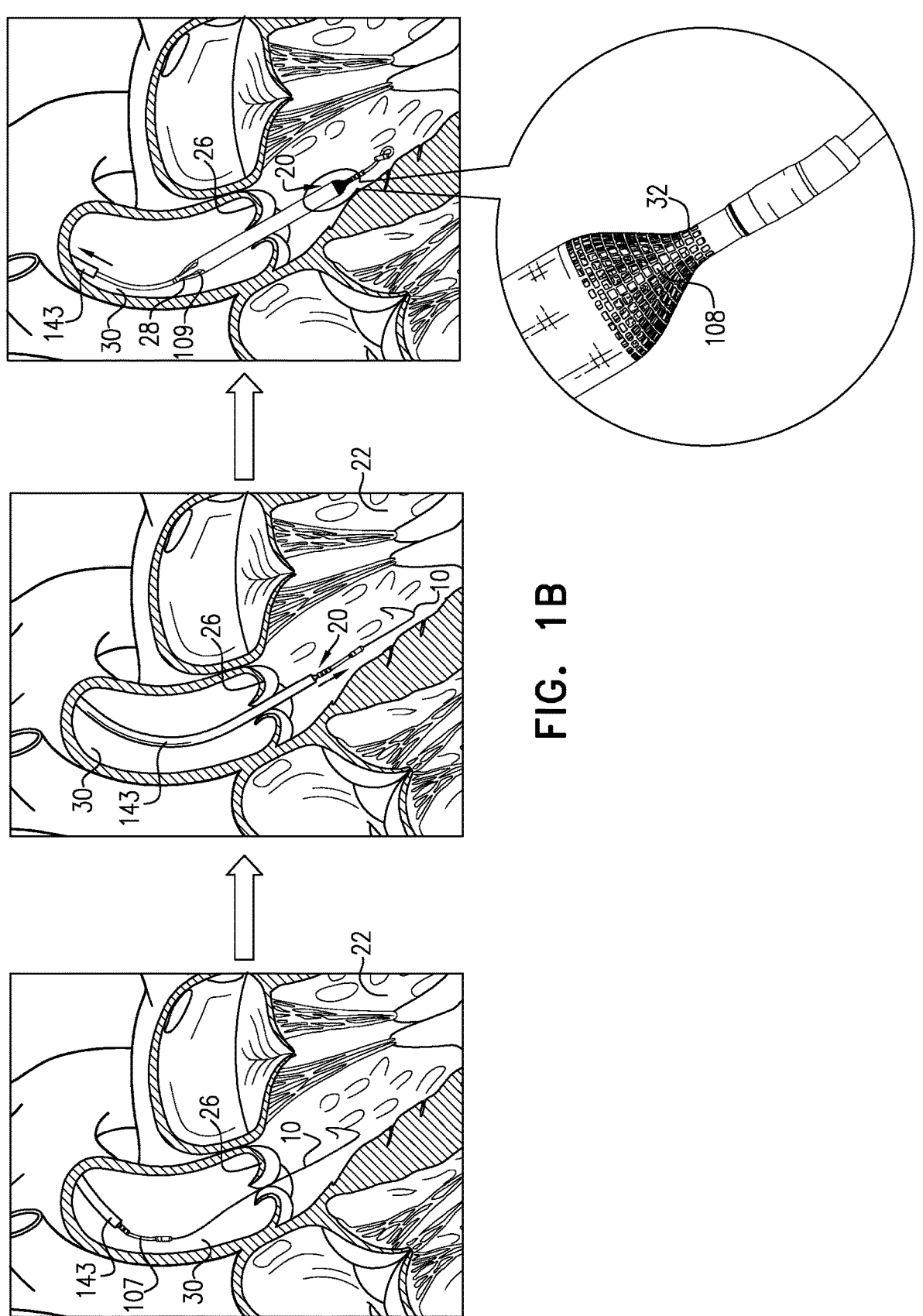
Figure 1C:
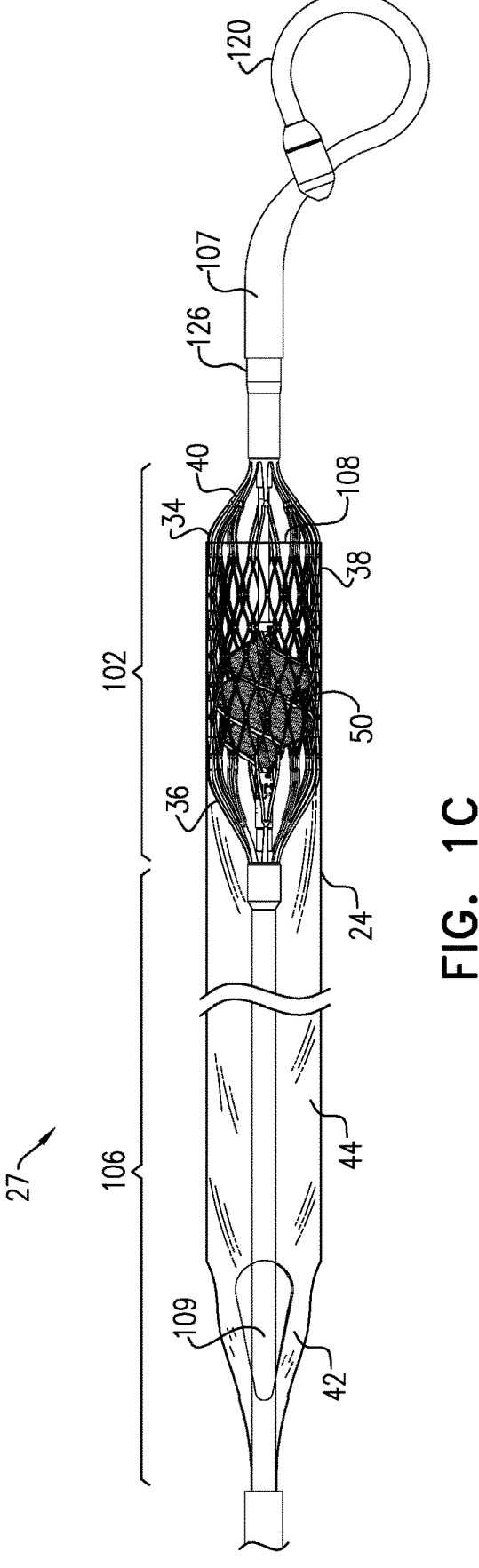

Reference is now made to FIGS. 1A, 1B, and 1C, which are schematic illustrations of a ventricular assist device 20, a distal end of which is configured to be disposed in a subject's left ventricle 22, in accordance with some applications of the present invention. FIG. 1A shows an overview of the ventricular assist device system including a control console 21, and a motor unit 23, FIG. 1B shows the ventricular assist device being inserted into the subject's left ventricle, and FIG. 1C shows a pump-head portion 27 of the ventricular assist device in greater detail. The ventricular assist device includes a pump-outlet tube 24, which traverses an aortic valve 26 of the subject, such that a proximal end 28 of the pump-outlet tube is disposed in an aorta 30 of the subject and a distal end 32 of the pump-outlet tube is disposed within left ventricle 22. Pump-outlet tube 24 (which is sometimes referred to herein as a "blood-pump tube") is typically an elongate tube, an axial length of the pump-outlet tube typically being substantially larger than its diameter. The scope of the present invention includes using the apparatus and methods described herein in anatomical locations other than the left ventricle and the aorta. Therefore, the ventricular assist device and/or portions thereof are sometimes referred to herein (in the specification and the claims) as a blood pump.

For some applications, the ventricular assist device is used to assist the functioning of a subject's left ventricle during a percutaneous coronary intervention. In such cases, the ventricular assist device is typically used for a period of up to six hours (e.g., up to ten hours), during a period in which there is risk of developing hemodynamic instability (e.g., during or immediately following the percutaneous coronary intervention). Alternatively or additionally, the ventricular assist device is used to assist the functioning of a subject's left ventricle for a longer period (e.g., for example, 2-20 days, e.g., 4-14 days) upon a patient suffering from cardiogenic shock, which may include any low-cardiac-output state (e.g., acute myocardial infarction, myocarditis, cardiomyopathy, post-partum, etc.). For some applications, the ventricular assist device is used to assist the functioning of a subject's left ventricle for yet a longer period (e.g., several weeks or months), e.g., in a "bridge to recovery" treatment. For some such applications, the ventricular assist device is permanently or semi-permanently implanted, and the impeller of the ventricular assist device is powered transcutaneously, e.g., using an external antenna that is magnetically coupled to the impeller.

As shown in FIG. 1B, which shows steps in the deployment of the ventricular assist device in the left ventricle, typically the distal end of the ventricular assist device is guided to the left ventricle over a guidewire 10. During the insertion of the distal end of the device to the left ventricle, a delivery catheter 143 is disposed over the distal end of the device. Once the distal end of the device is disposed in the left ventricle, the delivery catheter is typically retracted to the aorta, and the guidewire is withdrawn from the subject's body. The retraction of the delivery catheter typically causes self-expandable components of the distal end of the device to assume non-radially-constrained configurations, as described in further detail hereinbelow. Typically, the ventricular assist device is inserted into the subject's body in order to provide an acute treatment to the subject. For some applications, in order to withdraw the left ventricular device from the subject's body at the end of the treatment, the delivery catheter is advanced over the distal end of the device, which causes the self-expandable components of the distal end of the device to assume radially-constrained configurations. Alternatively or additionally, the distal end of the device is retracted into the delivery catheter which causes the self-expandable components of the distal end of the device to assume radially-constrained configurations.

For some applications (not shown), the ventricular assist device and/or delivery catheter 143 includes an ultrasound transducer at its distal end and the ventricular assist device is advanced toward the subject's ventricle under ultrasound guidance.

Reference is made to FIG. 1C, which shows pump-head portion 27 of ventricular assist device 20, in accordance with some applications of the present invention, in greater detail. Typically, an impeller 50 is disposed within a distal portion 102 of pump-outlet tube 24 and is configured to pump blood from the left ventricle into the aorta by rotating. The pump-outlet tube typically defines one or more blood-inlet openings 108 at the distal end of the pump-outlet tube, via which blood flows into the pump-outlet tube from the left ventricle, during operation of the impeller. As shown in FIG. 1C, for some applications, the pump-outlet tube defines a single axially-facing blood-inlet opening. Alternatively, the pump-outlet tube defines a plurality of lateral blood-inlet openings (e.g., as shown in FIG. 1B), as described in further detail hereinbelow. For some applications, proximal portion 106 of the pump-outlet tube defines one or more blood-outlet openings 109, via which blood flows from the pump-outlet tube into the ascending aorta, during operation of the impeller.

For some applications, control console 21 (shown in FIG. 1A), which typically includes a computer processor 25, drives the impeller to rotate. For example, the computer processor may control a motor 74 (shown in FIG. 7), which is disposed within motor unit 23 (shown in FIG. 1A) and which drives the impeller to rotate via a drive cable 130 (shown in FIG. 7). For some applications, the computer processor is configured to detect a physiological parameter of the subject (such as left-ventricular pressure, cardiac afterload, rate of change of left-ventricular pressure, etc.) and to control rotation of the impeller in response thereto, as described in further detail hereinbelow. Typically, the operations described herein that are performed by the computer processor, transform the physical state of a memory, which is a real physical article that is in communication with the computer processor, to have a different magnetic polarity, electrical charge, or the like, depending on the technology of the memory that is used. Computer processor 25 is typically a hardware device programmed with computer program instructions to produce a special-purpose computer. For example, when programmed to perform the techniques described herein, computer processor 25 typically acts as a special-purpose, ventricular-assist computer processor and/ or a special-purpose, blood-pump computer processor.

For some applications, a purging system 29 (shown in FIG. 1A) drives a fluid (e.g., a glucose solution) to pass through portions of ventricular assist device 20, for example, in order to cool portions of the device, to purge and/or lubricate interfaces between rotating parts and stationary bearings, and/or in order to wash debris from portions of the device.

Typically, along distal portion 102 of pump-outlet tube 24, a frame 34 is disposed within the pump-outlet tube around impeller 50. The frame is typically made of a shape-memory alloy, such as nitinol. For some applications, the shape-memory alloy of the frame is shape set such that at least a portion of the frame (and thereby distal portion 102 of tube 24) assumes a generally circular, elliptical, or polygonal cross-sectional shape in the absence of any forces being applied to distal portion 102 of tube 24. By assuming its generally circular, elliptical, or polygonal cross-sectional shape, the frame is configured to hold the distal portion of the pump-outlet tube in an open state. Typically, during operation of the ventricular assist device, the distal portion of the pump-outlet tube is configured to be placed within the subject's body, such that the distal portion of the pump-outlet tube is disposed at least partially within the left ventricle.

For some applications, along proximal portion 106 of pump-outlet tube 24, the frame is not disposed within the pump-outlet tube, and the pump-outlet tube is therefore not supported in an open state by frame 34. Pump-outlet tube 24 is typically made of a blood-impermeable collapsible material. For example, pump-outlet tube 24 may include polyurethane, polyester, and/or silicone. Alternatively or additionally, the pump-outlet tube is made of polyethylene terephthalate (PET) and/or polyether block amide (e.g., PEBAX®). For some applications (not shown), the pump-outlet tube is reinforced with a reinforcement structure, e.g., a braided reinforcement structure, such as a braided nitinol tube. Typically, the proximal portion of the pump-outlet tube is configured to be placed such that it is at least partially disposed within the subject's ascending aorta. For some applications, the proximal portion of the pump-outlet tube traverses the subject's aortic valve, passing from the subject's left ventricle into the subject's ascending aorta, as shown in FIG. 1B.

As described hereinabove, the pump-outlet tube typically defines one or more blood-inlet openings 108 at the distal end of the pump-outlet tube, via which blood flows into the pump-outlet tube from the left ventricle, during operation of the impeller. For some applications, the proximal portion of the pump-outlet tube defines one or more blood-outlet openings 109, via which blood flows from the pump-outlet tube into the ascending aorta, during operation of the impeller. Typically, the pump-outlet tube defines a plurality of blood-outlet openings 109, for example, between two and eight blood-outlet openings (e.g., between two and four blood-outlet openings). During operation of the impeller, the pressure of the blood flow through the pump-outlet tube typically maintains the proximal portion of the tube in an open state. For some applications, in the event that, for example, the impeller malfunctions, the proximal portion of the pump-outlet tube is configured to collapse inwardly, in response to pressure outside of the proximal portion of the pump-outlet tube exceeding pressure inside the proximal portion of the pump-outlet tube. In this manner, the proximal portion of the pump-outlet tube acts as a safety valve, preventing retrograde blood flow into the left ventricle from the aorta.

Referring again to FIG. 1C, for some applications, frame 34 is shaped such that the frame defines a proximal conical portion 36, a central cylindrical portion 38, and a distal conical portion 40. Typically, the proximal conical portion is proximally-facing, i.e., facing such that the narrow end of the cone is proximal with respect to the wide end of the cone. Further typically, the distal conical portion is distally-facing, i.e., facing such that the narrow end of the cone is distal with respect to the wide end of the cone. For some applications, pump-outlet tube 24 extends to the end of cylindrical portion 38 (or slightly proximal or distal thereof), such that the distal end of the pump-outlet tube defines a single axially-facing blood-inlet opening 108, as shown in FIG. 1C. For some applications, within at least a portion of frame 34 (e.g., along all of, or a portion of, the central cylindrical portion of the frame), an inner lining 39 lines the frame. FIG. 1C shows an embodiment of the pump-head portion without inner lining 39, but several figures (e.g., FIGS. 4, 5A, 6A-6B, 9A-9B, 10A-10C, 11A, 11C, 13A, and 14A-C) show embodiments of a pump-head portion that includes inner lining 39. In accordance with respective applications, the inner lining partially overlaps or fully overlaps with pump-outlet tube 24 over the portion of the frame that the inner lining lines, as described in further detail hereinbelow with reference to FIGS. 9A-B.

Typically, pump-outlet tube 24 includes a conical proximal portion 42 and a cylindrical central portion 44. The proximal conical portion is typically proximally-facing, i.e., facing such that the narrow end of the cone is proximal with respect to the wide end of the cone. Typically, blood-outlet openings 109 are defined by pump-outlet tube 24, such that the openings extend at least partially along the proximal conical section of tube 24. For some such applications, the blood-outlet openings are teardrop-shaped, as shown in FIG. 1C. Typically, the teardrop-shaped nature of the blood-outlet openings in combination with the openings extending at least partially along the proximal conical section of tube 24 causes blood to flow out of the blood-outlet openings along flow lines that are substantially parallel with the longitudinal axis of tube 24 at the location of the blood-outlet openings.

For some applications (not shown), the diameter of pump-outlet tube 24 changes along the length of the central portion of the pump-outlet tube, such that the central portion of the pump-outlet tube has a frustoconical shape. For example, the central portion of the pump-outlet tube may widen from its proximal end to is distal end, or may narrow from its proximal end to its distal end. For some applications, at its proximal end, the central portion of the pump-outlet tube has a diameter of between 5 and 7 mm, and at its distal end, the central portion of the pump-outlet tube has a diameter of between 8 and 12 mm.

Again referring to FIG. 1C, the ventricular assist device typically includes a distal-tip element 107 that is disposed distally with respect to frame 34 and that includes an axial-shaft-receiving tube 126 and a distal-tip portion 120. Typically, the axial-shaft receiving tube is configured to receive a distal portion of an axial shaft 92 of the pump-head portion during axial back-and-forth motion of the axial shaft (as described in further detail hereinbelow), and/or during delivery of the ventricular assist device. (Typically, during delivery of the ventricular assist device, the frame is maintained in a radially-constrained configuration, which typically causes the axial shaft to be disposed in a different position with respect to the frame relative to its disposition with respect to the frame during operation of the ventricular assist device). Typically, distal-tip portion 120 is configured to assume a curved shape upon being deployed within the subject's left ventricle, e.g., as shown in FIG. 1C. For some applications, the curvature of the distal-tip portion is configured to provide an atraumatic tip to ventricular assist device 20. Alternatively or additionally, the distal-tip portion is configured to space blood-inlet openings 108 of the ventricular assist device from walls of the left ventricle.

As shown in the enlarged portion of FIG. 1B, for some applications, pump-outlet tube 24 extends to the end of distal conical portion 40 of the frame, and the pump-outlet tube defines a plurality of lateral blood-inlet openings 108, as described in further detail hereinbelow. For such applications, the pump-outlet tube typically defines a distal conical portion that is distally facing, i.e., such that the narrow end of the cone is distal with respect to the wide end of the cone. For some such applications (not shown), the pump-outlet tube defines two to four lateral blood-inlet openings (e.g., four lateral blood-inlet openings, as shown). Typically, for such applications, each of the blood-inlet openings defines an area of more than 20 square mm (e.g., more than 30 square mm), and/or less than 60 square mm (e.g., less than 50 square mm), e.g., 20-60 square mm, or 30-50 square mm. Alternatively or additionally, the outlet tube defines a greater number of smaller lateral blood-inlet openings, e.g., more than 10 blood-inlet openings, more than 50 blood-inlet openings, more than 200 blood-inlet openings, or more than 400 blood-inlet openings, e.g., 50-100 blood-inlet openings, 100-400 blood-inlet openings, or 400-600 blood-inlet openings. For some such applications, each of the blood-inlet openings defines an area of more than 0.05 square mm (e.g., more than 0.1 square mm), and/or less than 3 square mm (e.g., less than 1 square mm), e.g., 0.05-3 square mm, or 0.1-1 square mm. Alternatively, each of the blood-inlet openings defines an area of more than 0.1 square mm (e.g., more than 0.3 square mm), and/or less than 5 square mm (e.g., less than 1 square mm), e.g., 0.1-5 square mm, or 0.3-1 square mm.

Figure 2:
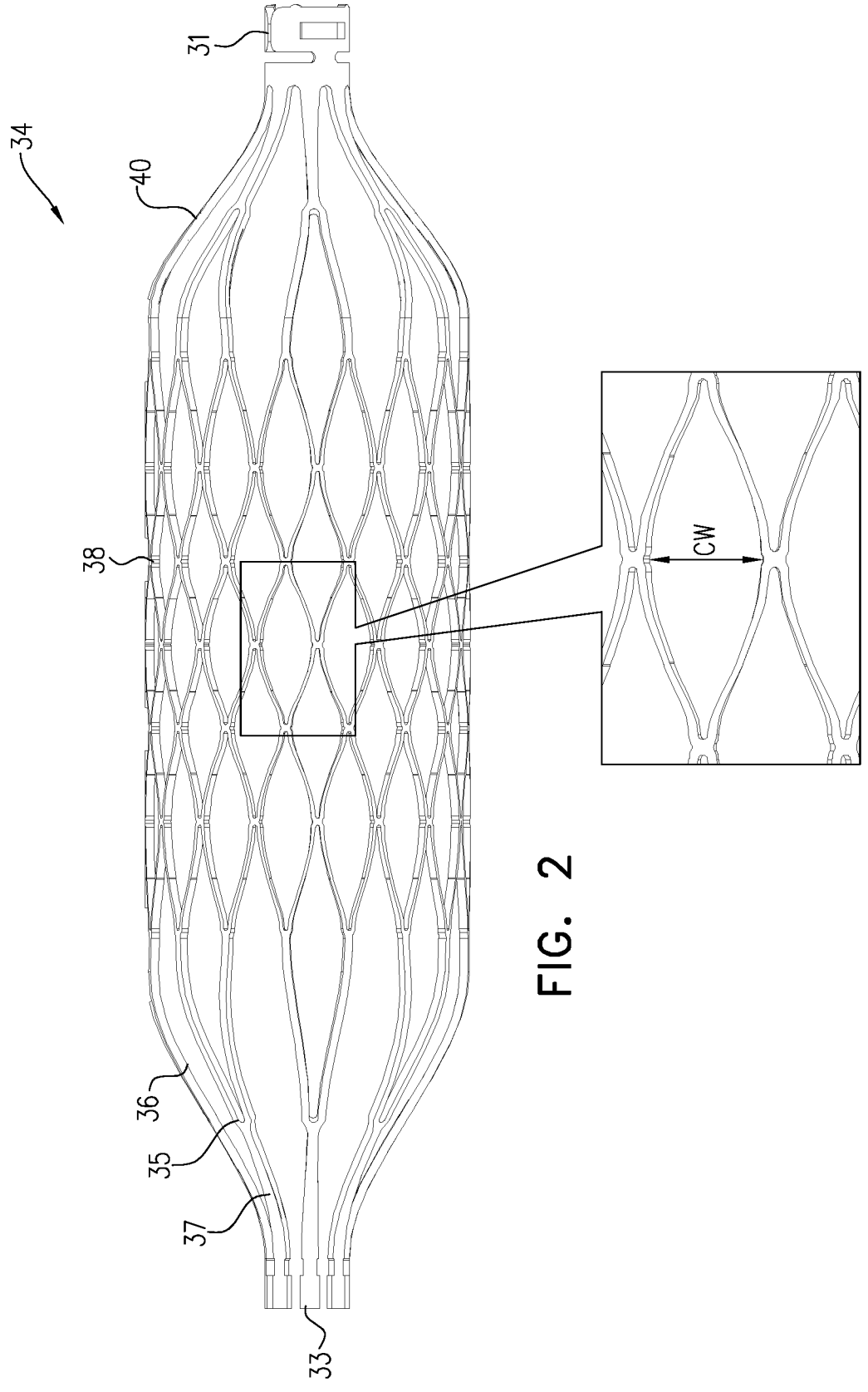
FIG. 2 is a schematic illustration of a frame that houses an impeller of a ventricular assist device, in accordance with some applications of the present invention.

Reference is now made to FIG. 2, which is schematic illustration of frame 34 that houses an impeller of ventricular assist device 20, in accordance with some applications of the present invention. Frame 34 is typically made of a shape-memory alloy, such as nitinol, and the shape-memory alloy of the frame is shape set such that the central portion of the frame (and thereby tube 24) assumes a generally circular, elliptical, or polygonal cross-sectional shape in the absence of any forces being applied to pump-outlet tube 24. By assuming its generally circular, elliptical, or polygonal cross-sectional shape, the frame is configured to hold the distal portion of the tube in an open state.

Typically, the frame is a stent-like frame, in that it comprises struts that, in turn, define cells. Further typically, the frame is covered with pump-outlet tube 24, and/or covered with an inner lining 39, described hereinbelow, with reference to FIGS. 9A-B. As described hereinbelow, for some applications impeller 50 undergoes axial back-and-forth motion with respect to frame 34. Typically, over the course of the motion of the impeller with respect to the frame the location of the portion of the impeller that defines the maximum span of the impeller is disposed within central cylindrical portion 38 of frame 34. In some cases, if the cells of the central cylindrical portion 38 of frame 34 are too large, then pump-outlet tube 24, and/or inner lining 39 gets stretched between edges of the cells, such that the pump-outlet tube 24, and/or inner lining 39 does not define a circular cross-section. For some applications, if this occurs in the region in which the portion of the impeller that defines the maximum span of the impeller is disposed, this results in a non-constant gap between the edges of the impeller blades and tube 24 (and/or inner lining) at that location, over the course of a rotation cycle of the impeller. For some applications, this may lead to increased hemolysis relative to if there were a constant gap between the edges of the impeller blades and tube 24 (and/or inner lining) at that location, over the course of the rotation cycle of the impeller.

Referring to FIG. 2, at least partially in view of the issues described in the above paragraph, within central cylindrical portion 38 of frame 34, the frame defines a large number of relatively small cells. Typically, when the frame is disposed in its non-radially-constrained configuration, the maximum cell width CW of the each of the cells (i.e., the distance from the inner edge of the strut at the central junction on one side of the cell to the inner edge of the strut at the central junction on the other side of the cell, as measured around the circumference of cylindrical portion 38) within the cylindrical portion of the frame is less than 2 mm, e.g., between 1.4 mm and 1.6 mm, or between 1.6 and 1.8 mm. Since the cells are relatively small, inner lining 39 defines a substantially circular cross-section within the cylindrical portion of the frame.

Still referring to FIG. 2, and starting from the distal end of the frame (which is to the right of the figure), typically the frame defines the following portions (a) coupling portion 31 via which the frame is coupled to a distal bearing housing 118H (shown in FIG. 5A) of the ventricular assist device, (b) distal conical portion 40, (c) central cylindrical portion 38, (d) proximal conical portion 36, and (e) proximal strut junctions 33. As illustrated, as the frame transitions from a proximal end of the frame toward the center of the frame (e.g., as the frame transitions from proximal strut junctions 33, through proximal conical portion 36, and to central cylindrical portion 38), struts 37 of the frame pass through junctions 35, at which the two struts branch from a single strut, in a Y-shape. As described in further detail hereinbelow, typically frame 34 is placed in a radially-constrained (i.e., crimped) configuration within delivery catheter 143 by the frame being axially elongated. Moreover, the frame typically transmits its radial narrowing to the impeller, and the impeller becomes radially constrained by becoming axially elongated within the frame. For some applications, the struts of the frame being configured in the manner described above facilitates transmission of axial elongation from the delivery catheter (or other device that is configured to crimp the frame) to the frame, which in turn facilitates transmission of axial elongation to the impeller. This is because the pairs of struts that branch from each of junctions 35 are configured to pivot about the junction and move closer to each other such as to close.

Still referring to FIG. 2, during the assembly of the ventricular assist device, initially distal coupling portion 31 is coupled to a distal bearing housing 118H (shown in FIG. 5A), e.g., via a snap-fit mechanism. For some applications proximal strut junctions 33 are still maintained in open states at this stage, in order for the impeller to be placed within the frame via the proximal end of the frame. Typically, the structure of frame 34 shown in FIG. 2 is used in applications in which pump-outlet tube extends to the distal end of frame 34 (e.g., as shown in FIG. 1B). In such cases, the impeller cannot be inserted via the distal end of the frame, since the distal end of the frame is covered by pump-outlet tube 24. During the assembly of the ventricular assist device, subsequent to the impeller being inserted via the proximal end of the frame, the proximal strut junctions are closed. For some applications, the proximal strut junctions are closed around the outside of a proximal bearing housing 116H (shown in FIG. 5A), as described in further detail hereinbelow with reference to FIGS. 5A-B. Typically, a securing element 117 (e.g., a ring shown in FIG. 5A) holds the strut junctions in their closed configurations around the outside of proximal bearing housing 116H.

Typically, when disposed in its non-radially constrained configuration, frame 34 has a total length of more than 25 mm (e.g., more than 30 mm), and/or less than 50 mm (e.g., less than 45 mm), e.g., 25-50 mm, or 30-45 mm. Typically, when disposed in its radially-constrained configuration (within delivery catheter 143), the length of the frame increases by between 2 and 5 mm. Typically, when disposed in its non-radially constrained configuration, the central cylindrical portion of frame 34 has a length of more than 10 mm (e.g., more than 12 mm), and/or less than 25 mm (e.g., less than 20 mm), e.g., 10-25 mm, or 12-20 mm. For some applications, a ratio of the length of the central cylindrical portion of the frame to the total length of the frame is more than 1:4 and/or less than 1:2, e.g., between 1:4 and 1:2.

Figures 3A, 3B, 3C:
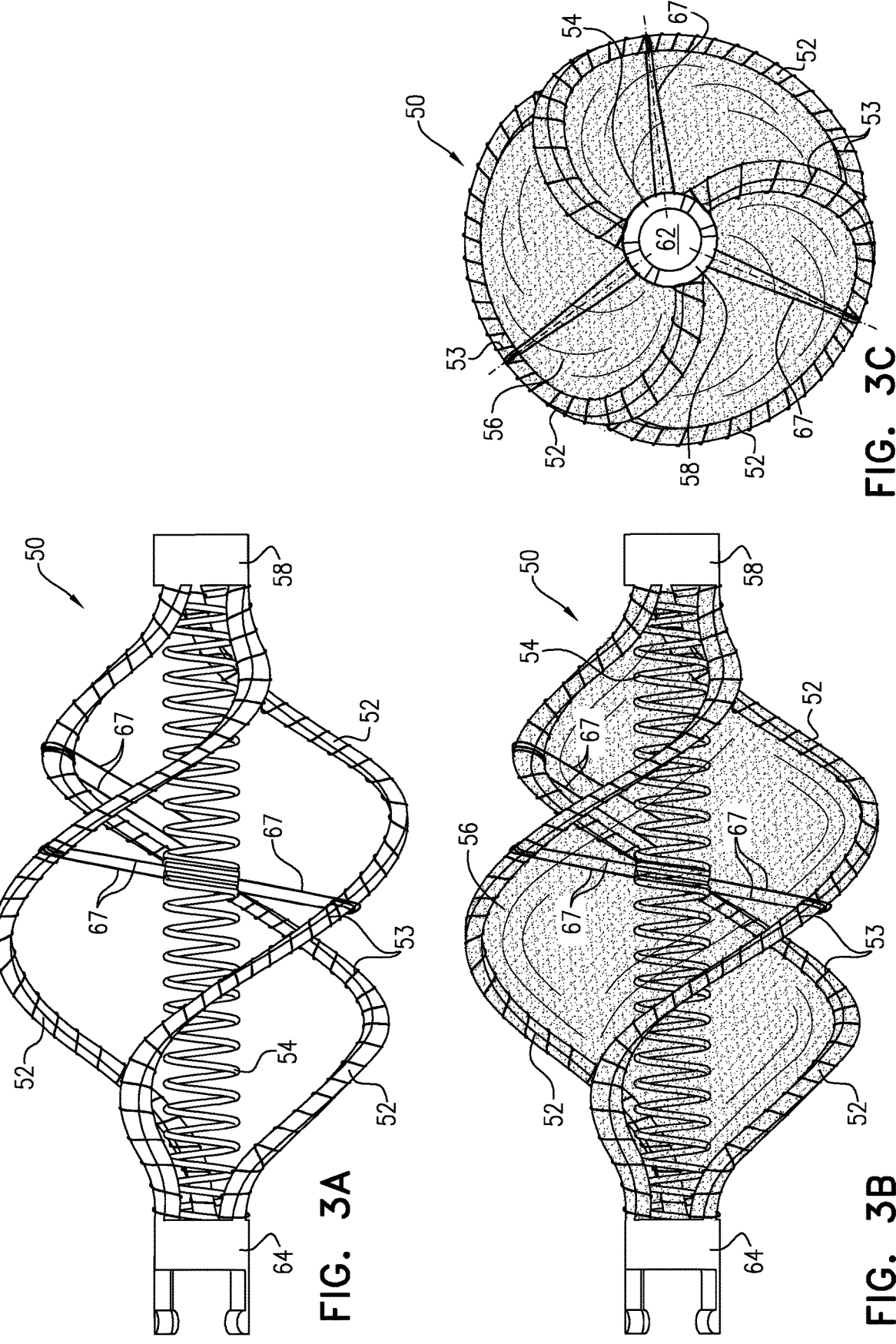
FIGS. 3A, 3B, 3C, 3D, and 3E are schematic illustrations of an impeller of a ventricular assist device or portions thereof, in accordance with some applications of the present invention.
Figure 3E:
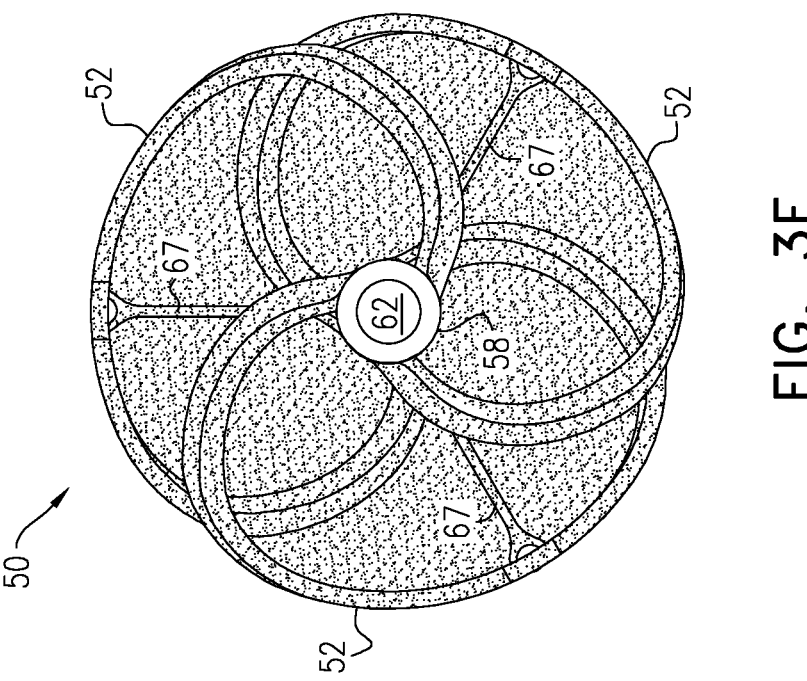
Figure 3D:
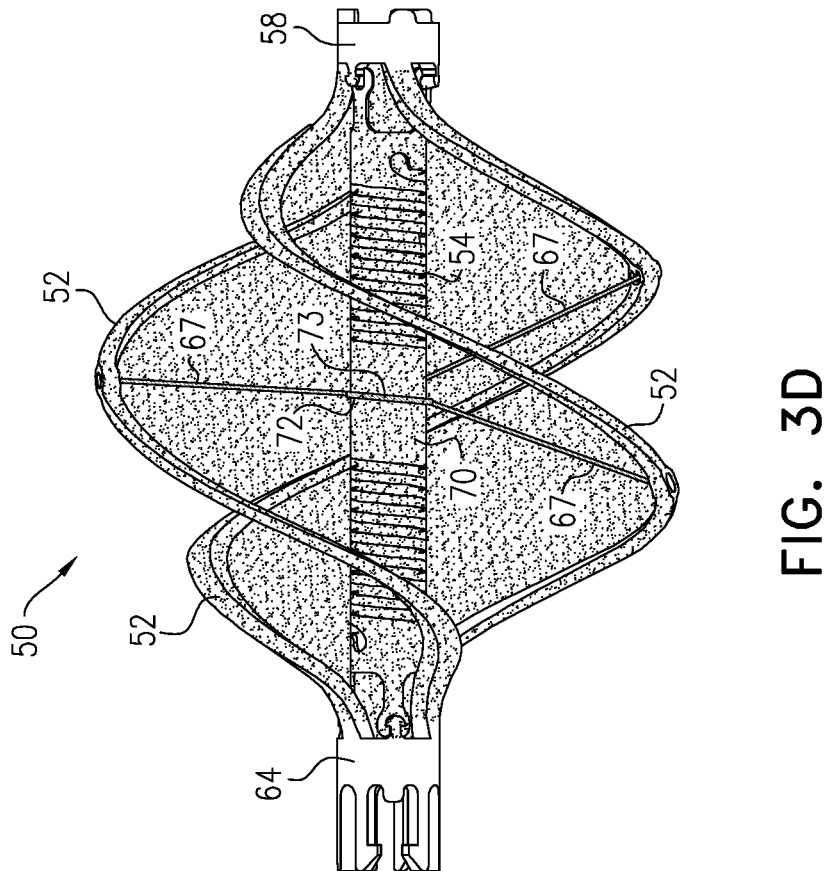

Reference is now made to FIGS. 3A-E, which are schematic illustrations of impeller 50 or portions thereof, in accordance with some applications of the present invention. Typically, the impeller includes at least one outer helical elongate element 52, which winds around a central axial spring 54, such that the helix defined by the helical elongate element is coaxial with the central axial spring. Typically, the impeller includes two or more helical elongate elements (e.g., three helical elongate elements, as shown in FIGS. 3A-C). For some applications, the helical elongate elements and the central axial spring are made of a shape-memory material, e.g., a shape-memory alloy, such as nitinol. Typically, each of the helical elongate elements and the central axial spring support a film 56 of a material (e.g., an elastomer, such as polyurethane, and/or silicone) therebetween. For some applications, the film of material includes pieces of nitinol embedded therein, for example in order to strengthen the film of material. For illustrative purposes, the impeller is shown in the absence of the material in FIG. 3A. FIGS. 3B and 3C show respective views of the impeller with the material supported between the helical elongate elements and the spring. FIGS. 3D and 3E show similar respective views of the impeller to those shown in FIGS. 3B and 3C, but with certain features of the impeller differing from those shown in FIGS. 3B and 3C, as elaborated upon hereinbelow.

Each of the helical elongate elements, together with the film extending from the helical elongate element to the spring, defines a respective impeller blade, with the helical elongate elements defining the outer edges of the blades, and the axial spring defining the axis of the impeller. Typically, the film of material extends along and coats the spring. For some applications, sutures 53 (e.g., polyester sutures, shown in FIGS. 3A-C) are wound around the helical elongate elements. Typically, the sutures are configured to facilitate bonding between the film of material (which is typically an elastomer, such as polyurethane, or silicone) and the helical elongate element (which is typically a shape-memory alloy, such as nitinol). For some applications, sutures (e.g., polyester sutures, not shown) are wound around spring 54. Typically, the sutures are configured to facilitate bonding between the film of material (which is typically an elastomer, such as polyurethane, or silicone) and the spring (which is typically a shape-memory alloy, such as nitinol).

Typically, proximal ends of spring 54 and helical elongate elements 52 extend from a proximal bushing (i.e., sleeve bearing) 64 of the impeller, such that the proximal ends of spring 54 and helical elongate elements 52 are disposed at a similar radial distance from the longitudinal axis of the impeller, as each other. Similarly, typically, distal ends of spring 54 and helical elongate elements 52 extend from a distal bushing 58 of the impeller, such that the distal ends of spring 54 and helical elongate elements 52 are disposed at a similar radial distance from the longitudinal axis of the impeller, as each other. The helical elongate elements typically rise gradually from the proximal bushing before reaching a maximum span and then falling gradually toward the distal bushing. Typically, the helical elongate elements are symmetrical along their lengths, such that the rising portions of their lengths are symmetrical with respect to the falling portions of their lengths. Typically, the impeller defines a lumen 62 therethrough (shown in FIG. 3C), with the lumen typically extending through, and being defined by, spring 54, as well as proximal bushing 64 and distal bushing 58, of the impeller.

Figure 4:
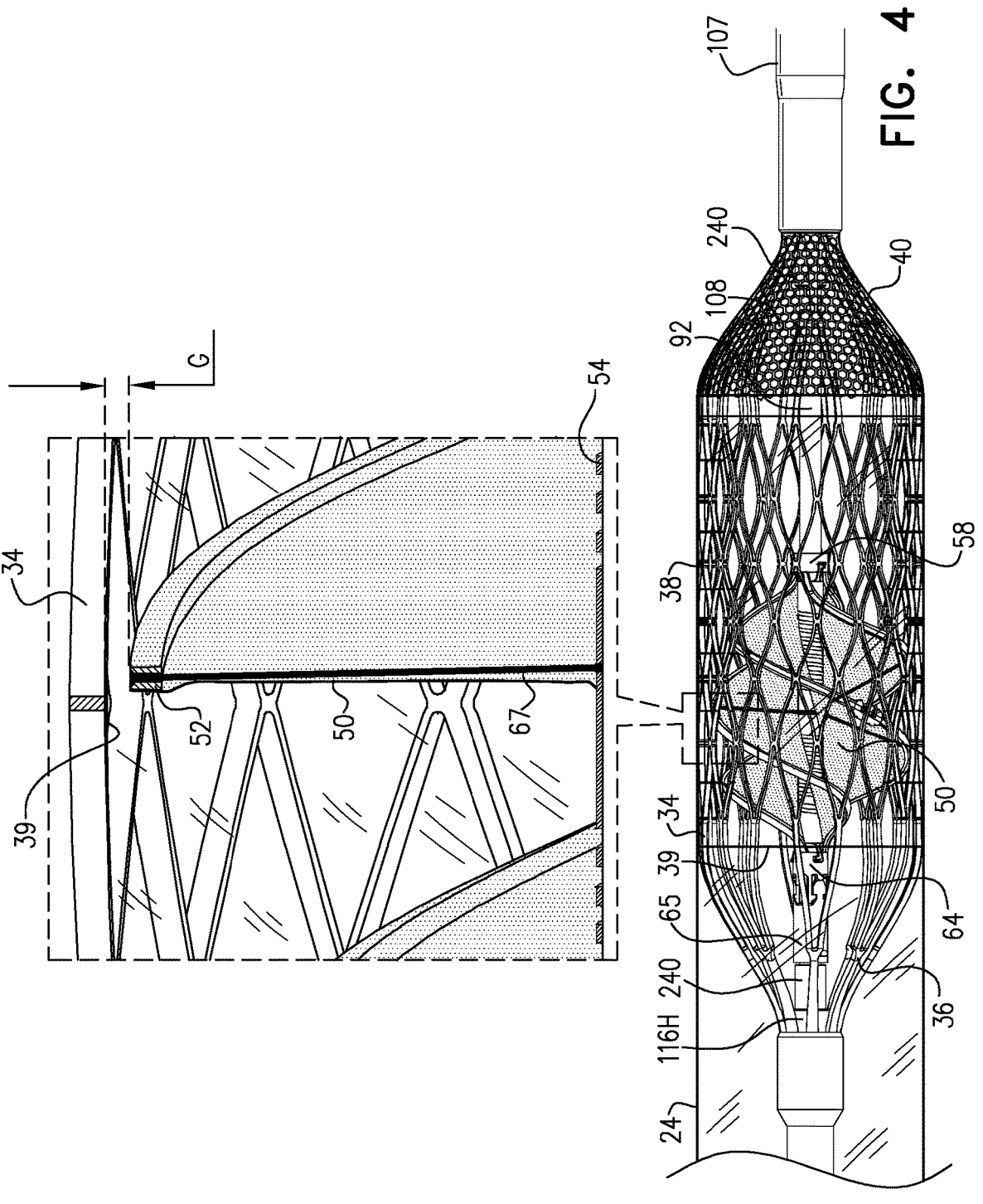
FIG. 4 is a schematic illustration of an impeller disposed inside a frame of a ventricular assist device, in accordance with some applications of the present invention.

Reference is now made to FIG. 4, which is a schematic illustration of impeller 50 disposed inside frame 34 of ventricular assist device 20, in accordance with some applications of the present invention. For some applications, within at least a portion of frame 34 (e.g., along all of, or a portion of, central cylindrical portion 38 of the frame), inner lining 39 lines the frame. In accordance with respective applications, the inner lining partially overlaps or fully overlaps with pump-outlet tube 24 over the portion of the frame that the inner lining lines, as described in further detail hereinbelow with reference to FIGS. 9A-B.

As shown in FIG. 4, typically there is a gap G, between the outer edge of impeller 50 and inner lining 39, even at a location at which the span of the impeller is at its maximum. For some applications, it is desirable that the gap between the outer edge of the blade of the impeller and inner lining 39 be relatively small, in order for the impeller to efficiently pump blood from the subject's left ventricle into the subject's aorta. (It is noted that, by virtue of the relatively small gap between the outer edge of impeller 50 and inner lining 39 even at a location at which the span of the impeller is at its maximum, as well as the shape of the impeller, the impeller functions as an axial-flow impeller, with the impeller pumping blood in the axial direction from a distal end of pump-outlet tube 24 to the proximal end of the pump-outlet tube.) It is also desirable that a gap between the outer edge of the blade of the impeller and the inner surface of frame 34 be maintained throughout the rotation of the impeller within frame 34, for example, in order to reduce the risk of hemolysis.

For some applications, when impeller 50 and frame 34 are both disposed in non-radially-constrained configurations and prior to operation of the impeller, gap G between the outer edge of the impeller and the inner lining 39, at the location at which the span of the impeller is at its maximum, is greater than 0.05 mm (e.g., greater than 0.1 mm), and/or less than 1 mm (e.g., less than 0.4 mm), e.g., 0.05-1 mm, or 0.1-0.4 mm. For some applications, when the impeller is disposed in its non-radially-constrained configurations and prior to operation of the impeller, the outer diameter of the impeller at the location at which the outer diameter of the impeller is at its maximum is more than 7 mm (e.g., more than 8 mm), and/or less than 10 mm (e.g., less than 9 mm), e.g., 7-10 mm, or 8-9 mm. For some applications, when frame 34 is disposed in its non-radially-constrained configuration, the inner diameter of frame 34 (as measured from the inside of inner lining 39 on one side of the frame to the inside of inner lining on the opposite side of the frame) is greater than 7.5 mm (e.g., greater than 8.5 mm), and/or less than 10.5 mm (e.g., less than 9.5 mm), e.g., 7.5-10.5 mm, or 8.5-9.5 mm. For some applications, when the frame is disposed in its non-radially-constrained configuration, the outer diameter of frame 34 is greater than 8 mm (e.g., greater than 9 mm), and/or less than 13 mm (e.g., less than 12 mm), e.g., 8-13 mm, or 9-12 mm.

Typically, an axial shaft 92 passes through the axis of impeller 50, via lumen 62 of the impeller. Further typically, the axial shaft is rigid, e.g., a rigid tube. For some applications, proximal bushing 64 of the impeller is coupled to the shaft such that the axial position of the proximal bushing with respect to the shaft is fixed, and distal bushing 58 of the impeller is slidable with respect to the shaft. For example, the proximal bushing may be coupled to a coupling element 65 disposed on the axial shaft (shown in FIG. 4), for example via a snap-fit mechanism. (Alternatively, distal bushing 58 of the impeller is coupled to the shaft such that the axial position of the distal bushing with respect to the shaft is fixed, and proximal bushing 64 of the impeller is slidable with respect to the shaft.) The axial shaft itself is radially stabilized via a proximal radial bearing 116 and a distal radial bearing 118. In turn, the axial shaft, by passing through lumen 62 defined by the impeller, radially stabilizes the impeller with respect to the inner surface of frame 34, such that even a relatively small gap between the outer edge of the blade of the impeller and the inner surface of frame 34 (e.g., a gap that is as described above) is maintained, during rotation of the impeller.

Referring again to FIGS. 3A-C, for some applications, the impeller includes a plurality of elongate elements 67 extending radially from central axial spring 54 to outer helical elongate elements 52. The elongate elements are typically flexible but are substantially non-stretchable along the axis defined by the elongate elements. Further typically, each of the elongate elements is configured not to exert force upon the helical elongate element, unless force is acting upon the impeller that is causing the helical elongate element to move radially outward, such that (in the absence of the elongate element) a separation between the helical elongate element and the central axial spring would be greater than a length of the elongate element. For example, the elongate elements may include strings (such as polyester, and/or another polymer or a natural material that contains fibers) and/or wires (such as nitinol wires, and/or wires made of a different alloy, or a metal).

For some applications, the elongate elements 67 maintain helical elongate element 52 (which defines the outer edge of the impeller blade) within a given distance with respect to the central axial spring. In this manner, the elongate elements are configured to prevent the outer edge of the impeller from being forced radially outward due to forces exerted upon the impeller during the rotation of the impeller. The elongate elements are thereby configured to maintain the gap between the outer edge of the blade of the impeller and the inner surface of frame 34, during rotation of the impeller. Typically, more than one (e.g., more than two) and/or fewer than eight (e.g., fewer than four) elongate elements 67 are used in the impeller, with each of the elongate elements typically being doubled (i.e., extending radially from central axial spring 54 to an outer helical elongate element 52, and then returning from the helical elongate element back to the central axial spring). For some applications, a plurality of elongate elements, each of which extends from the spring to a respective helical elongate element and back to the spring, are formed from a single piece of string or a single wire.

Reference is now made to FIGS. 3D and 3E, which are schematic illustrations of impeller 50, the impeller including a single integrated impeller-overexpansion-prevention element 72 that defines a plurality of elongate elements 67, in accordance with some applications of the present invention. For some applications, impeller-overexpansion-prevention element 72 (which defines a plurality of elongate elements 67) is used as an alternative to elongate elements 67 as shown in FIGS. 3A-C. For some applications, element 72 defines a ring 73 and the plurality of elongate elements 67 extending radially from the ring. For some applications, rather than threading strings and/or wire around spring 54, ring 73 of element 72 is placed around the spring, e.g., by being placed around tube 70, which is typically disposed at the longitudinally-central location of the spring. The ends of respective elongate elements 67 are then coupled to respective helical elongate elements 52. As described hereinabove, elongate elements 67 are typically flexible but are substantially non-stretchable along the axis defined by the elongate elements. Further typically, each of elongate elements 67 is configured to substantially not resist compression. Rather, each elongate element 67 is configured to exert a tensile force upon helical elongate element 52 that prevents helical elongate element 52 from moving radially outward, such that (in the absence of elongate element 67) a separation between helical elongate element 52 and central axial spring 54 would be greater than a length of elongate element 67. When a force is acting upon the impeller that would cause the helical elongate element 52 to move radially outward (in the absence of elongate element 67), the impeller-overexpansion-prevention element is configured to prevent radial expansion of the impeller. Typically, a respective elongate element 67 is disposed within each one of the impeller blades and is configured to prevent the impeller blade from radially expanding. For some applications, element 72 is made of polyester, and/or another polymer or a natural material that contains fibers, and/or nitinol (or a similar shape-memory alloy).

It is noted that the scope of the present application includes using single integrated impeller-overexpansionprevention element 72 with an impeller having a different construction from that shown in FIGS. 3D-E. For example, the single integrated impeller-overexpansion-prevention element 72 could be used with an impeller having a differently constructed axial structure than spring 54. Typically, the axial structure defines a lumen therethrough, such that the impeller defines lumen 62 therethrough.

For some applications, the following assembly technique is used to manufacture the impeller while enhancing bonding of an elastomeric material that is used to form film 56 to the at least one helical elongate element. Typically, bonding of the elastomeric material to the at least one helical elongate element is performed in a manner that does not cause a protrusion from the effective edge of the impeller blade. Further typically, bonding of the elastomeric material to the at least one helical elongate element is performed in a manner that provides the impeller blade with a rounded outer edge, by the elastomeric material rounding edges of the helical elongate element. Proximal bushing 64, distal bushing 58, and helical elongate elements 52 are cut from a tube of shape-memory material, such as nitinol. The cutting of the tube, as well as the shape setting of the shape-memory material, is typically performed such that the helical elongate elements and the bushings are defined by a tube of shape-memory material that is cut and shape set. For some applications, prior to being coupled to spring 54, a plasma treatment is applied to the helical elongate elements. Alternatively or additionally, prior to being coupled to spring 54, the helical elongate elements are coated with a coupling agent. Typically, a coupling agent is selected that has at least two functional groups that are configured to bond respectively with the helical elongate elements and with the elastomeric material. For example, a silane compound, such as n-(2-aminoethyl)-3-aminopropyltrimethoxysilane, may be used, with the silane compound containing a first functional group (e.g., (OH)) which is configured to bond with the helical elongate elements (which are typically made of an alloy, such a nitinol), and the silane compound containing a second functional group (e.g., (NH2)) which is configured to bond with the elastomeric material. Typically, the functional groups in the coupling agent are only active for a given time period (e.g., approximately an hour or less). Therefore, during this time period, a coat of elastomeric material is applied around the helical elongate elements. Typically, the coat of elastomeric material is the same elastomeric material or a similar elastomeric material to that used in film 56. For example, a polycarbonate-based thermoplastic polyurethane, such as Aromatic Carbothane™ (e.g., Aromatic Carbothane™ 75A) may be used in film 56, and the coating may be the same polycarbonate-based thermoplastic polyurethane, or a similar polycarbonate-based thermoplastic polyurethane, such as Pellethane® (e.g., Pellethane® 90A).

As described hereinabove, proximal bushing 64, distal bushing 58, and helical elongate elements 52 are typically cut from a tube of shape-memory material, such as nitinol. For some applications, subsequent to the coating having been applied to the helical elongate elements 52, spring 54 is coupled to the helical elongate elements. Typically, spring 54 is inserted into the cut and shape-set tube, such that the spring extends along the length of the tube from at least the proximal bushing to the distal bushing. For some applications, the spring is inserted into the cut and shape-set tube while the spring is in an axially compressed state, and the spring is configured to be held in position with respect to the tube, by exerting a radial force upon the proximal and distal bushings. Alternatively or additionally, portions of the spring are welded to the proximal and distal bushings. For some applications, the spring is cut from a tube of a shape-memory material, such as nitinol. For some such applications, the spring is configured such that, when the spring is disposed in a non-radially-constrained configuration (in which the spring is typically disposed during operation of the impeller), there are substantially no gaps between windings of the spring and adjacent windings thereto.

Typically, at this stage, overexpansion-prevention element 72 is placed between the spring and the helical elongate elements, as described hereinabove, such that an assembly is formed that includes coated helical elongate elements 52, spring 54, and overexpansion-prevention element 72.

For some applications, at this stage, the assembly of coated helical elongate elements 52, spring 54, and overexpansion-prevention element 72, is sprayed with a further layer of an elastomeric material. Typically, the elastomeric material that is sprayed is the same elastomeric material or a similar elastomeric material to that used as film 56. For example, a polycarbonate-based thermoplastic polyurethane, such as Aromatic Carbothane™ (e.g., Aromatic Carbothane™ 75A) may be used as film 56, and the sprayed material may be the same polycarbonate-based thermoplastic polyurethane, or a similar polycarbonate-based thermoplastic polyurethane, such as Pellethane® (e.g., Pellethane® 90A). For some applications, applying the spray to the helical elongate elements rounds the helical elongate elements. Typically, when the helical elongate element has a rounded cross section, the elastomeric material forms a layer having a substantially uniform thickness at the interface with the helical elongate element. For some applications, the step of applying the coat of elastomeric material to the helical elongate elements as described above, at least partially rounds the helical elongate elements.

For some applications, subsequent to the spray having been applied, the assembly of coated helical elongate elements 52, spring 54, and overexpansion-prevention element 72 is dipped in the elastomer from which film 56 is made. For some applications, the material from which the film is made is an elastomer having an ultimate elongation of more than 300 percent, e.g., more than 400 percent. Typically, the material has a relatively low molecular weight. For some applications, the material has a melt flow index (which is an indirect measure of molecular weight) of at least 4, e.g., at least 4.3. For some applications, the material has an ultimate tensile strength of more than 6000 psi, e.g., more than 7000 psi, or more than 7500 psi. For some applications, the material is a polycarbonate-based thermoplastic polyurethane, e.g., a Carbothane™. For some applications, Aromatic Carbothane™ (e.g., Aromatic Carbothane™ 75A) is used. Typically, such materials combine one or more of the following properties: no outer diameter loss caused during the dip process, resistance to fatigue, resistance to becoming misshaped by being crimped, and low outer diameter loss during crimping. Subsequently, the material is cured such that it solidifies, e.g., by being left to dry. Typically, during this stage, the impeller is disposed on a mandrel, such that the mandrel passes through lumen 62 defined by the bushings and the spring, thereby maintaining the lumen during the drying. For some applications, while the material from which the film is made is drying, the impeller is rotated, which typically facilitates the formation of a film of material having a substantially uniform thickness within each of the impeller blades. Once the material has dried, the mandrel is typically removed from lumen 62.

In accordance with the above description of the application of film 56 to the helical elongate elements, the scope of the present invention includes any technique whereby, prior to the helical elongate elements being dipped into the elastomeric material from which film 56 is made, additional layers of the same elastomeric material, a different elastomeric material, and/or a mediating material are applied to the helical elongate elements, whether by spraying, dipping, or a different coating method. For some applications, additional layers of elastomeric material are configured to round the helical elongate elements, and/or to act as mediators to enhance bonding between the helical elongate elements and film 56 of material. For some applications, a mediating material (such as silane) is configured to act as a mediator to enhance bonding between the helical elongate elements and film 56 of material.

Typically, impeller 50 is inserted into the left ventricle transcatheterally, while impeller 50 is in a radially-constrained configuration. In the radially-constrained configuration, both helical elongate elements 52 and central axial spring 54 become axially elongated, and radially constrained. Typically film 56 of the material (e.g., silicone and/or polyurethane) changes shape to conform to the shape changes of the helical elongate elements and the axial support spring, both of which support the film of material. Typically, using a spring to support the inner edge of the film allows the film to change shape without the film becoming broken or collapsing, due to the spring providing a large surface area to which the inner edge of the film bonds. For some applications, using a spring to support the inner edge of the film reduces a diameter to which the impeller can be radially constrained, relative to if, for example, a rigid shaft were to be used to support the inner edge of the film, since the diameter of the spring itself can be reduced by axially elongating the spring.

As described hereinabove, for some applications, proximal bushing 64 of impeller 50 is coupled to axial shaft 92 such that the axial position of the proximal bushing with respect to the shaft is fixed, and distal bushing 58 of the impeller is slidable with respect to the shaft. For example, the proximal bushing may be coupled to coupling element 65 disposed on the axial shaft (shown in FIG. 4), for example via a snap-fit mechanism. For some applications, when the impeller is radially constrained for the purpose of inserting the impeller into the ventricle or for the purpose of withdrawing the impeller from the subject's body, the impeller axially elongates by the distal bushing sliding along the axial shaft distally. Alternatively (not shown), distal bushing 58 of the impeller is coupled to the shaft such that the axial position of the distal bushing with respect to the shaft is fixed, and proximal bushing 64 of the impeller is slidable with respect to the shaft. For some such applications, when the impeller is radially constrained for the purpose of inserting the impeller into the ventricle or for the purpose of withdrawing the impeller from the subject's body, the impeller axially elongates by the proximal bushing sliding along the axial shaft proximally. Subsequent to being released inside the subject's body, the impeller assumes its non-radially-constrained configuration (in which the impeller is typically disposed during operation of the impeller), which is as shown in FIGS. 3A-E.

Figures 5A, 5B:
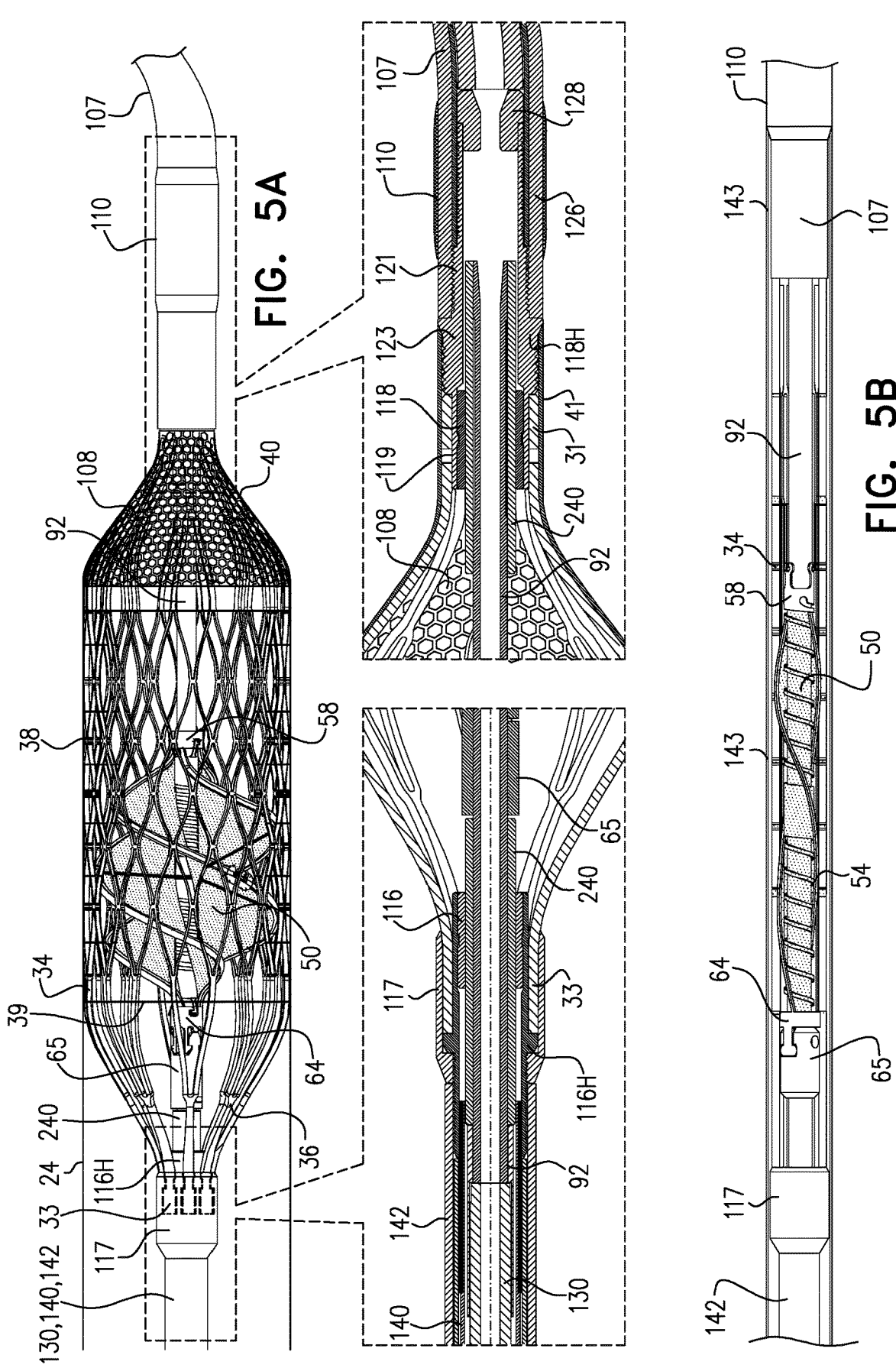
FIGS. 5A and 5B are schematic illustrations of the impeller and the frame of the ventricular assist device, respectively in non-radially-constrained and radially-constrained states thereof, in accordance with some applications of the present invention.

Reference is now made to FIGS. 5A and 5B, which are schematic illustrations of impeller 50 and frame 34 of ventricular assist device 20, respectively in non-radially-constrained and radially-constrained states thereof, in accordance with some applications of the present invention. The impeller and the frame are typically disposed in the radially-constrained states during the transcatheteral insertion of the impeller and the frame into the subject's body, and are disposed in the non-radially-constrained states during operation of the impeller inside the subject's left ventricle.

As indicated in FIG. 5B, the frame and the impeller are typically maintained in radially-constrained configurations by delivery catheter 143. Typically, in the radially-constrained configuration of the impeller, the impeller has a total length of more than 15 mm (e.g., more than 20 mm), and/or less than 30 mm (e.g., less than 25 mm), e.g., 15-30 mm, or 20-25 mm. Further typically, in the non-radially constrained configuration of the impeller, the impeller has a length of more than 8 mm (e.g., more than 10 mm), and/or less than 18 mm (e.g., less than 15 mm), e.g., 8-18 mm, or 10-15 mm. Still further typically, when the impeller and frame 34 are disposed in radially-constrained configurations (as shown in FIG. 5B), the impeller has an outer diameter of less than 2 mm (e.g., less than 1.6 mm) and the frame has an outer diameter of less than 2.5 mm (e.g., less than 2.1 mm).

As described hereinabove, typically, axial shaft 92 passes through the axis of impeller 50, via lumen 62 of the impeller. Typically, proximal bushing 64 of the impeller is coupled to the shaft via a coupling element 65 such that the axial position of the proximal bushing with respect to the shaft is fixed, and distal bushing 58 of the impeller is slidable with respect to the shaft. (Alternatively, distal bushing 58 of the impeller is coupled to the shaft such that the axial position of the distal bushing with respect to the shaft is fixed, and proximal bushing 64 of the impeller is slidable with respect to the shaft.) The axial shaft itself is radially stabilized via a proximal radial bearing 116 and a distal radial bearing 118. Typically, proximal bearing housing 116H is disposed around, and houses, the proximal bearing, and distal bearing housing 118H is disposed around, and houses, the distal bearing. For some such applications, the radial bearings and the bearing housings are made of respective, different materials from each other. For example, the radial bearings may be made of a first material that has a relatively high hardness, such as ceramic (e.g., zirconia), and the bearing housings may be made of a second material that is moldable into a desired shape, such as a metal or an alloy (e.g., stainless steel, cobalt chromium, and/or nitinol).

For some applications, axial shaft 92 is made of a metal or an alloy, such as stainless steel. For some such applications, the axial shaft covered with ceramic sleeves 240 (e.g., zirconia sleeves) along regions of the axial shaft that come into contact with either of the proximal and distal bearings 116, 118 during operation of the ventricular assist device. In this manner, the radial interfaces between the axial shaft and the proximal and distal bearings is a ceramic-ceramic interface. As described in further detail herein, typically, the impeller and the axial shaft are configured to undergo axial back-and-forth motion during operation of the ventricular assist device. Therefore, for some applications, at locations along the axial shaft corresponding to each of the proximal and distal bearing, the axial shaft is covered with the ceramic sleeve along a length of more than 5 mm, e.g., more than 7 mm. In this manner, over the course of the axial back-and-forth motion of the axial shaft, the regions of the axial shaft that are in contact with the radial bearings are covered with the ceramic sleeves.

For some applications, the proximal bearing housing 116H and distal bearing housing 118H perform additional functions. Referring first to the proximal bearing housing, as described hereinabove, for some applications, proximal strut junctions 33 of frame 34 are closed around the outside of the proximal bearing housing. For some applications, the outer surface of the proximal bearing housing defines groves that are shaped such as to receive the proximal strut junctions. For example, as shown, the proximal strut junctions have widened heads, and the outer surface of the proximal bearing housing defines groves that are shaped to conform with the widened heads of the proximal strut junctions. Typically, securing element 117 (which typically includes a ring) holds the strut junctions in their closed configurations around the outside of proximal bearing housing 116H. For some applications, additional portions of the ventricular assist device are coupled to the proximal bearing housing. For some applications, a drive cable 130 extends from outside the subject's body to axial shaft 92, and is coupled to the axial shaft. Typically the drive cable rotates within a first outer tube 140, which functions as a drive-cable bearing tube, and which extends from outside the subject's body to the proximal bearing housing. For some applications, the first outer tube is disposed within a second outer tube 142, which also extends from outside the subject's body to the proximal bearing housing. For some applications, first outer tube 140 and/or second outer tube 142 is coupled to the proximal bearing housing (e.g., using an adhesive). For example, first outer tube 140 may be coupled to an inner surface of the proximal bearing housing, and second outer tube 142 may be coupled to an outer surface of the proximal bearing housing.

Referring now to distal bearing housing 118H, for some applications, distal coupling portion 31 of frame 34 is coupled to an outer surface of distal bearing housing 118H, e.g., via a snap-fit mechanism. For example, the outer surface of a proximal-most portion 119 of the distal bearing housing may include a snap-fit mechanism to which distal coupling portion 31 of frame 34 is coupled. For some applications, distal bearing 118 is disposed within the proximal-most portion 119 of the distal bearing housing, as shown in FIG. 5A. As described hereinabove, for some applications, pump-outlet tube 24 extends to the distal end of frame 34 and defines lateral blood-inlet openings 108. For some such applications, a coupling portion 41 (e.g., a tubular coupling portion) extends distally from the pump-outlet tube, and the coupling portion is coupled to the distal bearing housing in order to anchor the distal end of the pump-outlet tube. For some applications, an intermediate portion 123 of the distal bearing housing defines a ridged or a threaded outer surface, to which coupling portion 41 of the pump-outlet tube is coupled (e.g., via adhesive). For some applications, the outer surface is ridged in order to enhance bonding between the distal bearing housing and coupling portion 41 of the pump-outlet tube. For some applications, the outer surface is threaded in order to enhance bonding between the distal bearing housing and coupling portion 41 of the pump-outlet tube and to facilitate the application of adhesive between the outer surface and coupling portion 41 of the pump-outlet tube, as described in further detail hereinbelow with reference to FIG. 12B. For some applications, a distal portion 121 of the distal bearing housing is configured to stiffen a region of distal-tip element 107 into which the distal end of shaft 92 moves (e.g., axial-shaft-receiving tube 126, or a portion thereof). Typically, distal-tip element 107 is coupled to an outer surface of distal portion 121 of the distal bearing housing (e.g., via adhesive). For some applications, at least a portion of the outer surface of distal portion 121 of the distal bearing housing is ridged and/or threaded in order to enhance bonding between distal-tip element 107 and the distal bearing housing.

As described above, axial shaft 92 is radially stabilized via proximal radial bearing 116 and distal radial bearing 118. In turn, the axial shaft, by passing through lumen 62 defined by the impeller, radially stabilizes the impeller with respect to the inner surface of frame 34 and inner lining 39, such that even a relatively small gap between the outer edge of the blade of the impeller and inner lining 39 (e.g., a gap that is as described above) is maintained, during rotation of the impeller, as described hereinabove. Typically, the impeller itself is not directly disposed within any radial bearings or thrust bearings. Rather, bearings 116 and 118 act as radial bearings with respect to the axial shaft. Typically, pump-head portion 27 (and more generally ventricular assist device 20) does not include any thrust bearing that is configured to be disposed within the subject's body and that is configured to oppose thrust generated by the rotation of the impeller. For some applications, one or more thrust bearings are disposed outside the subject's body (e.g., within motor unit 23, shown in FIGS. 1A, 7, and 8A-B), and opposition to thrust generated by the rotation of the impeller is provided solely by the one or more thrust bearings disposed outside the subject's body. For some applications, a mechanical element and/or a magnetic element is configured to maintain the impeller within a given range of axial positions. For example, a magnet (e.g., magnet 82, described hereinbelow with reference to FIG. 7) that is disposed at the proximal end of the drive cable (e.g., outside the subject's body) may be configured to impart axial motion to the impeller, and/or to maintain the impeller within a given range of axial positions.

Figures 6A, 6B:
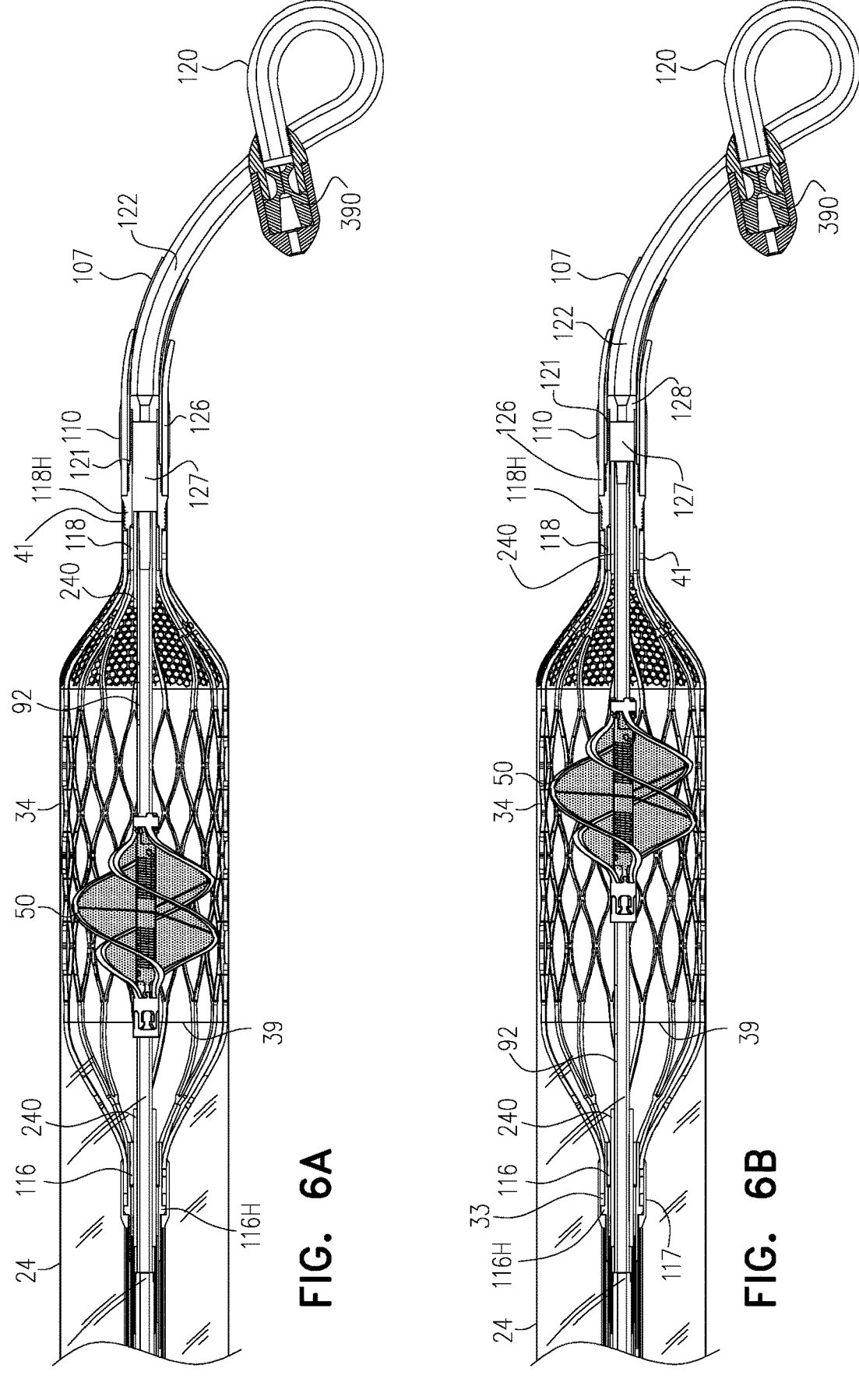
FIGS. 6A and 6B are schematic illustrations of a ventricular assist device at respective stages of a motion cycle of the impeller of the ventricular assist device with respect to the frame of the ventricular assist device, in accordance with some applications of the present invention.

Reference is now made to FIGS. 6A and 6B, which are schematic illustrations of ventricular assist device 20 at respective stages of a motion cycle of impeller 50 of the ventricular assist device with respect to frame 34 of the ventricular assist device, in accordance with some applications of the present invention. For some applications, while the impeller is pumping blood through tube 24 by rotating, axial shaft 92 (to which the impeller is fixated) is driven to move the impeller axially back-and-forth within frame 34, by the axial shaft moving in an axial back-and-forth motion, as described in further detail hereinbelow with reference to FIG. 7. Alternatively or additionally, the impeller and the axial shaft are configured to move axially back-and-forth within frame 34 in response to forces that are acting upon the impeller, and without requiring the axial shaft to be actively driven to move in the axial back-and-forth motion. Typically, over the course of the subject's cardiac cycle, the pressure difference between the left ventricle and the aorta varies from being approximately zero during ventricular systole (hereinafter "systole") to a relatively large pressure difference (e.g., 50-70 mmHg) during ventricular diastole (hereinafter "diastole"). For some applications, due to the increased pressure difference that the impeller is pumping against during diastole (and due to the fact that drive cable 130 is stretchable), the impeller is pushed distally with respect to frame 34 during diastole, relative to the location of the impeller with respect to frame 34 during systole. In turn, since the impeller is connected to the axial shaft, the axial shaft is moved forward. During systole, the impeller (and, in turn, the axial shaft) move back to their systolic positions. In this manner, the axial back-and-forth motion of the impeller and the axial shaft is generated in a passive manner, i.e., without requiring active driving of the axial shaft and the impeller, in order to cause them to undergo this motion. FIGS. 6A and 6B show the impeller and axial shaft disposed at respective positions within frame 34 during the above-described axial back-and-forth motion cycle.

For some applications, by moving in the axial back-and-forth motion, the portions of the axial shaft that are in contact with proximal bearing 116 and distal bearing 118 are constantly changing. For some such applications, in this manner, the frictional force that is exerted upon the axial shaft by the bearings is spread over a larger area of the axial shaft than if the axial shaft were not to move relative to the bearings, thereby reducing wear upon the axial shaft, ceteris paribus. Alternatively or additionally, by moving in the back-and-forth motion with respect to the bearing, the axial shaft cleans the interface between the axial shaft and the bearings from any residues, such as blood residues.

For some applications, at the proximal-most position of the impeller during its motion cycle, the proximal end of the impeller within the proximal conical section of frame 34. For some applications, at the distal-most position of the impeller during its motion cycle, the distal end of the impeller is disposed at the distal end of the cylindrical section of frame 34. Alternatively, even at the distal-most position of the impeller during its motion cycle, the distal end of the impeller is disposed proximal to the distal end of the cylindrical section of frame 34. Typically, over the course of the entire cardiac cycle, the section of the impeller at which the span of the impeller is at its maximum is disposed within the cylindrical portion of the frame 34. However, a proximal portion of the impeller is typically disposed within the proximal conical section of the frame during at least a portion of the cardiac cycle.

Reference is again made to FIGS. 6A and 6B. Typically, distal-tip element 107 is a single integrated element that includes both axial-shaft-receiving tube 126 and distal-tip portion 120. Typically, the axial-shaft receiving tube is configured to receive a distal portion of axial shaft 92 of the pump-head portion during axial back-and-forth motion of the axial shaft (as described in further detail hereinbelow), and/or during delivery of the ventricular assist device. (Typically, during delivery of the ventricular assist device, the frame is maintained in a radially-constrained configuration, which typically causes the axial shaft to be disposed in a different position with respect to the frame relative to its disposition with respect to the frame during operation of the ventricular assist device). For some applications, distal-tip portion 120 is configured to be soft, such that the distal-tip portion is configured not to injure tissue of the subject, even if the distal-tip portion comes into contact with the tissue (e.g., tissue of the left ventricle). For example, distal-tip portion 120 or the entire distal-tip element may be made of silicone, polyethylene terephthalate (PET) and/or polyether block amide (e.g., PEBAX®). For some applications, the distal-tip portion defines a lumen 122 therethrough. For some such applications, during insertion of the ventricular assist device into the left ventricle, guidewire 10 (FIG. 1B) is first inserted into the left ventricle, for example, in accordance with known techniques. The distal-tip portion of the ventricular assist device is then guided to the left ventricle by advancing the distal-tip portion over the guidewire, with the guidewire disposed inside lumen 122. For some applications, a duckbill valve 390 (or a different type of hemostasis valve) is disposed at the distal end of lumen 122 of distal-tip portion 120.

Typically, during the insertion of the ventricular assist device into the subject's ventricle, delivery catheter 143 is placed over impeller 50 and frame 34 and maintains the impeller and the frame in their radially-constrained configurations. For some applications, distal-tip element 107 extends distally from the delivery catheter during the insertion of the delivery catheter into the subject's ventricle, as shown in FIG. 1B. For some applications, toward the proximal end of the distal-tip element, the distal-tip element has a protrusion 110. Referring to FIG. 5B (which shows the pump-head portion disposed inside delivery catheter 143), for some applications, during the insertion of the ventricular assist device into the subject's ventricle, the delivery catheter extends until the proximal side of the protrusion, such that the delivery catheter and the protrusion form a smooth continuous surface. The distal side of protrusion 110 is tapered, such that the vasculature is exposed to a tapered diameter change, and is not exposed to any edges arising from a sharp change in diameter at the interface between the delivery catheter and the distal-tip element.

For some applications, distal-tip element 107 defines an overall curvature that is similar to that of a question mark or a tennis-racket, with the distal-tip element defining a straight proximal portion and a bulge on one side of the longitudinal axis of the straight proximal portion. Typically, the ventricular assist device is introduced into the subject's ventricle over a guidewire, as described hereinabove. Distal-tip portion 120 defines lumen 122, such that the distal-tip portion is held in a straightened configuration during the introduction of the ventricular assist device into the subject's ventricle (e.g., as shown in the left frame of FIG. 1B). For some applications, upon the guidewire being removed, distal-tip portion is configured to assume its curved shape. It is noted that the external shape of distal-tip portion in FIGS. 6A-B (as well as in some other figures) is shown as defining a complete loop, with the distal end of the distal-tip portion (within which duckbill valve 390 is disposed) crossing over a more proximal portion of the distal-tip portion. Typically, as a result of having had a guidewire inserted therethrough (during insertion of the ventricular assist device into the left ventricle), the distal-tip portion remains partially straightened, even after the removal of the guidewire from the distal-tip portion. Typically, the partial straightening of the distal-tip portion is such that, when the distal-tip portion is disposed within the left ventricle, in the absence of external forces acting upon the distal-tip portion, the distal-tip portion does not define a complete loop.

Referring again to FIGS. 6A-B, for some applications, axial-shaft-receiving tube 126 extends proximally from distal-tip portion 120 of distal-tip element 107. As described hereinabove, typically, the axial shaft undergoes axial back-and-forth motion during the operation of impeller 50. Axial-shaft-receiving tube 126 defines lumen 127, which is configured to receive the axial shaft when the axial shaft extends beyond distal bearing 118. For some applications, the axial shaft-receiving tube defines a stopper 128 at its distal end, the stopper being configured to prevent advancement of the axial shaft beyond the stopper. For some applications, the stopper comprises a rigid component that is inserted (e.g., embedded) into the distal end of the shaft-receiving tube. Alternatively (not shown), the stopper comprises a shoulder between lumen 127 of the axial-shaft-receiving tube and lumen 122 of distal-tip portion 120.

Typically, during normal operation of the impeller, the axial shaft does not come into contact with stopper 128, even when drive cable 130 (shown in FIG. 5A) is maximally elongated (e.g., during diastole). However, stopper 128 is configured to prevent the axial shaft from protruding into the tip portion when the delivery catheter is advanced over impeller 50 and frame 34, during retraction of ventricular assist device 20 from the subject's ventricle. In some cases, during the advancement of the delivery catheter over the frame and the impeller, the drive cable is at risk of snapping. In the absence of stopper 128, in such cases, the axial shaft may protrude into the tip portion. Stopper 128 prevents this from happening, even in the event that the drive cable snaps.

It is noted that, at the proximal end of frame 34, proximal radial bearing 116 also functions as a stopper, by preventing coupling element 65 and thereby preventing proximal bushing 64 of impeller 50 from being able to move beyond the proximal radial bearing. Typically, during normal operation of the impeller, coupling element 65 does not come into contact with proximal radial bearing 116. However, proximal radial bearing 116 is configured to prevent coupling element 65 and thereby prevent proximal bushing 64 of impeller 50 from migrating proximally from inside the frame, for example, when the impeller and the frame are held in radially-constrained (i.e., crimped) configurations inside delivery catheter 143.

Typically, during operation of the ventricular assist device, and throughout the axial back-and-forth motion cycle of the impeller, the impeller is disposed in relatively close proximity to the distal-tip portion. For example, the distance of the impeller to the distal-tip portion may be within the distal-most 50 percent, e.g., the distal-most 30 percent (or the distal-most 20 percent) of tube 24, throughout the axial back-and-forth motion cycle of the impeller.

Figure 7:
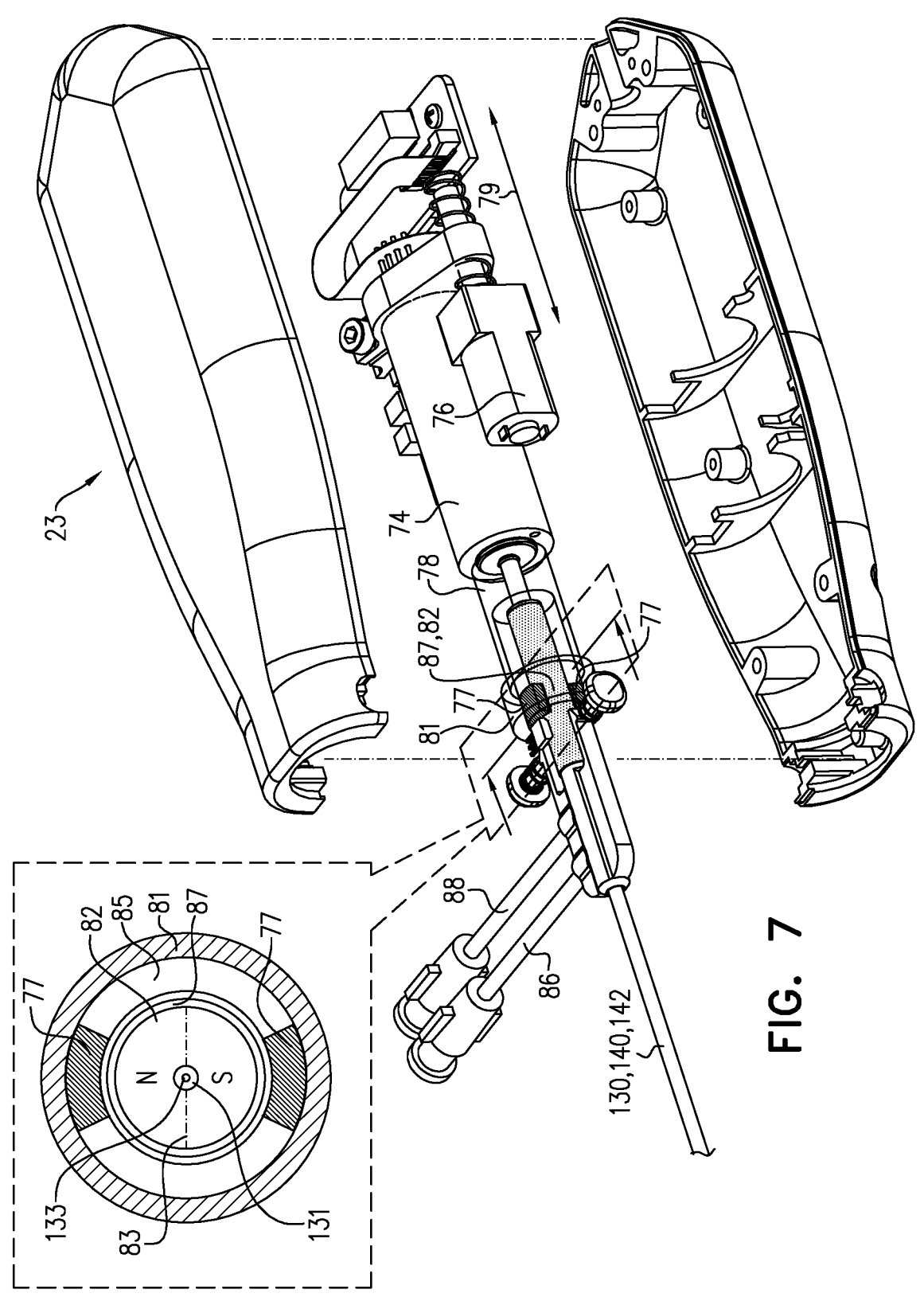
FIG. 7 is a schematic illustration of a motor unit of a ventricular assist device, in accordance with some applications of the present invention.

Reference is now made to FIG. 7, which is a schematic illustration of an exploded view of motor unit 23 of ventricular assist device 20, in accordance with some applications of the present invention. For some applications, computer processor 25 of control console 21 (FIG. 1A) that controls the rotation of impeller 50 is also configured to control the back-and-forth motion of the axial shaft. Typically, both types of motion are generated using motor unit 23. The scope of the present invention includes controlling the back-and-forth motion at any frequency. For some applications, an indication of the subject's cardiac cycle is detected (e.g., by detecting the subject's ECG), and the back-and-forth motion of the axial shaft is synchronized to the subject's cardiac cycle.

Typically, motor unit 23 includes a motor 74 that is configured to impart rotational motion to impeller 50, via drive cable 130. As described in further detail hereinbelow, typically, the motor is magnetically coupled to the drive cable. For some applications, an axial motion driver 76 is configured to drive the motor to move in an axial back-and-forth motion, as indicated by double-headed arrow 79. Typically, by virtue of the magnetic coupling of the motor to the drive cable, the motor imparts the back-and-forth motion to the drive cable, which it turn imparts this motion to the impeller. As described hereinabove and hereinbelow, for some applications, the drive cable, the impeller, and/or the axial shaft undergo axial back-and-forth motion in a passive manner, e.g., due to cyclical changes in the pressure gradient against which the impeller is pumping blood. Typically, for such applications, motor unit 23 does not include axial motion driver 76.

For some applications, the magnetic coupling of the motor to the drive cable is as shown in FIG. 7. As shown in FIG. 7, a set of driving magnets 77 are coupled to the motor via a driving magnet housing 78. For some applications, the driving magnet housing includes ring 81 (e.g., a steel ring), and the driving magnets are adhered to an inner surface of the ring. For some applications a spacer 85 is adhered to the inner surface of ring 81, between the two driving magnets, as shown. A driven magnet 82 is disposed between the driving magnets such that there is axial overlap between the driving magnets and the driven magnet. The driven magnet is coupled to a pin 131, which extends to beyond the distal end of driven magnet 82, where the pin is coupled to the proximal end of drive cable 130. For example, the driven magnet may be cylindrical and define a hole therethrough, and pin 131 may be adhered to an inner surface of the driven magnet that defines the hole. For some applications, the driven magnet is cylindrical, and the magnet includes a North pole and a South pole, which are divided from each other along the length of the cylinder along a line 83 that bisects the cylinder, as shown. For some applications, the driven magnet is housed inside a cylindrical housing 87. Typically, pin 131 defines a guidewire lumen 133.

It is noted that in the application shown in FIG. 7, the driving magnets are disposed outside the driven magnet. However, the scope of the present application includes reversing the configurations of the driving magnets and the driven magnet, mutatis mutandis. For example, the proximal end of the drive cable may be coupled to two or more driven magnets, which are disposed around a driving magnet, such that there is axial overlap between the driven magnets and the driving magnet.

As described hereinabove, typically purging system 29 (shown in FIG. 1A) is used with ventricular assist device 20. Typically, motor unit 23 includes an inlet port 86 and an outlet port 88, for use with the purging system. For some applications, a purging fluid is continuously or periodically pumped into the ventricular assist device via inlet port 86 and out of the ventricular assist device via outlet port 88.

Typically, magnet 82 and pin 131 are held in axially fixed positions within motor unit 23. The proximal end of the drive cable is typically coupled to pin 131 and is thereby held in an axially fixed position by the pin. Typically, drive cable 130 extends from pin 131 to axial shaft 92 and thereby at least partially fixes the axial position of the axial shaft, and in turn impeller 50. For some applications, the drive cable is somewhat stretchable. For example, the drive cable may be made of coiled wires that are stretchable. The drive cable typically allows the axial shaft (and in turn the impeller) to assume a range of axial positions (by the drive cable becoming more or less stretched), but limits the axial motion of the axial shaft and the impeller to being within a certain range of motion (by virtue of the proximal end of the drive cable being held in an axially fixed position, and the stretchability of the drive cable being limited).

As described hereinabove, for some applications, impeller 50 and axial shaft 92 are configured to move axially back-and-forth within frame 34 in response to forces that act upon the impeller, and without requiring the axial shaft to be actively driven to move in the axial back-and-forth motion. Typically, over the course of the subject's cardiac cycle, the pressure difference between the left ventricle and the aorta varies from being approximately zero during systole to a relatively large pressure difference (e.g., 50-70 mmHg) during diastole. For some applications, due to the increased pressure difference that the impeller is pumping against during diastole (and due to the drive cable being stretchable), the impeller is pushed distally with respect to frame 34 during diastole, relative to the location of the impeller with respect to frame 34 during systole. In turn, since the impeller is connected to the axial shaft, the axial shaft is moved forward. During systole, the impeller (and, in turn, the axial shaft) move back to their systolic positions. In this manner, the axial back-and-forth motion of the impeller and the axial shaft is generated in a passive manner, i.e., without requiring active driving of the axial shaft and the impeller, in order to cause them to undergo this motion.

Figures 8A, 8B:
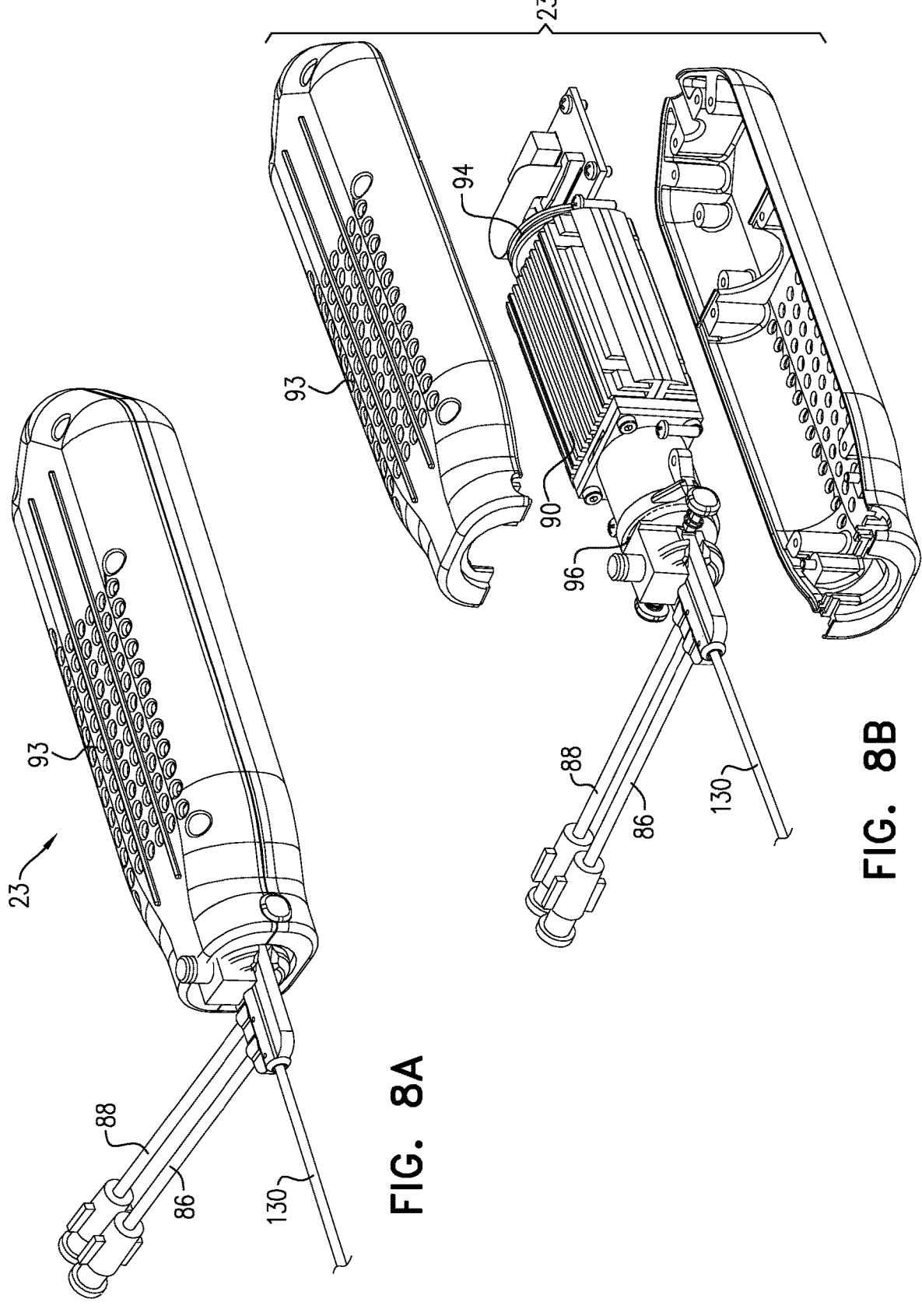
FIGS. 8A and 8B are schematic illustrations of a motor unit of a ventricular assist device, in accordance with some applications of the present invention.

Reference is now made to FIGS. 8A and 8B, which are schematic illustrations of motor unit 23, in accordance with some applications of the present invention. In general, motor unit 23 as shown in FIGS. 8A and 8B is similar to that shown in FIG. 7, and, unless described otherwise, motor unit 23 as shown in FIGS. 8A and 8B contains similar components to motor unit 23 as shown in FIG. 7. For some applications, the motor unit includes a heat sink 90 that is configured to dissipate heat that is generated by the motor. Alternatively or additionally, the motor unit includes ventilation ports 93 that are configured to facilitate the dissipation of heat that is generated by the motor. For some applications, the motor unit includes vibration dampeners 94 and 96 that are configured to dampen vibration of the motor unit that is caused by rotational motion and/or axial back-and-forth motion of components of the ventricular assist device.

Figure 9A:
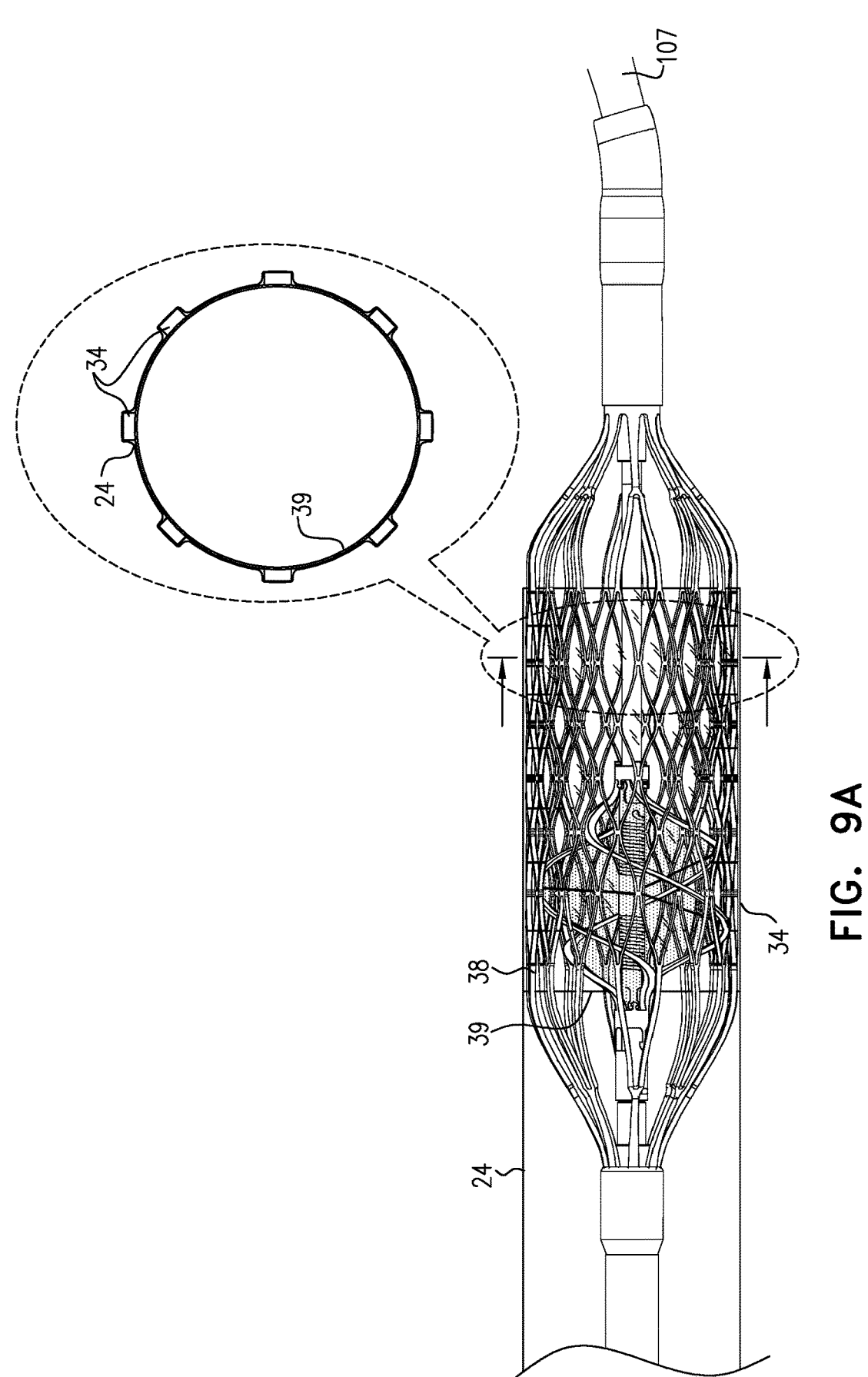
FIGS. 9A and 9B are schematic illustrations of a ventricular assist device that includes an inner lining on the inside of the frame that houses the impeller, in accordance with some applications of the present invention.
Figure 9B:
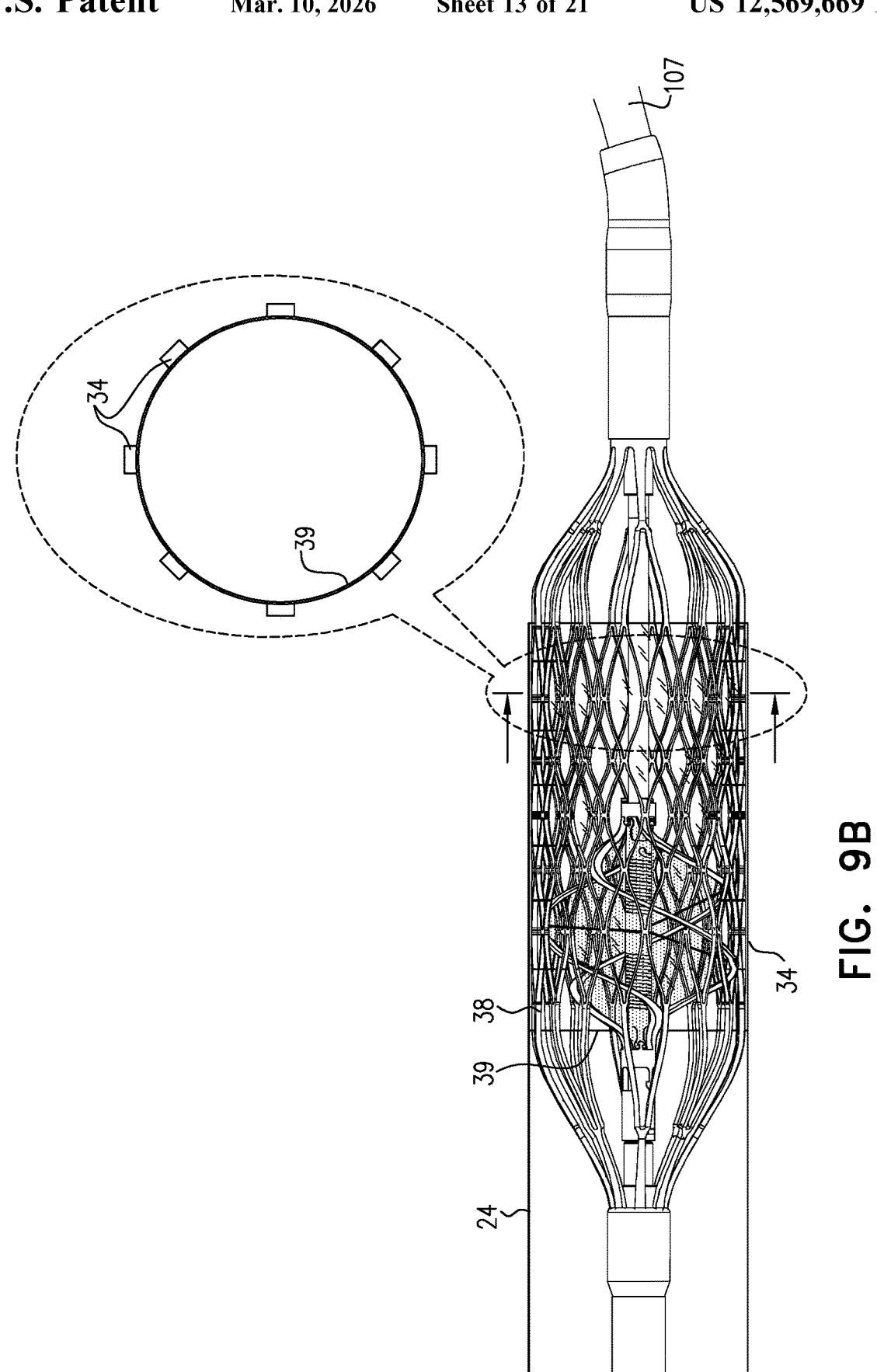

Reference is now made to FIGS. 9A and 9B, which are schematic illustrations of ventricular assist device 20, the device including inner lining 39 that lines the inside of frame 34 that houses impeller 50, in accordance with some applications of the present invention. For some applications, inner lining 39 is disposed inside frame 34, in order to provide a smooth inner surface (e.g., a smooth inner surface having a substantially circular cross-sectional shape) through which blood is pumped by impeller. Typically, by providing a smooth surface, the covering material reduces hemolysis that is caused by the pumping of blood by the impeller, relative to if the blood were pumped between the impeller and struts of frame 34. For some applications, inner lining includes polyurethane, polyester, and/or silicone. Alternatively or additionally, the inner lining includes polyethylene terephthalate (PET) and/or polyether block amide (PEBAX®).

Typically, the inner lining is disposed over the inner surface of at least a portion of central cylindrical portion 38 of frame 34. For some applications, pump-outlet tube 24 also covers central cylindrical portion 38 of frame 34 around the outside of the frame, for example, such that pump-outlet tube 24 and inner lining 39 overlap over at least 50 percent of the length of the inner lining, for example, over the entire length of the cylindrical portion of frame 34, e.g., as shown in FIG. 9A. For some applications, there is only partial overlap between pump-outlet tube 24 and inner lining 39, e.g., as shown in FIG. 9B. For example, pump-outlet tube 24 may overlap with inner lining along less than 50 percent (e.g., along less than 25 percent) of the length of the inner lining. For some such applications, during insertion of ventricular assist device 20 into the subject's body, the impeller is advanced distally within frame 34, such that the impeller is not disposed within the area of overlap between the pump-outlet tube and the inner lining, such that there is no longitudinal location at which the impeller, pump-outlet tube 24, frame 34, and inner lining 39 all overlap with each other. As shown in FIGS. 9A and 9B, for some applications a single axially-facing blood inlet opening 108 is defined at the distal end of the pump-outlet tube and/or the inner lining. Alternatively, the inner lining is disposed over the inner surface of at least a portion of central cylindrical portion 38 of frame 34, and the pump-outlet tube extends to the distal end of the frame and defines a plurality of lateral blood-inlet openings 108. Such applications are described in further detail hereinbelow with reference to FIGS. 11A-13B, for example.

Typically, over the area of overlap between inner lining 39 and pump-outlet tube 24, the inner lining is shaped to form a smooth surface (e.g., in order to reduce hemolysis, as described hereinabove), and pump-outlet tube 24 is shaped to conform with the struts of frame 34 (e.g., as shown in the cross-section in FIG. 9A). Further typically, the inner lining has a substantially circular cross-section (for example, due to the relatively small cell width within the central cylindrical portion of the frame, as described hereinabove, with reference to FIG. 2). For some applications, over the area of overlap between inner lining 39 and pump-outlet tube 24, the pump-outlet tube and the inner lining are coupled to each other, e.g., via vacuum, via an adhesive, and/or using a thermoforming procedure, for example as described hereinbelow.

For some applications, inner lining 39 and pump-outlet tube 24 are made of different materials from each other. For example, the inner lining may be made of polyurethane, and the pump-outlet tube may be made of polyether block amide (PEBAX®). Typically, for such applications, the material from which the inner lining is made has a higher thermoforming temperature than that of the material from which the pump-outlet tube is made. Alternatively, inner lining 39 and pump-outlet tube 24 are made of the same material as each other. For example, the both the inner lining and the pump-outlet tube may be made of may be made of polyurethane or polyether block amide (PEBAX®).

For some applications, the pump-outlet tube and the inner lining are bonded to each other and/or the frame in the following manner. For some applications, the inner lining is directly bonded to the inner surface of the frame, before the pump-outlet tube is bonded to the outside of the frame. It is noted that, by bonding the inner lining directly to the inner surface of the frame, (rather than simply bonding the inner lining to the pump-outlet tube and thereby sandwiching the frame between the inner lining to the pump-outlet tube), any air bubbles, folds, and other discontinuities in the smoothness of the surface provided by the inner lining are typically avoided. For some applications, similar techniques to those described hereinabove, for enhancing bonding between the elastomeric film and the helical elongate elements of the impeller, are used to enhance bonding between the inner lining and the inner surface of the frame. For some applications, initially, the frame is treated so as to enhance bonding between the inner lining and the inner surface of the frame. For some applications, the treatment of the frame includes applying a plasma treatment to the frame (e.g., to the inner surface of the frame), dipping the frame in a coupling agent that has at least two functional groups that are configured to bond respectively with the frame and with the material form which the inner lining is made (e.g., silane solution), and/or dipping the frame in a solution that contains the material from which the inner lining is made (e.g., polyurethane solution). For some applications, the inner lining is made of an elastomeric material (e.g., polyurethane) and the coupling agent is a silane solution, such as a solution of n-(2-aminoethyl)-3-aminopropyltrimethoxysilane, with the silane containing a first functional group (e.g., (OH)) which is configured to bond with the frame (which is typically made of an alloy, such a nitinol), and the silane containing a second functional group (e.g., (NH2)) which is configured to bond with the elastomeric material.

For some applications, subsequently, a solution that contains the material from which the inner lining is made (e.g., polyurethane solution) is sprayed over the central cylindrical portion of the cage. Once the inner surface of the frame has been treated, the inner lining is bonded to the inner surface of the central cylindrical portion of the frame (e.g., to the inner surface of a central cylindrical portion of the frame). Typically, the inner lining (which is shaped as a tube), is placed over a mandrel, the frame is placed over the inner lining, and pressure is applied by a heat shrinking process. Further typically, the assembly of the inner lining and the frame is heated in an oven.

Subsequent to the inner lining having been bonded to the frame, a portion of pump-outlet tube 24 is placed around the outside of the frame. As described above, for some applications, inner lining 39 and pump-outlet tube 24 are made of different materials from each other. For example, the inner lining may be made of polyurethane, and the pump-outlet tube may be made of polyether block amide (PEBAX®). Typically, for such applications, the material from which the inner lining is made has a higher thermoforming temperature than that of the material from which the pump-outlet tube is made. For some applications, in order to mold pump-outlet tube 24 to conform with the struts of frame 34, without causing the inner lining to deform, the frame is heated to a temperature that is above the thermoforming temperature of pump-outlet tube 24 but below the thermoforming temperature of inner lining 39.

Typically, the frame is heated from inside the frame, using the mandrel. Typically, while the frame is heated to the aforementioned temperature, an outer tube (which is typically made from silicone) applies pressure to pump-outlet tube 24 that causes pump-outlet tube 24 to be pushed radially inwardly, in order to cause the pump-outlet tube to conform with the shapes of the struts of the frame, as shown in the cross-section of FIG. 9A. For some applications, during this stage, the mandrel that is placed inside the inner lining and which heats the inner lining is shorter than the length of the inner lining. The mandrel is typically placed within the inner lining such that margins are left outside of the mandrel at each of the ends of the inner lining. Typically, the inner lining acts as a shield to protect the pump-outlet tube from being overheated and becoming damaged by the heating of the mandrel. Placing the inner lining on the mandrel in the aforementioned manner prevents the mandrel from coming into direct contact with the frame and/or the pump-outlet tube. For some applications, the combination of the frame, the inner lining, and the portion of pump-outlet tube 24 disposed around the frame is subsequently shape set to a desired shape and dimensions using shape setting techniques that are known in the art.

Figures 10A, 10B:
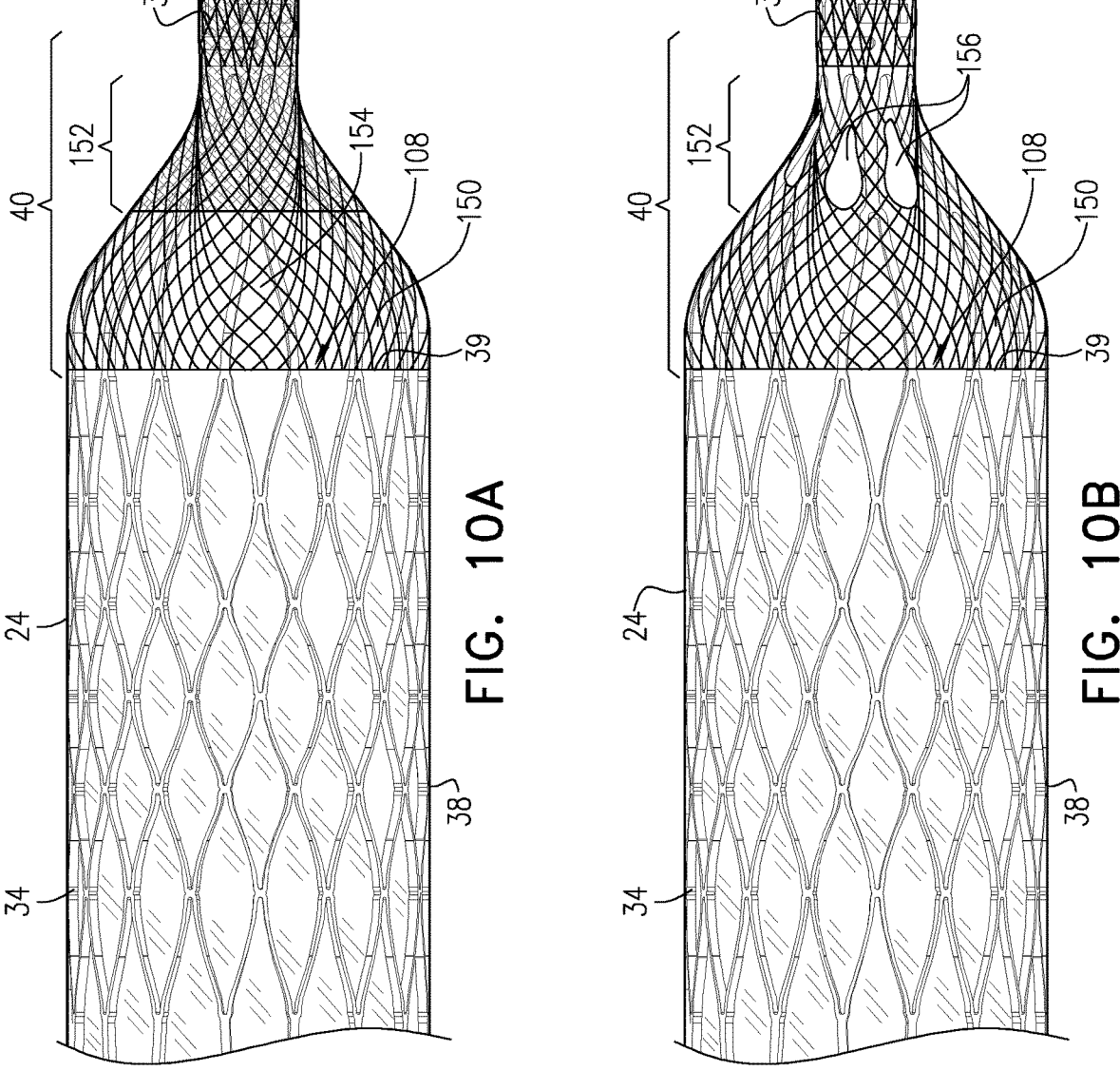
FIGS. 10A, 10B, and 10C are schematic illustrations of a frame of a ventricular assist device that includes a protective braid at a distal end thereof, in accordance with some applications of the present invention.
Figure 10C:
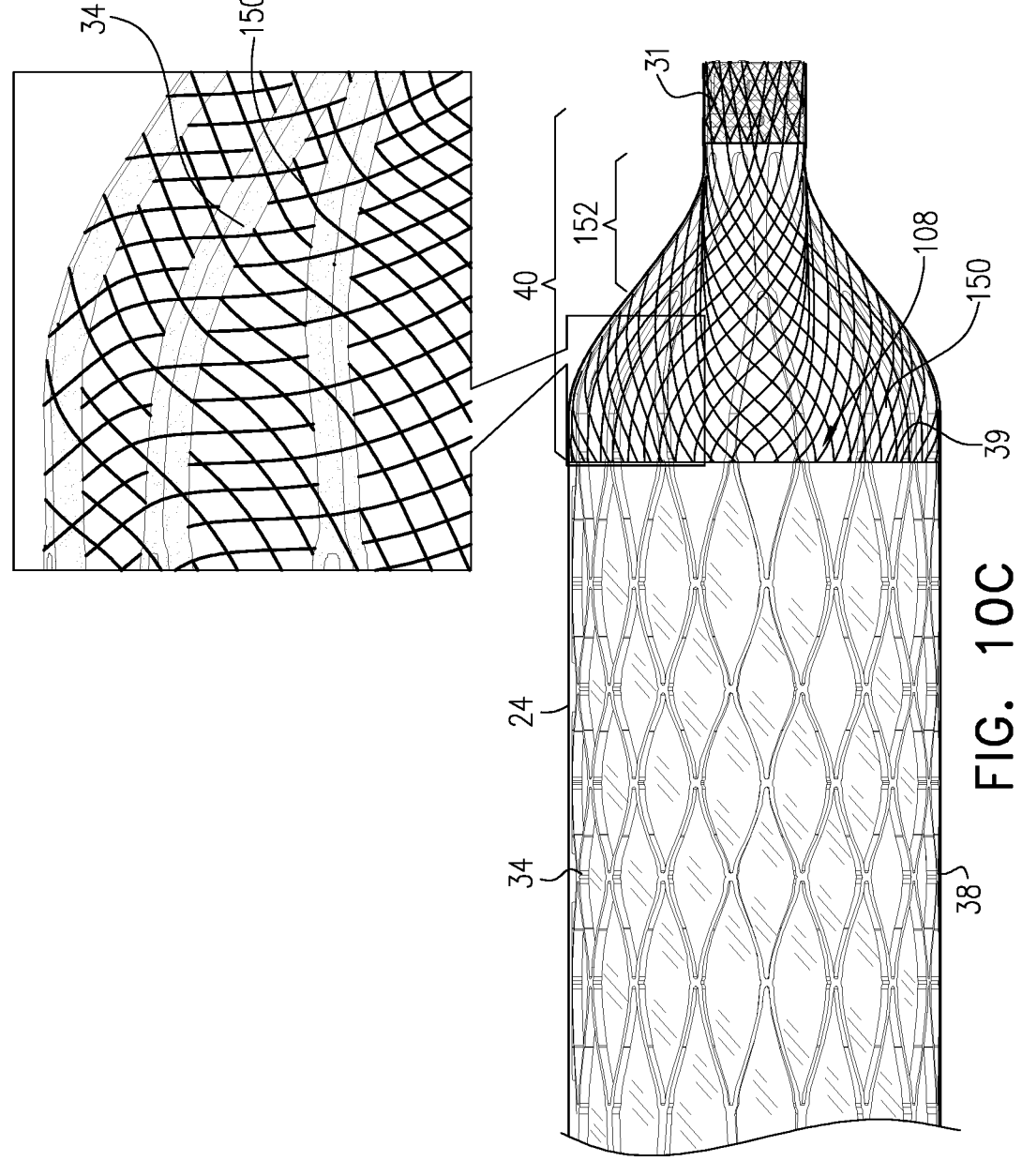

Reference is now made to FIGS. 10A, 10B and 10C, which are schematic illustrations of a portion of a ventricular assist device 20, the ventricular assist device including a protective braid 150 at a distal end thereof, in accordance with some applications of the present invention. For some applications, pump-outlet tube 24 and inner lining 39 extend until the end of the cylindrical portion 38 of frame 34, as shown in FIGS. 10A-C. For some applications, in order to reduce a risk of structures from the left ventricle (such as chordae tendineae, trabeculae carneae, and/or papillary muscles) entering into frame 34 and potentially being damaged by the impeller and/or the axial shaft, and/or causing damage to the left ventricular assist device, distal conical portion 40 of the frame is covered (internally or externally) with protective braid 150. Typically, within at least a portion of the cylindrical portion of the frame, the braid is embedded between the pump-outlet tube and the inner lining, such that, during crimping of the frame, the braid becomes crimped with the pump-outlet tube and the inner lining, thereby preventing the braid from moving with respect to pump-outlet tube and/or the inner lining. (The region in which the protective braid is embedded between the pump-outlet tube and the inner lining is not visible in FIGS. 10A-C, as it is covered by the pump-outlet tube.)

For some applications, protective braid 150 extends substantially until the distal end of the distal conical portion of the frame, as shown in FIG. 10A. For some such applications, along a distal part 152 of the distal conical portion of the frame, the braid is covered with a blood-impermeable material 154 (e.g., polyurethane, polyester, silicone, polyethylene terephthalate (PET) and/or polyether block amide (e.g., PEBAX®)), as shown in FIG. 10A. Typically, most of the blood flow into blood-inlet opening 108 defined by the pump-outlet tube is from the sides of the distal conical portion of the frame, and there is relatively little axial flow via the distal end of the distal conical portion of the frame. Therefore, in some cases, there is a risk of stagnation in this region. In addition, the holes defined by the braid are typically smaller within distal part 152 of the distal conical portion of the frame, due to the narrowing of the frame. Both of these factors can lead to thrombi forming on the braid within the distal part 152 of the distal conical portion of the frame. Therefore, for some applications, the braid is covered along distal part 152 of the distal conical portion of the frame, in order to prevent thrombi from forming on the braid within this part. Typically, the braid is covered (for example, with a blood-impermeable elastomeric material, such as polyurethane). Alternatively, the pattern of the braid does not extend to the distal end of the distal conical portion of the frame. Rather, within distal part 152 of the distal conical portion of the frame the braid is opened or cut, such as to define large apertures 156, as shown in FIG. 10B.

For some applications (not shown), within distal part 152 of the distal conical portion of the frame, the braid is covered (for example, with a blood-impermeable elastomeric material, such as polyurethane), and larger apertures are then cut from the covered braid. Alternatively or additionally (also not shown), within distal part 152 of the distal conical portion of the frame, the braid is covered with a blood-impermeable elastomeric material, e.g., polyurethane, and an aperture is then cut from the covered braid around the full circumference of the frame, such that that the covered braid defines an aperture that extends around the full circumference of distal part 152 of the distal conical portion of the frame. For some such applications, the above-described aperture is cut such that it extends until the distal end of the distal conical portion of the frame, i.e., such that there is a single aperture that extends around the full circumference of the frame and until the distal end of the distal conical portion of the frame.

For some applications, the braid extends substantially until the distal end of the distal conical portion of the frame, and the braid is not covered even within distal part 152 of the distal conical portion of the frame, as shown in FIG. 10C. For some applications, the braid is woven into struts of the distal conical portion of frame 34, as shown in the enlarged frame in FIG. 10C.

Reference is now made to FIGS. 11A-D, which are schematic illustrations of pump-outlet tube 24 or a portion thereof, the pump-outlet tube being configured to define lateral blood-inlet openings 108 at a distal end thereof, in accordance with some applications of the present invention. For some applications, the pump-outlet tube extends substantially until the distal end of distal conical portion 40 of frame 34. For such applications, the pump-outlet tube typically defines a distal conical portion 46 which is distally facing, i.e., facing such that the narrow end of the cone is distal with respect to the wide end of the cone. Typically, the pump-outlet tube includes coupling portion 41 (e.g., a tubular coupling portion, as shown), which extends distally from the pump-outlet tube. As described hereinabove, the coupling portion is coupled to the distal bearing housing in order to anchor the distal end of the pump-outlet tube.

For some applications (not shown), the pump-outlet tube defines two to four lateral blood-inlet openings. Typically, for such applications, each of the blood-inlet openings defines an area of more than 20 square mm (e.g., more than 30 square mm), and/or less than 60 square mm (e.g., less than 50 square mm), e.g., 20-60 square mm, or 30-50 square mm. Alternatively or additionally, the outlet tube defines a greater number of smaller blood-inlet openings 108, e.g., more than 10 blood-inlet openings, more than 50 blood-inlet openings, more than 100 blood-inlet openings, or more than 150 blood-inlet openings, e.g., 50-100 blood-inlet openings, 100-150 blood-inlet openings, or 150-200 blood-inlet openings. For some applications, the blood-inlet openings are sized such as (a) to allow blood to flow from the subject's left ventricle into the tube and (b) to block structures from the subject's left ventricle from entering into the frame. Typically, for such applications, the distal conical portion 46 of pump-outlet tube 24 is configured to reduce a risk of structures from the left ventricle (such as chordae tendineae, trabeculae carneae, and/or papillary muscles) entering into frame 34 and potentially being damaged by the impeller and/or the axial shaft, and/or causing damage to the left ventricular assist device. Therefore, for some applications, the blood-inlet openings are shaped such that, in at least one direction, the widths (or spans) of the openings are less than 1 mm, e.g., 0.1-1 mm, or 0.3-0.8 mm. By defining such a small width (or span), it is typically the case that structures from the left ventricle (such as chordae tendineae, trabeculae carneae, and/or papillary muscles) are blocked from entering into frame 34. For some such applications, each of the blood-inlet openings defines an area of more than 0.05 square mm (e.g., more than 0.1 square mm), and/or less than 3 square mm (e.g., less than 1 square mm), e.g., 0.05-3 square mm, or 0.1-1 square mm. Alternatively, each of the blood-inlet openings defines an area of more than 0.1 square mm (e.g., more than 0.3 square mm), and/or less than 5 square mm (e.g., less than 1 square mm), e.g., 0.1-5 square mm, or 0.3-1 square mm.

Typically, the portion of the pump-outlet tube that defines the blood-inlet openings has a porosity of more than 40 percent, e.g., more than 50 percent, or more than 60 percent (where porosity is defined as the percentage of the area of this portion that is porous to blood flow). Thus, on the one hand, the blood-inlet openings are relatively small (in order to prevent structures of the left ventricular from entering the frame), but on the other hand, the porosity of the portion of the pump-outlet tube that defines the blood-inlet openings is relatively high, such as to allow sufficient blood flow into the pump-outlet tube.

Figures 11A, 11B:
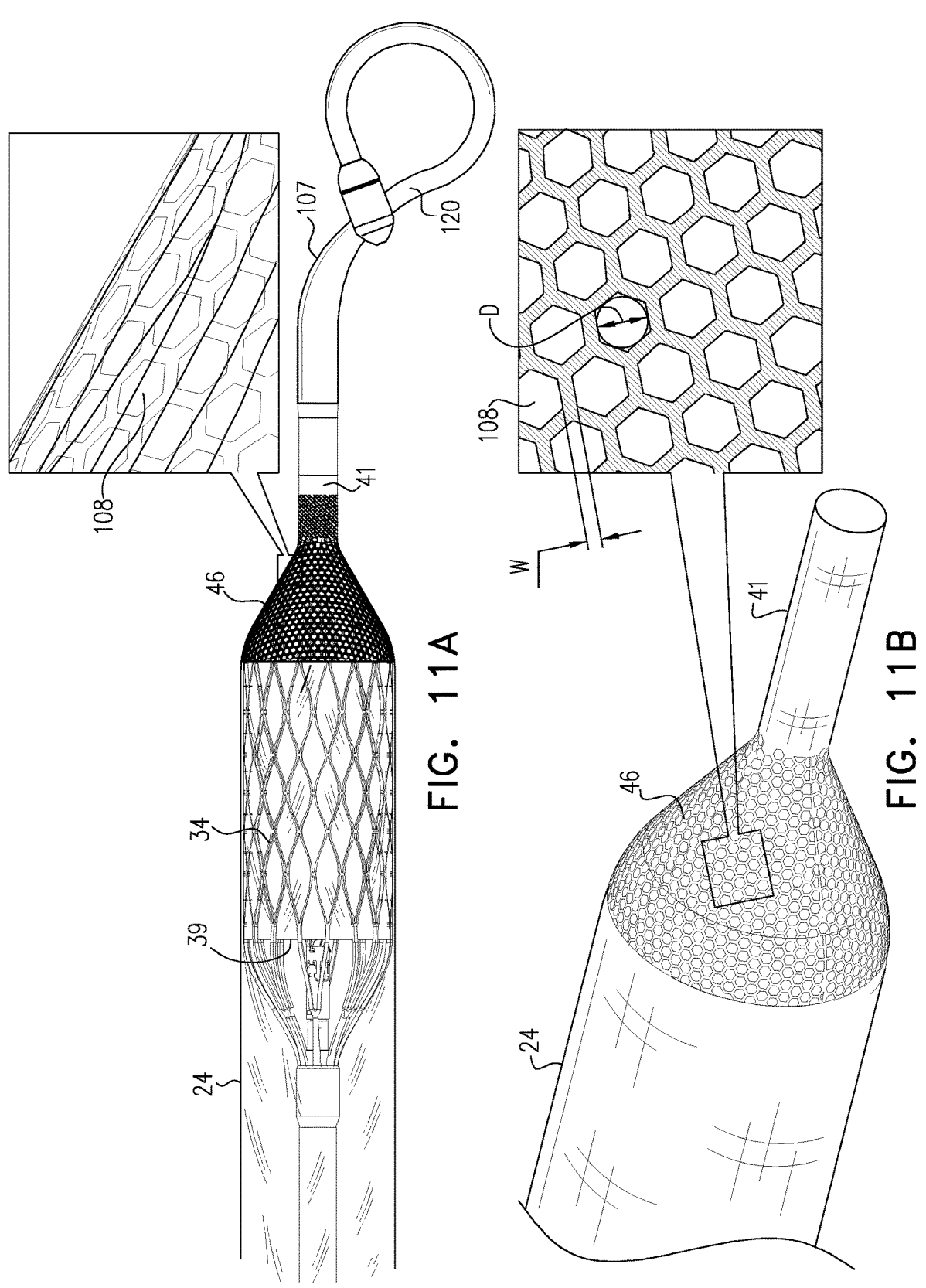
FIGS. 11A, 11B, 11C, and 11D are schematic illustrations of a pump-outlet tube that defines blood-inlet openings at a distal end thereof, in accordance with some applications of the present invention.

For some applications, each the blood-inlet openings has a circular or a polygonal shape. For some applications, each of the blood-inlet openings has a hexagonal shape, as shown in FIGS. 11A-D. Typically, using openings having a hexagonal shape allows the portion of the pump-outlet tube that defines the blood-inlet openings to have a relatively high porosity (e.g., as described hereinabove), while providing the portion of the pump-outlet tube that defines the blood-inlet openings with sufficient material between the blood-inlet openings to prevent tearing and/or stretching of the material. As shown in FIG. 11B, for some applications, a width W of gaps between adjacent hexagonal (or other polygonal) holes is more than 0.01 mm (e.g., more than 0.04 mm), and/or less than 0.1 mm (e.g., less than 0.08 mm), for example, 0.01-0.1 mm, or 0.04-0.08 mm. For some applications, the distance D between opposing sides of each of the hexagons (or other types of polygons) is more than 0.2 mm (e.g., more than 0.4 mm) and/or less than 0.8 mm (e.g., less than 0.6 mm), e.g., 0.2-0.8 mm, or 0.4-0.6 mm. As indicated in FIG. 11B, typically each of the polygons encloses a circle (such that any structure that cannot pass through such a circle would be unable to pass through the polygon). Typically, the diameter of the circle enclosed by the polygon is the equivalent of distance D, e.g., more than 0.2 mm (e.g., more than 0.4 mm) and/or less than 0.8 mm (e.g., less than 0.6 mm), e.g., 0.2-0.8 mm, or 0.4-0.6 mm.

Figures 11C, 11D:
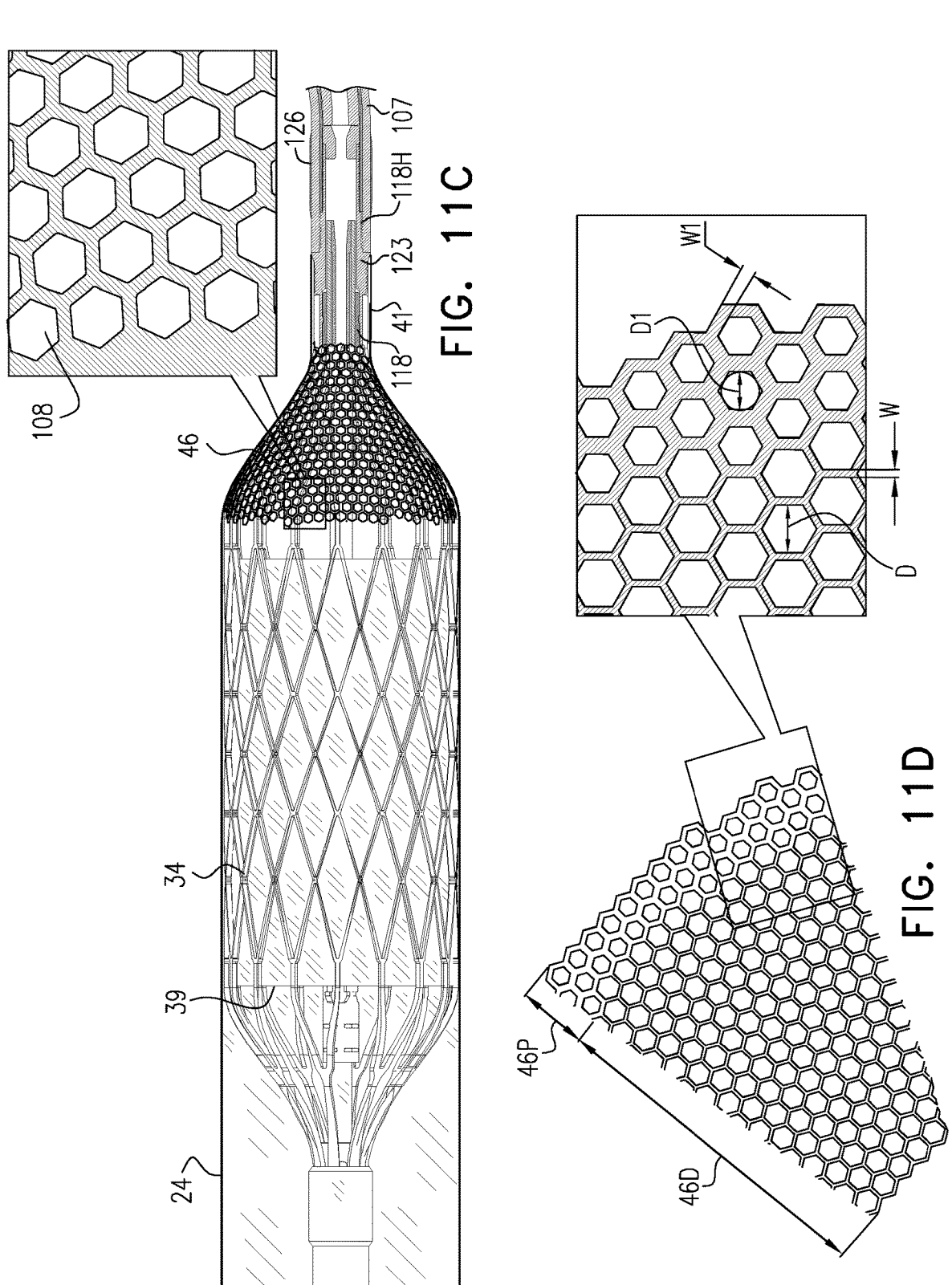

FIG. 11D shows a segment of distal conical portion 46 of pump-outlet tube 24, in accordance with some applications of the present invention. In the view shown in FIG. 11D, the segment is laid our flat for illustrative purposes. As shown in FIG. 11D, for some applications, within a proximal region 46P of distal conical portion 46 of pump-outlet tube 24, the widths W1 of the gaps between the hexagonal (or other type of polygonal) holes are larger than widths W of the gaps between the hexagonal (or other type of polygonal) holes within a distal region 46D of distal conical portion 46 of the pump-outlet tube. For some applications, the ratio of the widths of gaps between adjacent blood-inlet openings with the proximal region of the distal portion of the pump-outlet tube to the widths of gaps between adjacent blood-inlet openings within the distal region of the distal portion of the pump-outlet tube is greater than 3:2, e.g., between 3:2 and 5:2. Typically, for such applications, within proximal region 46P of distal conical portion 46 of pump-outlet tube 24, a distance D1 between opposing sides of each of the hexagons (or other type of polygons) is smaller than distance D between opposing sides of each of the hexagons (or other type of polygons) within distal region 46D of distal conical portion 46 of the pump-outlet tube. (As described hereinabove, typically, distances D and D1 also represent the diameter of a circle that is enclosed by the respectively sized polygons.) For some applications, the ratio of the diameter of a circle enclosed by each of the blood-inlet openings with the distal region of the distal portion of the pump-outlet tube to a diameter of a circle enclosed by each of the blood-inlet openings with the proximal region of the distal portion of the pump-outlet tube is greater than 7:6, e.g., between 7:6 and 4:3. Further typically, within distal region 46D, the distal conical portion of pump-outlet tube 24, has a higher porosity than within proximal region 46P of the distal conical portion 46 of the pump-outlet tube. For example, the ratio of porosity within distal region 46D to the porosity within proximal region 46P is more than 4:3, or more than 3:2. For some applications, the proximal region extends along a length of more than 0.5 mm, and/or less than 2 mm (e.g., less than 1.5 mm), for example, between 0.5-2 mm or 0.5-1.5 mm. For some applications, the total length of the distal conical portion is more than 6 mm and/or or less than 12 mm (e.g., less than 10 mm), for example between 6-12 mm, or 6-10 mm.

As described hereinabove with reference to FIGS. 9A-B, typically, the pump-outlet tube is coupled to frame 34 via heating. For some applications, within the proximal region 46P of distal conical portion 46 of pump-outlet tube 24, the gaps between the blood-inlet holes are wider and/or the blood-inlet holes are smaller than within distal region 46D, and/or the porosity is lower than within distal region 46D, in order to prevent and/or reduce damage (e.g., tearing, thinning, and/or stretching) that may be caused to the material that defines the blood-inlet holes from being damaged during the above-described heating process.

Typically, width W of the gaps between the hexagonal (or other type of polygonal) holes and distance D between opposing sides of each of the hexagons (or other type of polygons) within distal region 46D of distal conical portion 46 of the pump-outlet tube are as described hereinabove. For some applications, width W1 of gaps between adjacent hexagonal (or other polygonal) holes within proximal region 46P of distal conical portion 46 of pump-outlet tube 24 is more than 0.05 mm (e.g., more than 0.07 mm), and/or less than 0.2 mm (e.g., less than 0.15 mm), for example, 0.05-0.2 mm, or 0.07-0.15 mm. For some applications, distance D1 between opposing sides of each of the hexagons (or other types of polygons) within proximal region 46P of distal conical portion 46 of pump-outlet tube 24 is more than 0.1 mm (e.g., more than 0.3 mm) and/or less than 0.6 mm (e.g., less than 0.5 mm), e.g., 0.1-0.6 mm, or 0.3-0.5 mm.

The scope of the present disclosure includes having non-uniformly sized and/or shaped lateral blood-inlet openings (e.g., circular, rectangular, polygonal, and/or hexagonal lateral blood-inlet openings), disposed in any arrangement along the distal conical portion 46 of the pump-outlet tube. Similarly, the scope of the present disclosure includes a distal conical portion 46 of the pump-outlet tube that defines lateral blood-inlet openings being arranged such that the distal conical portion has a non-uniform porosity, with the porosity varying over different regions of the distal conical portion. For some applications, the shapes and/or sizes of the lateral blood-inlet openings, and/or the porosity of the distal conical portion, is varied such as to account for varying blood flow dynamics at different regions of the distal conical portion. Alternatively or additionally, the shapes and/or sizes of the lateral blood-inlet openings, and/or the porosity of the distal conical portion, is varied such as to account for changes in the shape of the distal conical portion along its length.

Figures 12A, 12B:
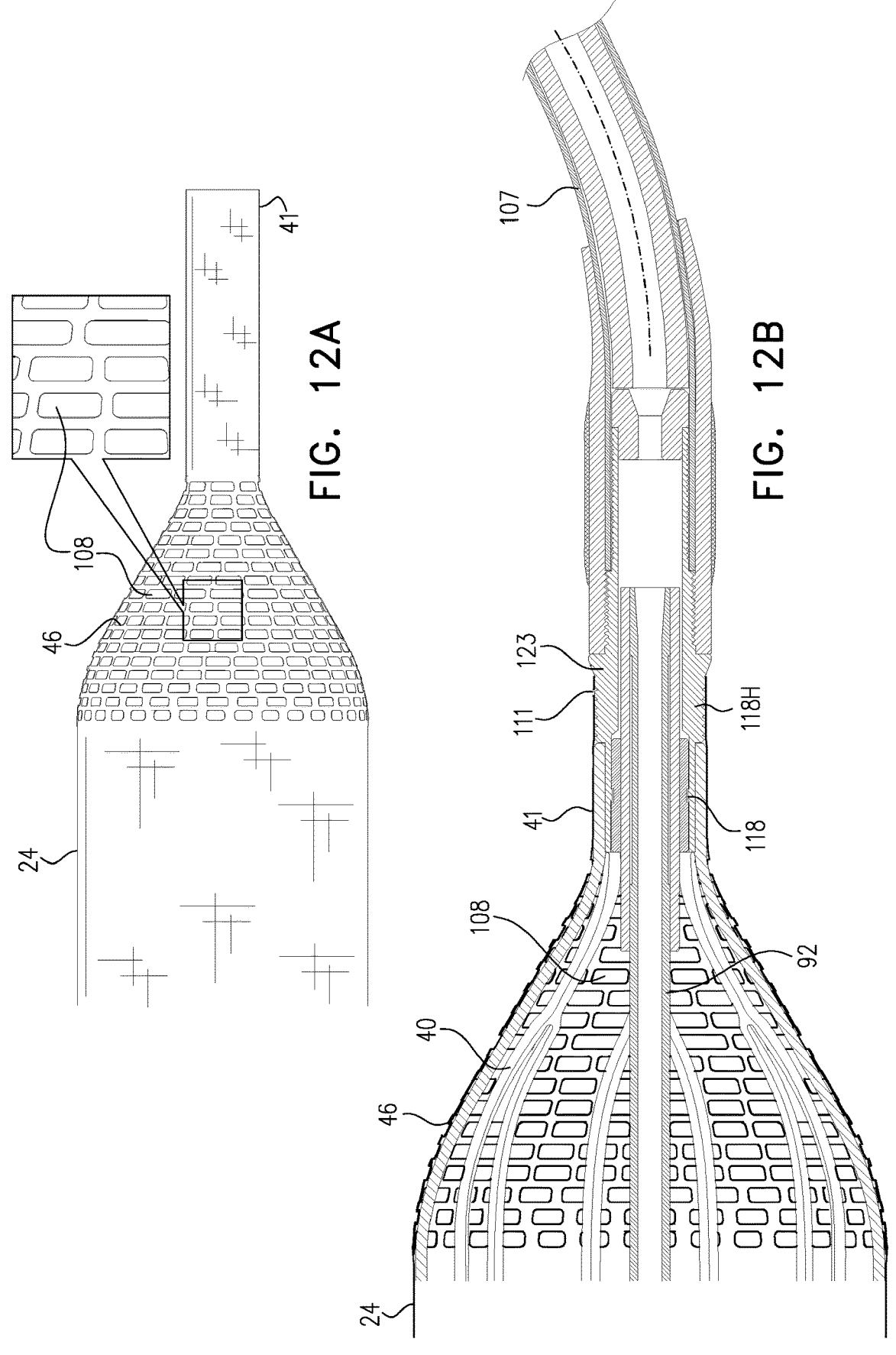
FIGS. 12A and 12B are schematic illustrations of a pump-outlet tube that defines blood-inlet openings at a distal end thereof, in accordance with some applications of the present invention.

Reference is now made to FIGS. 12A-B, which are schematic illustrations of pump-outlet tube 24 or a portion thereof, the pump-outlet tube being configured to define lateral blood-inlet openings 108 at a distal end thereof, in accordance with some applications of the present invention. As described with reference to FIGS. 11A-D, for some applications, the pump-outlet tube extends substantially until the distal end of distal conical portion 40 of frame 34. For such applications, the pump-outlet tube typically defines a distal conical portion 46 which is distally facing, i.e., facing such that the narrow end of the cone is distal with respect to the wide end of the cone. For some applications, the pump-outlet tube defines more than 10 blood-inlet openings, more than 50 blood-inlet openings, more than 100 blood-inlet openings, or more than 150 blood-inlet openings, e.g., 50-100 blood-inlet openings, 100-150 blood-inlet openings, or 150-200 blood-inlet openings. For some applications, the blood-inlet openings are sized such as (a) to allow blood to flow from the subject's left ventricle into the tube and (b) to block structures from the subject's left ventricle from entering into the frame. Typically, for such applications, the distal conical portion 46 of pump-outlet tube 24 is configured to reduce a risk of structures from the left ventricle (such as chordae tendineae, trabeculae carneae, and/or papillary muscles) entering into frame 34 and potentially being damaged by the impeller and/or the axial shaft, and/or causing damage to the left ventricular assist device. Therefore, for some applications, the blood-inlet openings are shaped such that, in at least one direction, the widths (or spans) of each of the openings are less than 1 mm, e.g., 0.1-1 mm, or 0.3-0.8 mm. By defining such a small width (or span), it is typically the case that structures from the left ventricle (such as chordae tendineae, trabeculae carneae, and/or papillary muscles) are blocked from entering into frame 34. For some such applications, each of the blood-inlet openings defines an area of more than 0.05 square mm (e.g., more than 0.1 square mm), and/or less than 3 square mm (e.g., less than 1 square mm), e.g., 0.05-3 square mm, or 0.1-1 square mm. Alternatively, each of the blood-inlet openings defines an area of more than 0.1 square mm (e.g., more than 0.3 square mm), and/or less than 5 square mm (e.g., less than 1 square mm), e.g., 0.1-5 square mm, or 0.3-1 square mm.

For some applications, the blood-inlet openings define generally rectangular shapes, as shown in FIGS. 12A-B. For some such applications, the ratio of the lengths to the widths of the blood-inlet openings is between 1.1:1 and 4:1, e.g., between 3:2 and 5:2. For some applications, by having such shapes, the blood-inlet openings are configured (a) to block structures from the left ventricle (such as chordae tendineae, trabeculae carneae, and/or papillary muscles) from entering into frame 34, but (b) to provide the portion of the pump-outlet tube that defines the blood-inlet openings with a relatively high porosity. Typically, the portion of the pump-outlet tube that defines the blood-inlet openings has a porosity of more than 40 percent, e.g., more than 50 percent, or more than 60 percent (where porosity is defined as the percentage of the area of this portion that is porous to blood flow). Thus, on the one hand the blood-inlet openings are relatively small (in order to prevent structures of the left ventricular from entering the frame), but on the other hand, the porosity of the portion of the pump-outlet tube that defines the blood-inlet openings is relatively high, such as to allow sufficient blood flow into the pump-outlet tube.

Typically, the pump-outlet tube includes a coupling portion 41 (e.g., a tubular coupling portion, as shown), which extends distally from the pump-outlet tube. As described hereinabove, the coupling portion is coupled to distal bearing housing 118H in order to anchor the distal end of the pump-outlet tube. Also as described hereinabove, typically, the pump-outlet tube is coupled to the outside of the central cylindrical portion of the frame. For some applications, distal conical portion 46 of the pump-outlet tube is not itself bonded to distal conical portion 40 of the frame. Rather, distal conical portion 46 of the pump-outlet tube is held in place with respect to distal conical portion 40 of the frame, by virtue of coupling portion 41 being coupled to distal bearing housing 118H and the pump-outlet tube being coupled to the outside of the central cylindrical portion of the frame. Alternatively, the distal conical portion 46 of the pump-outlet tube is directly coupled to distal conical portion 40 of the frame (e.g., via heat shrinking).

As described hereinabove, for some applications, coupling portion 41 is coupled to the outer surface of portion 123 of distal bearing housing 118H. For some applications, coupling portion 41 defines a hole 111 (e.g., toward the distal end of the coupling portion), as shown in FIG. 12B. For some applications, adhesive is applied between coupling portion 41 and the outer surface of portion 123 of distal bearing housing 118H, via the hole. As described hereinabove, for some application, the outer surface of portion 123 of distal bearing housing 118H is threaded. Typically, the threaded outer surface allows the adhesive to gradually and uniformly spread between coupling portion 41 and the outer surface of portion 123 of distal bearing housing 118H. Further typically, the coupling portion is transparent, such that the spread of the adhesive is visible through the coupling portion. Therefore, for some applications, once the adhesive has sufficiently spread between coupling portion 41 and the outer surface of portion 123 of distal bearing housing 118H (e.g., once the outer surface of portion 123 has been covered with the adhesive), application of the adhesive is terminated.

It is noted that the above description of methods and apparatus for bonding distal conical portion 46 of the pump-outlet tube with respect to other portions of the ventricular assist device is applicable to any embodiments of the distal conical portions 46 of the pump-outlet tube that are described herein, including any one of the embodiments described with reference to FIGS. 11A-13B. For some applications, similar techniques are used to bond protective braid 150 (shown in FIGS. 10A-C) to the distal bearing housing.

It is noted that, although the above description of methods and apparatus for bonding a coupling portion to a surface have been described with reference to the distal portion of the pump-outlet tube and the outer surface of the distal bearing housing, similar apparatus and methods are applicable to any type of inlet guard (i.e., any element that is disposed over the distal conical portion of the frame and defines blood-inlet openings that are sized such as (a) to allow blood to flow from the subject's left ventricle into the tube and (b) to block structures from the subject's left ventricle from entering into the frame) and any surface that is disposed distally to the frame.

Figures 13A, 13B:
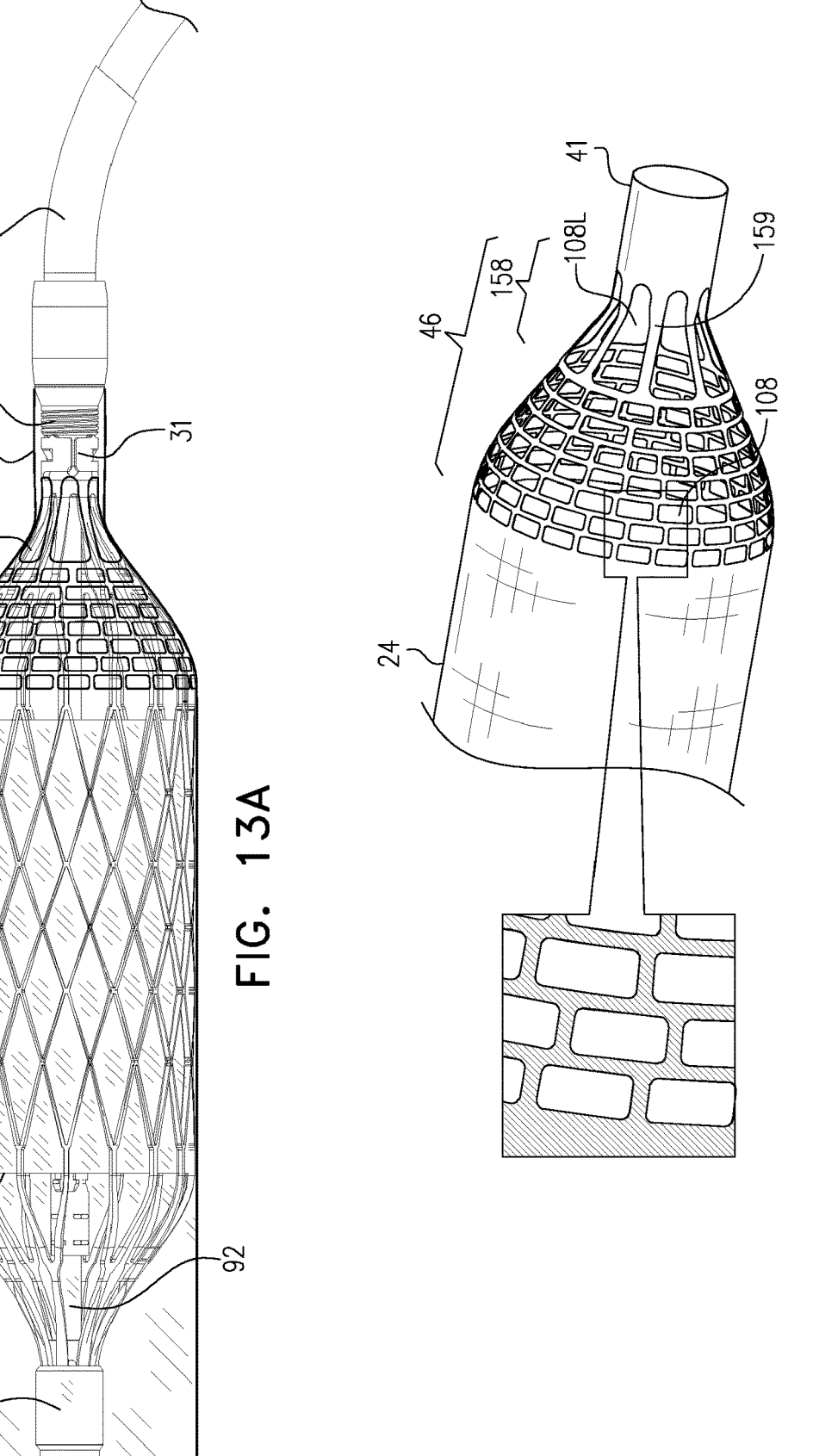
FIGS. 13A and 13B are schematic illustrations of a pump-outlet tube that defines blood-inlet openings at a distal end thereof, in accordance with some applications of the present invention.

Reference is now made to FIGS. 13A-B, which are schematic illustrations of pump-outlet tube 24 or a portion thereof, the pump-outlet tube being configured to define lateral blood-inlet openings 108 at a distal end thereof, in accordance with some applications of the present invention. Pump-outlet tube 24 of FIGS. 13A-B is generally similar to that shown in FIGS. 12A-B except for the differences described below. As described with reference to FIG. 10A, typically, most of the blood flow into blood-inlet openings 108 is from the sides of the distal conical portion of the frame, and there is relatively little axial flow via the distal end of the distal conical portion of the frame. Therefore, in some cases, there is a risk of stagnation in this region, which can lead to thrombi forming within the distal end of the distal conical portion of the frame. Moreover, due to the lower blood flow, there is a lower risk of structures from the left ventricle (such as chordae tendineae, trabeculae carneae, and/or papillary muscles) entering into frame 34 via this region. Therefore, for some applications, along a distal part 158 of distal conical portion 46 of pump-outlet tube 24 (which typically covers the distal part of the distal conical portion of the frame), the pump-outlet tube 24 defines large blood-inlet openings 108L, which reduces the risk of thrombosis relative to if the blood-inlet openings along distal part 158 of distal conical portion 46 of pump-outlet tube 24 were smaller. (In some cases distal part 158 corresponds to distal region 46D, shown in FIG. 11D.) Typically, the large blood-inlet openings 108L have trapezoidal or triangular shapes. For some applications, the shapes of the large blood-inlet openings conforms with the shapes of the struts of the frame within the distal part of the frame. That is to say that the borders 159 of the large blood-inlet openings lie along struts of the distal portion of the frame, and the openings themselves lie over the openings defined by the struts. For some applications, there are between 4 and 12 (e.g., between 6 and 10) large blood-inlet openings. Typically each of the large blood-inlet openings has an area of 1-7 square mm, e.g., 2-5 square mm, or 3-4 square mm. For some applications, a ratio of the area of the smallest of large blood-inlet openings 108L to the largest of the smaller blood-inlet openings 108 is more than 3:1, e.g., more than 4:1. Typically, within distal part 158 of distal conical portion 46 of pump-outlet tube 24, tube 24 has a porosity of more than 55 percent, e.g., more than 65 percent.

Figures 14A, 14B, 15:
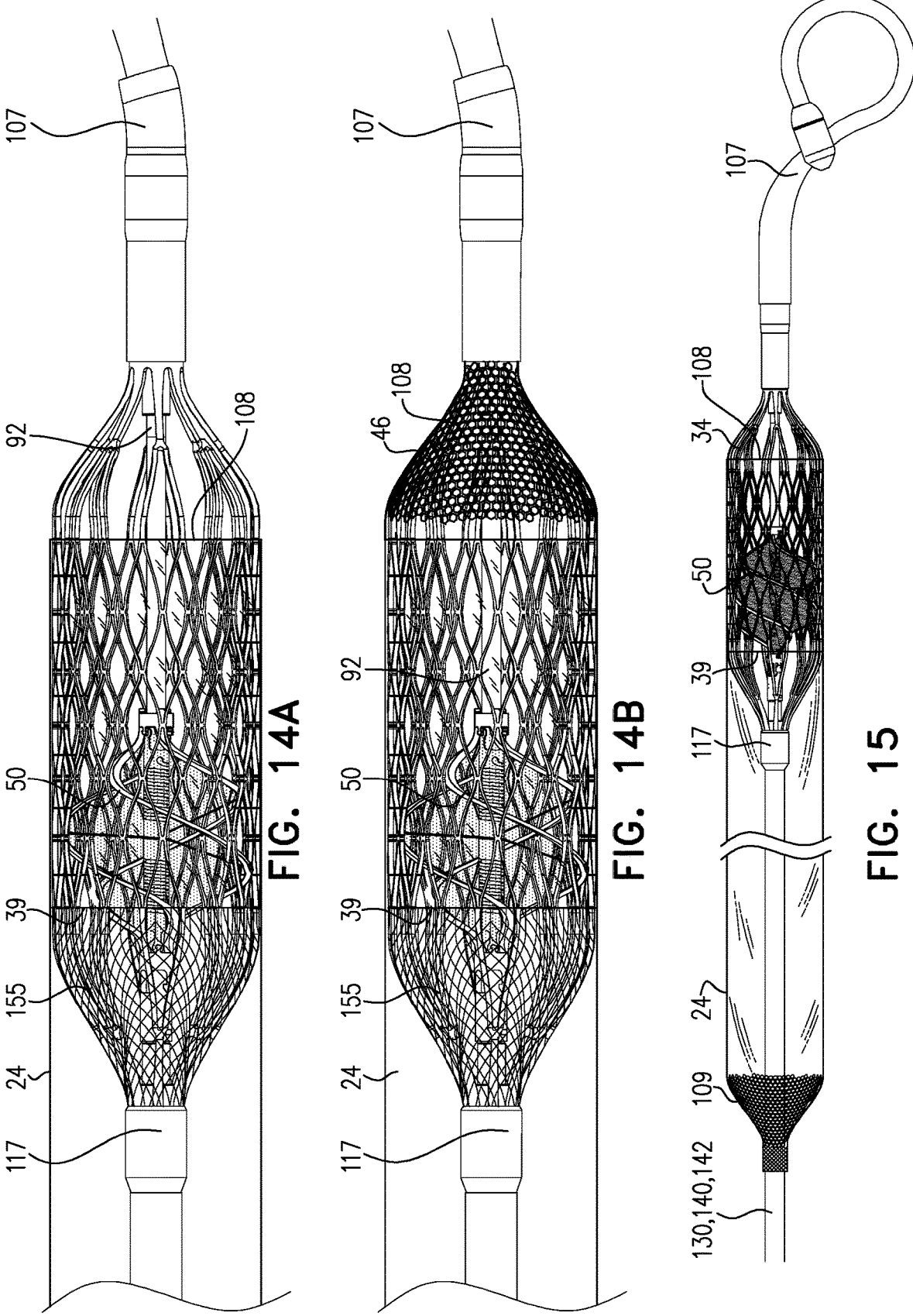
FIGS. 14A and 14B are schematic illustrations of a frame of a ventricular assist device that includes a protective braid at a proximal end thereof, in accordance with some applications of the present invention.
FIG. 15 is a schematic illustration of a pump-outlet tube that defines blood-outlet openings at a proximal end thereof, in accordance with some applications of the present invention.
Figure 16:
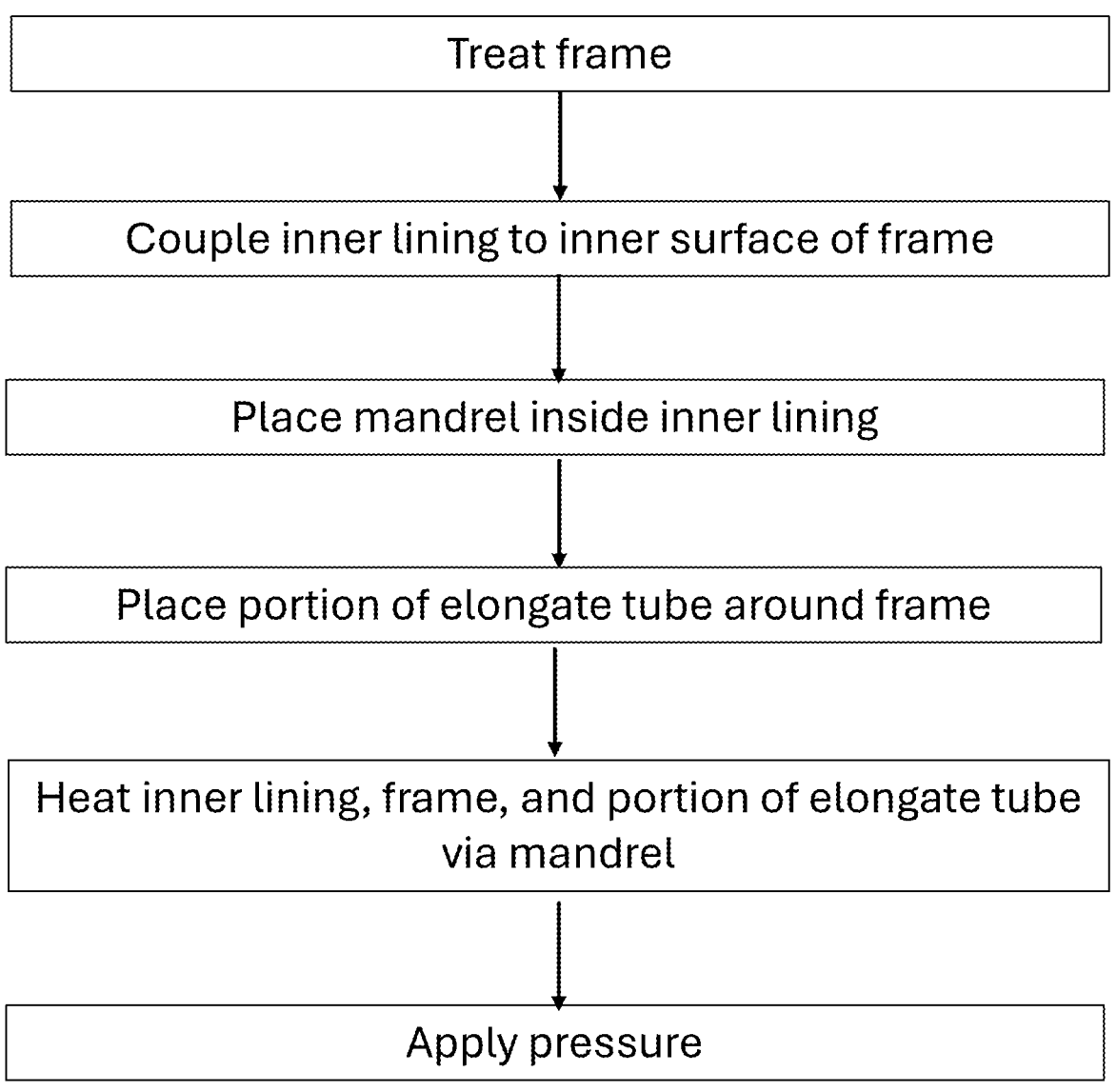
FIG. 16 is a flowchart showing steps of a method performed, in accordance with some applications of the present disclosure.

Reference is now made to FIGS. 14A and 14B, which are schematic illustrations of frame 34 of ventricular assist device 20, the frame including a protective braid 155 at a proximal end thereof, in accordance with some applications of the present invention. For some applications, the protective braid is disposed over (or within) the proximal conical section of frame 34. For example, the protective braid may be woven into struts of the frame in a similar manner to that described with reference to FIG. 10C. Typically, the protective braid is configured to act as a filter, for example by preventing any elements that are greater than a given size (e.g., thrombi) from migrating proximally along pump-outlet tube 24. The protective braid is used in combination with any one of the embodiments described herein. For example, the protective braid may be used with a pump-outlet tube that defines a single axially-facing blood-inlet opening 108 (as shown in FIG. 14A), or it may be used with a pump-outlet tube that defines lateral blood-inlet openings 108 (as shown in FIG. 14B).

Reference is now made to FIG. 15, which is a schematic illustration of pump-outlet tube 24 that defines blood-outlet openings 109 at a proximal end thereof, in accordance with some applications of the present invention. For some applications, the blood-outlet openings are sized and shaped in similar shapes and sizes to any one of the embodiments of lateral blood-inlet openings 108 described herein. For some applications, by having such shapes, the region of the pump-outlet tube that defines the blood-outlet openings is configured (a) act as a filter, for example, by preventing any elements that are greater than a given size (e.g., thrombi) from migrating proximally from the pump-outlet tube 24, and also (b) to provide the portion of the pump-outlet tube that defines the blood-outlet openings with a relatively high porosity. Typically, the portion of the pump-outlet tube that defines the blood-outlet openings has a porosity of more than 40 percent, e.g., more than 50 percent, or more than 60 percent (where porosity is defined as the percentage of the area of this portion that is porous to blood flow). Thus, on the one hand the blood-outlet openings are relatively small (in order to prevent any elements that are greater than a given size (e.g., thrombi) from migrating proximally from the pump-outlet tube 24), but on the other hand, the porosity of the portion of the pump-outlet tube that defines the blood-outlet openings is relatively high, such as to allow sufficient blood flow from the pump-outlet tube. The blood-outlet openings as shown in FIG. 15 may be used in combination with any one of the embodiments described herein. For example, the blood-outlet openings as shown in FIG. 15 may be used as part of a pump-outlet tube that defines a single axially-facing blood-inlet opening 108 (as shown in FIG. 15), or it may be used as part of a pump-outlet tube that defines lateral blood-inlet openings 108 (combination not shown).

With regards to all aspects of ventricular assist device 20 described with reference to FIGS. 1A-15, it is noted that, although FIGS. 1A and 1B show ventricular assist device 20 in the subject's left ventricle, for some applications, ventricular assist device 20 is placed inside the subject's right ventricle, such that the device traverses the subject's pulmonary valve, and techniques described herein are applied, mutatis mutandis. For some applications, components of device 20 are applicable to different types of blood pumps. For example, aspects of the present invention may be applicable to a pump that is used to pump blood from the vena cava and/or the right atrium into the right ventricle, from the vena cava and/or the right atrium into the pulmonary artery, and/or from the renal veins into the vena cava. Such aspects may include features of tube 24 (e.g., the curvature of the tube), impeller 50, features of pump-head portion 27, drive cable 130, etc. Alternatively or additionally, device 20 and/or a portion thereof (e.g., impeller 50, even in the absence of tube 24) is placed inside a different portion of the subject's body, in order to assist with the pumping of blood from that portion. For example, device 20 and/or a portion thereof (e.g., impeller 50, even in the absence of tube 24) may be placed in a blood vessel and may be used to pump blood through the blood vessel. For some applications, device 20 and/or a portion thereof (e.g., impeller 50, even in the absence of tube 24) is configured to be placed within the subclavian vein or jugular vein, at junctions of the vein with a lymph duct, and is used to increase flow of lymphatic fluid from the lymph duct into the vein, mutatis mutandis. Since the scope of the present invention includes using the apparatus and methods described herein in anatomical locations other than the left ventricle and the aorta, the ventricular assist device and/or portions thereof are sometimes referred to herein (in the specification and the claims) as a blood pump.

The scope of the present invention includes combining any of the apparatus and methods described herein with any of the apparatus and methods described in one or more of the following applications, all of which are incorporated herein by reference:

U.S. Ser. No. 17/609,589 to Tuval, entitled "Ventricular assist device," which is the US national phase of PCT Application No. PCT/IB2021/052857 (published as WO 21/205346), filed Apr. 6, 2021, which claims priority from:

U.S. Provisional Patent Application 63/006,122 to Tuval, entitled "Ventricular assist device," filed Apr. 7, 2020;

U.S. Provisional Patent Application 63/114,136 to Tuval, entitled "Ventricular assist device," filed Nov. 16, 2020; and U.S. Provisional Patent Application 63/129,983 to Tuval, entitled "Ventricular assist device," filed Dec. 23, 2020.

US 2020/0237981 to Tuval, entitled "Distal tip element for a ventricular assist device," filed Jan. 23, 2020, which claims priority from:

U.S. Provisional Patent Application 62/796,138 to Tuval, entitled "Ventricular assist device," filed Jan. 24, 2019;

U.S. Provisional Patent Application 62/851,716 to Tuval, entitled "Ventricular assist device," filed May 23, 2019;

U.S. Provisional Patent Application 62/870,821 to Tuval, entitled "Ventricular assist device," filed Jul. 5, 2019; and U.S. Provisional Patent Application 62/896,026 to Tuval, entitled "Ventricular assist device," filed Sep. 5, 2019.

US 2019/0209758 to Tuval, which is a continuation of International Application No. PCT/IB2019/050186 to Tuval (published as WO 19/138350), entitled "Ventricular assist device, filed Jan. 10, 2019, which claims priority from:

U.S. Provisional Patent Application 62/615,538 to Sohn, entitled "Ventricular assist device," filed Jan. 10, 2018;

U.S. Provisional Patent Application 62/665,718 to Sohn, entitled "Ventricular assist device," filed May 2, 2018;

U.S. Provisional Patent Application 62/681,868 to Tuval, entitled "Ventricular assist device," filed Jun. 7, 2018; and U.S. Provisional Patent Application 62/727,605 to Tuval, entitled "Ventricular assist device," filed Sep. 6, 2018;

US 2019/0269840 to Tuval, which is the US national phase of International Patent Application PCT/IL2017/051273 to Tuval (published as WO 18/096531), filed Nov. 21, 2017, entitled "Blood pumps," which claims priority from U.S. Provisional Patent Application 62/425,814 to Tuval, filed Nov. 23, 2016;

US 2019/0175806 to Tuval, which is a continuation of International Application No. PCT/IL2017/051158 to Tuval (published as WO 18/078615), entitled "Ventricular assist device," filed Oct. 23, 2017, which claims priority from U.S. 62/412,631 to Tuval filed Oct. 25, 2016, and U.S. 62/543, 540 to Tuval, filed Aug. 10, 2017;

US 2019/0239998 to Tuval, which is the US national phase of International Patent Application PCT/IL2017/051092 to Tuval (published as WO 18/061002), filed Sep. 28, 2017, entitled "Blood vessel tube," which claims priority from U.S. Provisional Patent Application 62/401,403 to Tuval, filed Sep. 29, 2016;

US 2018/0169313 to Schwammenthal, which is the US national phase of International Patent Application PCT/IL2016/050525 to Schwammenthal (published as WO 16/185473), filed May 18, 2016, entitled "Blood pump," which claims priority from U.S. Provisional Patent Application 62/162,881 to Schwammenthal, filed May 18, 2015, entitled "Blood pump;"

US 2017/0100527 to Schwammenthal, which is the US national phase of International Patent Application PCT/IL2015/050532 to Schwammenthal (published as WO 15/177793), filed May 19, 2015, entitled "Blood pump," which claims priority from U.S. Provisional Patent Application 62/000,192 to Schwammenthal, filed May 19, 2014, entitled "Blood pump;"

U.S. Pat. No. 10,039,874 to Schwammenthal, which is the US national phase of International Patent Application PCT/IL2014/050289 to Schwammenthal (published as WO 14/141284), filed Mar. 13, 2014, entitled "Renal pump," which claims priority from (a) U.S. Provisional Patent Application 61/779,803 to Schwammenthal, filed Mar. 13, 2013, entitled "Renal pump," and (b) U.S. Provisional Patent Application 61/914,475 to Schwammenthal, filed Dec. 11, 2013, entitled "Renal pump;"

U.S. Pat. No. 9,764,113 to Tuval, issued Sep. 19, 2017, entitled "Curved catheter," which claims priority from U.S. Provisional Patent Application 61/914,470 to Tuval, filed Dec. 11, 2013, entitled "Curved catheter;" and U.S. Pat. No. 9,597,205 to Tuval, which is the US national phase of International Patent Application PCT/IL2013/050495 to Tuval (published as WO 13/183060), filed Jun. 6, 2013, entitled "Prosthetic renal valve," which claims priority from U.S. Provisional Patent Application 61/656,244 to Tuval, filed Jun. 6, 2012, entitled "Prosthetic renal valve."

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method, comprising:
manufacturing a housing for an impeller of a blood pump by:
treating a frame in order to enhance bonding between an inner surface of the frame and an inner lining;
subsequently, coupling the inner lining to the inner surface of the frame along at least a portion of a central cylindrical portion of the frame, the central cylindrical portion of the frame including struts that define a generally cylindrical shape;
subsequent to coupling the inner lining to the inner surface of the frame along at least a portion of the central cylindrical portion of the frame:
placing a mandrel inside the inner lining;
placing a portion of an elongate tube around at least a portion of the frame, the elongate tube including a proximal portion that defines at least one blood outlet opening;

while the portion of the elongate tube is disposed around at least the portion of the frame, heating the inner lining, the frame and the portion of the elongate tube, via the mandrel; and while heating the inner lining, the frame, and the portion of the elongate tube, applying pressure from outside the portion of the elongate tube, such as to cause the portion of the elongate tube to become coupled to the frame.

2. The method according to claim 1, wherein struts of the central cylindrical portion of the frame define cells which are configured such that, in a non-radially-constrained configuration of the frame, a width of each of each of the cells within the central cylindrical portion of the frame as measured around a circumference of the central cylindrical portion of the frame is less than 2 mm.

3. The method according to claim 1, wherein applying pressure from outside the portion of the elongate tube, while heating the inner lining, the frame and the portion of the elongate tube, comprises causing the portion of the elongate tube to conform with a structure of the struts of the frame.

4. The method according to claim 1, wherein coupling the inner lining to the inner surface of the frame along at least a portion of a central cylindrical portion of the frame comprises coupling the inner lining to the inner surface of the frame along at least a portion of a central cylindrical portion of the frame, such that the inner lining has a substantially circular cross section.

5. The method according to claim 1, wherein coupling the inner lining to the inner surface of the frame along at least a portion of a central cylindrical portion of the frame comprises coupling the inner lining to the inner surface of the frame along at least a portion of a central cylindrical portion of the frame, such that the inner lining provides a smooth inner surface to the portion of the central cylindrical portion of the frame to which the inner lining is coupled.

6. The method according to claim 1, wherein coupling the inner lining to the inner surface of the frame along at least a portion of a central cylindrical portion of the frame comprises avoiding air bubbles, folds, and other discontinuities in smoothness of a surface provided by the inner lining.

7. The method according to claim 1, wherein treating the frame in order to enhance bonding between the inner surface of the frame and the inner lining comprises applying a plasma treatment to the frame.

8. The method according to claim 1, wherein coupling the inner lining to the inner surface of the frame along at least a portion of a central cylindrical portion of the frame comprises:

placing the inner lining over a mandrel;

placing the frame over the inner lining; and applying pressure via a heat shrinking process.

9. The method according to claim 1, wherein treating the frame in order to enhance bonding between the inner surface of the frame and the inner lining comprises dipping the frame in a solution that contains the material from which the inner lining is made.

10. The method according to claim 9, wherein the inner lining comprises polyurethane and wherein dipping the frame in the solution comprises dipping the frame in a polyurethane solution.

11. The method according to claim 1, wherein treating the frame in order to enhance bonding between the inner surface of the frame and the inner lining comprises spraying the inner surface of the portion of the central cylindrical portion of the frame with a solution that contains the material from which the inner lining is made.

12. The method according to claim 11, wherein the inner lining comprises polyurethane and wherein spraying the inner surface of the portion of the central cylindrical portion of the frame comprises spraying the inner surface of the portion of the central cylindrical portion of the frame with a polyurethane solution.

13. The method according to claim 1, wherein placing the mandrel inside the inner lining subsequent to coupling the inner lining to the inner surface of the frame along at least the portion of the central cylindrical portion of the frame comprises placing a mandrel that is shorter than a length of the inner lining inside the inner lining.

14. The method according to claim 13, wherein placing the mandrel inside the inner lining subsequent to coupling the inner lining to the inner surface of the frame along at least the portion of the central cylindrical portion of the frame comprises placing the mandrel within the inner lining such that margins are left outside of the mandrel at each end of the inner lining.

15. The method according to claim 14, wherein placing the mandrel within the inner lining such that margins are left outside of the mandrel at each end of the inner lining comprises preventing the mandrel from coming into direct contact with the frame or the pump-outlet tube, thereby protecting the pump-outlet tube from being overheated and becoming damaged by the heating of the mandrel.

16. The method according to claim 1, wherein treating the frame in order to enhance bonding between the inner surface of the frame and the inner lining comprises dipping the frame in a coupling agent that has at least two functional groups that are configured to bond respectively with the frame and with a material form which the inner lining is made.

17. The method according to claim 16, wherein the inner lining comprises polyurethane and wherein dipping the frame in the coupling agent comprises dipping the frame in the coupling agent comprises dipping the frame in a silane solution.

* * * * *